US009702010B2

(12) United States Patent
Santin

(10) Patent No.: US 9,702,010 B2
(45) Date of Patent: *Jul. 11, 2017

(54) **THERAPY WITH *CLOSTRIDIUM PERFRINGENS* ENTEROTOXIN TO TREAT OVARIAN AND UTERINE CANCER**

(71) Applicant: YALE UNIVERSITY, New Haven, CT (US)

(72) Inventor: Alessandro D. Santin, Orange, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/175,676

(22) Filed: Feb. 7, 2014

(65) Prior Publication Data

US 2015/0218644 A1 Aug. 6, 2015

Related U.S. Application Data

(63) Continuation of application No. 13/250,380, filed on Sep. 30, 2011, now Pat. No. 8,664,184, which is a continuation of application No. 11/248,702, filed on Oct. 12, 2005, now Pat. No. 8,247,371.

(60) Provisional application No. 60/618,653, filed on Oct. 14, 2004.

(51) Int. Cl.
| | |
|---|---|
| *A61K 38/00* | (2006.01) |
| *C12Q 1/68* | (2006.01) |
| *A61K 38/16* | (2006.01) |
| *A61K 38/48* | (2006.01) |
| *A61K 39/395* | (2006.01) |
| *A61K 45/06* | (2006.01) |
| *C07K 16/30* | (2006.01) |
| *A61K 39/00* | (2006.01) |

(52) U.S. Cl.
CPC .......... *C12Q 1/6886* (2013.01); *A61K 38/164* (2013.01); *A61K 38/4886* (2013.01); *A61K 39/395* (2013.01); *A61K 45/06* (2013.01); *C07K 16/30* (2013.01); *A61K 2039/505* (2013.01); *C12Q 2600/136* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 4,946,778 A | 8/1990 | Ladner et al. | |
| 6,126,945 A | 10/2000 | Terman et al. | |
| 8,247,371 B2 | 8/2012 | Santin et al. | |
| 8,664,184 B2 | 3/2014 | Santin | |
| 2006/0078941 A1 | 4/2006 | Santin | |

FOREIGN PATENT DOCUMENTS

| | | | |
|---|---|---|---|
| WO | 02060420 A2 | | 8/2002 |
| WO | WO 02/060420 | * | 8/2002 |
| WO | 03069307 A2 | | 8/2003 |
| WO | WO 03/069307 | * | 8/2003 |
| WO | 2005041865 A2 | | 5/2005 |

OTHER PUBLICATIONS

Rangel et al (Clinical Cancer Research, 2003, 9:2567-2575).*
Lo et al (Protein Engineering, 1998, 11:495-500).*
English translation of WO 02/060420, Adler et al, published Aug. 2002.*
Hibbs et al (J of Pathology, Aug. 2004, 165:397-414, IDS).*
Hough et al (Cancer Research, 2000, 60:6281-6287, IDS).*
Abu-Rustrum NR, et al. Salvage weekly paclitaxel in recurrent ovarian cancer. Seminars in Oncology, 1997;14 Suppl 15: Abstract.
Aigner S, et al. D24, a mucin-type glyocoprotein is a ligand for P-selectin on human tumor cells. Blood, 1997;89 (9):3385-3395.
Bellone S, et al. Selection of HER-2/ neu-positive tumor cells in early stage cervical cancer: implications for Herceptin-mediated therapy. Gynecol Oncol, 2003;91(1):231-240.
Britstow RE, et al. Clinico-pathological features associated with HER-2/neu overexpression in uterine papillary serous carcinoma (UPSC) Gynecol Oncol, 2004;Abstract194;92:480.
Cane S, et al. The novel serine protease tumor-associated differentially expressed gene-14 (KLK8/Neuropsin.Ovasin) is highly overexpressed in cervical cancer. Am J Obstet Gynecol, 2004;190(1):60-66.
Cannon MJ, et al. Immunological treatment of ovarian cancer. Curr Opin Obstet Gynecol, 2004;16(1):87-92.

(Continued)

*Primary Examiner* — Laura B Goddard
(74) *Attorney, Agent, or Firm* — Henry D. Coleman; R. Neil Sudol

(57) ABSTRACT

The invention discloses high levels of receptors for *Clostridium perfringens* enterotoxin (CPE) have been found in ovarian cancer and uterine cancer tissue samples. In addition, successful in vivo treatment of a mouse model of ovarian cancer with intraperitoneal injection of CPE is disclosed. High levels of Ep-CAM protein is also disclosed in ovarian cancer tissue samples. Thus, the invention provides a method of treating ovarian cancer and uterine cancer by administering CPE. The invention also provides a method of treating cancer in a mammal involving intraperitoneal administration of CPE, where at least some cancerous cells are located in or adjacent to the peritoneal cavity of the mammal. The invention also provides a method of treating ovarian cancer involving administering an anti-Ep-CAM antibody. The invention also provides a method of treating cancers expressing claudin-3 or claudin-4 by administering an antibody against claudin-3 and/or an antibody against claudin-4. The invention also provides a method of protecting a mammal from CPE toxicity involving administering a protective agent that binds to claudin-3 and/or claudin-4 and inhibits CPE binding to claudin-3 and/or claudin-4.

14 Claims, 36 Drawing Sheets

(56) References Cited

OTHER PUBLICATIONS

Cannon MJ, et al. Novel target antigens for dendritic cell-based immunotherapy against ovarian cancer. Expert Rev Anticancer Ther, 2002;2(1):97-105.

Carson DD, et al. Changes in gene expression during the early to mid-luteal . . . Molecular Human Reproduction, 2002;8:871-879.

Casey JL, et al. Preparation, characterisation and tumour targeting of cross-linked divalent and trivalent anti-tumour Fab fragments. Br J Cancer, 1996;74(9):1397-1405.

Casey MJ, et al. Peritoneal carcinoma in women with genetic susceptibility: implications for Jewish populations. Familial Cancer, 2004;3:265-281.

Czeczulin et al. Infection and Immunity, 1993;61:3429-3439.

Diamandis EP, et al. Human kallikrein 6 (hK6): a new potential serum biomarker for diagnosis and prognosis of ovarian carcinoma. J Clin Oncol, 2003;21(6):1035-1043.

Eisen MB, et al. Cluster analysis and display of genome-wide expression patterns. Proc Natl Acad Sci USA, 1998;95:14863-14868.

Friederichs J, et al. The CD24/P-selectin binding pathway initiate lung arrest of human A125 adenocarcinoma cells. Cancer Res, 2000;60(23):6714-6722.

GenBank accession # M98037, Sep. 1993.

Goff, et al. Am J Obstet Gynecol, 2003;188:1556-1564.

Hanna et al. Mapping of functional regions of Clostridium perfringens type A enterotoxin. Infection and Immunity, 1992;60:2110-2114.

Hanna PC, et al. Localization of the receptor-binding region of Clostridium perfringens enterotoxin utilizing cloned toxin fragments and synthetic peptides. The 30 C-terminal amino acids define a functional binding region. J Biol Chem, 1991;266(17):11037-11043.

Hibbs et al. J of Pathology, Aug. 2004;165:397-414.

Hough CD, et al. Coordinately up-regulated genes in ovarian cancer. Cancer Res, 2001;61(10):3869-3876.

Hough CD, et al. Large-scale serial analysis of gene expression reveals genes differentially expressed in ovariaan cancer. Cancer Res, 2000;60(22):6281-6287.

Ismail RS, et al. Differential gene expression between normal and tumor-derived ovarian epithelial cells. Cancer Res, 2000;60(23):6744-6749.

Iwamoto Y, et al. YIGSR, a synthetic laminin pentapeptide, inhibits experimental metastasis formation. Science, 1997;238(4830):1132-1134.

Janes PW, et al. Structural determinants of the interaction between the erbB2 receptor and the Src homology 2 domain of Grb7. J Biol Chem, 1997;272(13):8490-8497.

Jazaeri AA, et al. Molecular determinants of tumor differentiation in papillary serous ovarian carcinoma. Mol Carcinog, 2003;36(2):53-59.

Katahira J, et al. Clostridium perfringens enterotoxin utilizes two structurally related membrane proteins as functional receptors in vivo. J Biol Chem, 1997;272(42):26652-26658.

Katahira J, et al. Molecular cloning and functional characterization of the receptor for Clostridium perfringens enterotoxin. J Cell Biol, 1997;136(6):1239-1247.

Kokai-Kun JF, et al. Identification of a Clostridium perfringens enterotoxin region required for large complex formation and cytotoxicity by random mutagenesis. Infect Immun, 1999;67(11):5634-5641.

Kokai-Kun JF, McClane BA. Deletion analysis of the Clostridium perfringens enterotoxin. Infect Immun, 1997;65 (3):1014-1022.

Kokai-Kun JF, McClane BA. Determination of functional regions of Clostridium perfringens enterotoxin through deletion analysis. Clin Infect Dis, 1997;25 Suppl 2:S165-S167.

Kokai-Kun JF, McClane BA. Evidence that region(s) of the Clostridium perfringens enterotoxin molecule remains exposed on the external surface of the mammalian plasma membrane when the toxin is sequestered in small or large complexes. Infect Immun, 1996;64(3):1020-1025.

Koshikawa N, et al. Overexpression of laminin gamm2 chain monomer in invading gastric carcinoma cells. Cancer Res, 1999;59(21):5596-5601.

Litvinov SV, et al. Ep-CAM: a human epithelial antigen is a homophilic cell-cell adhesion molecule. J Cell Biol, 1994;125(2):437-446.

Long H, et al. Expression of Clostridium perfringens enterotoxin receptors claudin-3 and claudin-4 in prostate cancer epithelium. Cancer Res, 2001;61(21):7878-7881.

Lukes AS, et al. Multivariable analysis of DNA ploidy, p53, and HER-2/neu as prognostic factors in endometrial cancer. Cancer, 1994;73(9):2380-2385.

Lustgarten J, et al. Redirection effector T cells through their IL-2 receptors. J Immunol, 1999;162(1):359-365.

Marchetti P, et al. Weekly administration of paclitaxel: theoretical and clinical basis. Critical Reviews in Oncology/Hematology, 2002;44:S3-S13.

McClane BA, Wnek AP. Studies of Clostridium perfringens enterotoxin action at different temperatures demonstrate a correlation between complex formation and cytotoxicity. Infect Immun, 1990;58(9):3109-3115.

McClane BA. An overview of Clostridium perfringens enterotoxin. Toxicon, 1996;34(11-12):1335-1343.

McClane BA. Clostridium perfringens enterotoxin acts by producing small molecule permeability alterations in plasma membranes. Toxicology, 1994;87(1-3):43-67.

McClane BA. The complex interactions between Clostridium perfringens enterotoxin and epithelial tight junctions. Toxicon, 2001;39(11):1781-1791.

Michl P, et al. Claudin-4: a new target for pancreatic cancer treatment using Clostridium perfringens enterotoxin. Gastroenterology, 2001;121(3):678-684.

Morita K, et al. Claudin multigene family encoding four-transmembrane domain protein components of tight junction strands. Proc Natl Acad Sci USA, 1999;96(2):511-516.

Nichols LS, et al. Claudin 4 protein expression in primary and metastatic pancreatic cancer. 2004;121:226-230.

Nilo L. Measurement of biological activates of purified and crude enterotoxin of Clostridium perfringens. Infect Immun, 1975;12(2):440-442.

Ono K, et al. Identification by cDNA microarray of genes involve in ovarian carcinogenesis. Cancer Res, 2000;60 (18):5007-5011.

Packeisen J, et al. Detection of surface antigen 17-1A in breast and colorectal cancer. Hybridoma, 1999;18(1):37-40.

Pusztai et al. Acta Oncol, 1998;37:629-640.

Rangel LB, et al. Tight junction proteins claudin-3 and claudin-4 are frequently overexpressed in ovarian cancer but not in ovarian cystadenomas. Clin Cancer Res, 2003;9(7):2567-2575.

Redlich et al. J Surgical Oncology, 1994;57:191-195.

Riethmuller G, et al. Monoclonal antibody therapy for resected Dukes C colorectal cancer: seven-year outcome of a multicenter randomized trial. J Clin Oncol, 1998;16(5):1788-1794.

Santin AD, et al. Discrimination between uterine serous paillary carcinomas and ovarian serous papillary tumours by gene expression profiling. Br J Cancer, 2004;90(9):1814-1824.

Santin AD, et al. Gene expression fingerprint of uterine serous papillary carcinoma: identification of novel molecular markers for uterine serous cancer diagnosis and therapy. Br J Cancer, 2005;92(8):1561-1573.

Santin AD, et al. Gene expression profiles in primary ovarian serous papillary tumors and normal ovarian epithelium: identification of candidate molecular markers for ovarian cancer diagnosis and therapy. Int J Cancer, 2004;112 (1):14-25.

Santin AD, et al. Human kallikrein 6: a new potential serum biomarker for uterine serous papillary cancer. Clin Cancer Res, 2005;11(9):3320-3325.

Santin AD, et al. Overexpression of HER-2/neu in uterine serous papillary cancer. Clin Cancer Res, 2002;8:1271-1279.

Santin AD, et al. The novel serine protease tumor-associated differentially expressed gene-15 (matriptase/MT-SP1) is highly overexpressed in cervical carcinoma. Cancer, 2003;98(9):1898-1904.

(56) References Cited

OTHER PUBLICATIONS

Santin AD, et al. Treatment of chemotherapy-resistant human ovarian cancer xenografts in C.B-17/SCID mice by intraperitoneal administration of Clostridium perfringens enterotoxin. Cancer Res, 2005;65(10):4334-4342.
Santin AD. HER2/neu overexpression: has the Achilles' heel of uterine serous papillary carcinoma been exposed? Gynecol Oncol, 2003;88(3):263-265.
Seth P, et al. Cellular and molecular targets of estrogen in normal human breast tissue. Cancer Res, 2002;62 (16):4540-4544.
Shridhar V, et al. Genetic analysis of early-versus late-stage ovarian tumors. Cancer Res, 2001;61(15):5895-5904.
Shridhar V, et al. Identification of underexpressed genes in early- and late-stage primary ovarian tumors by suppression subtraction hybridization. Cancer Res, 2002;62(1):262-270.
Slamon DJ, et al. Use of chemotherapy plus a monoclonal antibody against HER2 for metastatic breast cancer that overexpresses HER2. N Engl J Med, 2001;344(11):783-792.
Terris B, et al. Characterization of gene expression profiles in intraductal papillary-mucinous tumors of the pancreas. Am J Pathol, 2002;160(5):1745-1754.
Tsukita S, Furuse M. The structure and function of claudins, cell adhesion molecules at tight junctions. Ann N Y Acad Sci, 2000;915:129-135.
Villella JA, et al. Proc Am Soc Clin Oncol, 2003 Abs No. 1870.
Vollmers HP, et al. Monoclonal antibodies which prevent experimental lung metastases. Interference with the adhesion of tumor cells to laminin. FEBS Lett, 1984;172(1):17-20.
Wallace FM, et al. Evidence for Clostridium perfringens enterotoxin (CPE) inducing a mitogenic and cytokine response in vitro and a cytokine response in vivo. Curr Microbiol, 1999;38(2):96-100.
Welsh JB, et al. Analysis of gene expression profiles in normal and neoplastic ovarian tissue samples identifies candidate molecular markers of epithelial ovarian cancer. Proc Natl Acad Sci USA, 2001;98(3):1176-1181.
Yoshida Y, et al. Role of laminin in ovarian cancer tumor growth and metastasis via regulation of Mdm2 and Bcl-2 expression. Int J Oncol, 2001;18(5):913-921.

* cited by examiner

THERAPY WITH *CLOSTRIDIUM PERFRINGENS* ENTEROTOXIN TO TREAT OVARIAN AND UTERINE CANCER

This application is a continuation of and claims priority from U.S. patent application Ser. No. 13/250,380 filed Sep. 30, 2011, now U.S. Pat. No. 8,664,184, which is a continuation application of and claims priority from U.S. patent application Ser. No. 11/248,702 filed Oct. 12, 2005 "Therapy with *Clostridium Perfringens* Enterotoxin to Treat Ovarian and Uterine Cancer", now U.S. Pat. No. 8,247,371, which claims the benefit of priority to U.S. provisional patent application Ser. No. 60/618,653, "Therapy with *Clostridium Perfringens* Enterotoxin to Treat Ovarian and Uterine Cancer", filed Oct. 14, 2004. The three priority documents are incorporated in their entirety into this application.

BACKGROUND OF THE INVENTION

Ovarian carcinoma remains the cancer with the highest mortality rate among the gynecological malignancies, with 25,400 new cancer cases estimated in 2003 in the United States alone. Ovarian serous papillary carcinoma (OSPC) is the most common histologic type of ovarian carcinoma. Because of the insidious onset of the disease and the lack of reliable screening tests, two-thirds of patients have advanced disease when diagnosed; and although many patients with disseminated tumors respond initially to standard combinations of surgical and cytological therapy, nearly 90% will develop recurrence and succumb to their disease.

Uterine cancer is the most prevalent gynecological tumor in women, with an estimated 40,100 cases and 6,800 deaths in the United States in 2003. On the basis of clinical and histopathological variables, two subtypes of endometrial carcinoma, Type I and II tumors, have been described (1,2). Type I endometrial cancers, which account for about 80% of cases, are usually well differentiated and endometrioid in histology. They are diagnosed predominantly in younger women, and have a favorable prognosis. Type II endometrial cancers are poorly differentiated tumors, often with serous papillary or clear cell histology. Although type II tumors account for only a minority of endometrial carcinoma cases, about 50% of all relapses occur in this group.

Uterine serous papillary carcinoma (USPC) tumors represent the most aggressive variant of Type II endometrial cancer and may constitute up to 10% of endometrial tumors (3-10). The microscopic criteria for diagnosis of USPC were first outlined by Hendrickson in 1982 (10). Typically, the neoplastic epithelium is characterized by serous differentiation with psammoma bodies present and with predominantly papillary architecture (11). Pleomorphism, grade III nuclear atypia with prominent nucleoli and vesicular chromatin pattern, as well as a high mitotic activity are commonly detected in this tumor. Clinically, USPC has a propensity for intraabdominal and lymphatic spread even at presentation and is characterized by a highly aggressive biologic behavior (3-10, 12). USPC is a chemoresistant disease from onset, with responses to combined cisplatinum-based chemotherapy of about 20% and short duration (7-9). The survival rate is dismal, even when USPC is only a minor component of the histologically more common endometrioid adenocarcinoma, and widespread metastasis and high mortality may occur even in those cases in which tumor is confined to the endometrium or to an endometrial polyp (4, 6, 12). The overall 5-year survival is about 30% for all stages and the recurrence rate after surgery is extremely high (50% to 80%).

Pancreatic cancer is the fifth leading cause of cancer death in the U.S. and has one of the highest mortality rates of any malignancy.

Chemotherapy resistance is a major problem in treatment of ovarian, uterine, and pancreatic cancers, and other cancers. Often a patient initially responds to chemotherapy, but the tumor develops resistance and recurs. New treatments for chemotherapy resistant tumors are needed.

Claudin-3 and claudin-4 are proteins found on the surface of cells of various tissue types involved in tight junctions connecting one cell to the adjacent cells (13). Claudins 3 and 4 have been found to be the receptors for *Clostridium perfringens* enterotoxin, a bacterial toxin that causes food poisoning (14-16).

Claudin-3 mRNA is expressed in normal prostate, colon, small bowel, and pancreas (17). Claudin-4 is expressed at high levels in colon, and at moderate levels in prostate, placenta, lung, pancreas, and lower levels in small bowel, kidney, and uterus (17). Claudin-3 mRNA expression in prostate adenocarcinoma was found to be equal to or greater than expression in surrounding normal prostate tissue (17). The prostate cancer cells in tissue culture were sensitive to killing by *Clostridium perfringens* enterotoxin (CPE) (17).

In another report, claudin-4 mRNA was found to be not expressed or weakly expressed in normal pancreas, but was highly expressed in most primary pancreatic carcinoma samples (18). Claudin-4 expression was also found in colon cancer, breast cancer, and gastric cancer samples (18). CPE was reported to kill pancreatic cancer cell lines in vitro (18). Pancreatic tumor xenografts were induced in nude mice, and the tumors were directly injected with CPE over the course of 5 days. The CPE treated tumors showed no increase in size and exhibited areas of necrosis, while the untreated tumors grew (18).

Hough et al. reported results of serial analysis of gene expression (SAGE) comparing expression of genes in ovarian surface epithelium, cystadenoma, and ovarian primary tumors (19). Many genes were found to be upregulated in ovarian tumors compared to normal ovarian epithelium. Several of these were surface proteins. Surface proteins shown to be upregulated included claudin-3 and -4, HE4, mucin-1, epithelial cellular adhesion molecule, and mesothelin (19). Claudin-3 and -4 mRNA and protein levels were also reported to be elevated in ovarian carcinoma samples as compared to normal ovarian tissue and ovarian cystadenoma (20).

New methods for treating cancer are needed. Methods for treating the most deadly cancers, including ovarian cancer, pancreatic cancer, and uterine serous papillary carcinoma, are particularly needed. Methods for treating chemotherapy resistant cancers are particularly needed. Preferably the methods would have reduced side effects and involve reduced toxicity for healthy non-target tissue.

SUMMARY

The invention is based in part on the discovery that expression of claudin-3 and -4 is higher in metastatic ovarian cancer cells than cells from primary ovarian tumors, and higher in chemotherapy-resistant ovarian cancer cells than in chemotherapy-naive ovarian cancer cells. Thus *Clostridium perfringens* enterotoxin (CPE) is well suited for use in treating ovarian cancer patients whose tumors have spread or resisted chemotherapy.

It has also been discovered that uterine serous papillary carcinoma (USPC) cells express 12-times more claudin-4 and 8-times more claudin-3 than healthy uterine epithelial cells.

It is demonstrated herein that ovarian cancer can be treated successfully in vivo in a mouse model with administration of CPE. Thus, one aspect of the invention is treating uterine or ovarian cancer, particularly metastatic or chemotherapy resistant forms of uterine or ovarian cancer, in vivo in a mammal by administering CPE.

One aspect of the invention is administering CPE intraperitoneally to treat tumors found in or adjacent to the peritoneal cavity. This reduces the toxicity of CPE administration because it spares tissues distant from the peritoneal cavity. That allows higher doses to be administered, increasing the efficacy against tumors in or near the peritoneal cavity.

Another aspect of the invention involves administering to non-target tissues an agent that protects cells against CPE toxicity in conjunction with intraperitoneal administration of CPE. This further protects the non-target tissues, reducing the side effects of CPE and allowing the use of higher doses of CPE. One such protective agent is a carboxy terminal fragment of the CPE protein.

Thus, one embodiment of the invention provides a method of treating cancer in a mammal involving: administering to the mammal a therapeutically effective amount of CPE or a pharmaceutically effective salt thereof; wherein the cancer is ovarian cancer or uterine cancer.

Another embodiment of the invention provides a method of treating cancer in a mammal involving: intraperitoneally administering to the mammal a therapeutically effective amount of CPE or a pharmaceutically acceptable salt thereof. This method is suitable when at least some cancerous cells are located in or adjacent to the peritoneal cavity of the mammal, and the cells are sensitive to CPE.

One embodiment of the invention provides a method of determining the sensitivity of a gynecological malignancy to CPE involving detecting the presence or absence of claudin-3 and/or claudin-4 in a tissue sample comprising a portion of the malignancy.

One embodiment of the invention provides a use of CPE to prepare a medicament effective to treat ovarian cancer or uterine cancer in a mammal.

One embodiment of the invention provides a use of CPE to prepare a medicament effective to treat cancer in a mammal, wherein the medicament is adapted for intraperitoneal administration.

It is also reported herein that the TROP-1/Ep-CAM gene and the Ep-CAM protein are overexpressed in ovarian serous papillary carcinoma (OSPC) compared to normal ovarian epithelium (NOVA). The TROP-1/Ep-CAM mRNA is expressed 39-fold higher in OSPC than in NOVA. Thus, antibodies against Ep-CAM can be an effective treatment for ovarian cancer.

Accordingly, one embodiment of the invention provides a method of treating cancer in a mammal involving administering to the mammal a therapeutically effective amount of an anti-Ep-CAM antibody.

Another embodiment of the invention is a method of determining the sensitivity of a gynecological malignancy to treatment with an anti-Ep-CAM antibody involving detecting the presence or absence of Ep-CAM in a tissue sample comprising a portion of the malignancy.

Another embodiment of the invention provides a method of protecting a mammal from CPE toxicity involving administering a non-toxic agent that binds to claudin-3 and/or claudin-4 and inhibits CPE binding to claudin-3 and/or claudin-4.

Another embodiment of the invention provides a method of treating cancer in a mammal involving administering to the mammal an antibody against claudin-3 and/or claudin-4, wherein cancerous cells in the mammal contain claudin-3 and/or claudin-4.

Another embodiment of the invention provides a humanized antibody against an extracellular portion of claudin-3 and/or an extracellular portion of claudin-4.

Another embodiment of the invention provides an antibody that includes an antigen-binding region comprising residues 290-319 of SEQ ID NO:1 or a fragment thereof that binds specifically to claudin-3 and/or claudin-4. The fragment may include residues 315-319 of SEQ ID NO:1

Another embodiment of the invention provides a method of treating cancer in a mammal involving: administering to the mammal a therapeutically effective amount of a cytotoxic agent that binds specifically to claudin-3 and/or claudin-4; wherein the cancer is ovarian cancer or uterine cancer.

Another embodiment of the invention provides an anticancer agent containing: (a) a moiety that binds specifically to claudin-3 and/or claudin-4; coupled to (b) a cytotoxic moiety; wherein the agent is effective to kill tumor cells overexpressing claudin-3 and/or claudin-4 in vitro or in vivo, and wherein the agent is not CPE.

BRIEF DESCRIPTION OF THE DRAWINGS

FIG. 2A, FIG. 2C, FIG. 2E, and FIG. 2G show the PCR analysis of TROP-1, CD24, CLDN3, and CLDN4, respectively.

FIG. 5A, FIG. 5C, FIG. 5E, FIG. 5G, FIG. SI, and FIG. 5K show the RT-PCR analysis of c-erbB2, GRB-7, CDKN2A/p14ARF, CDKN2A/p16, claudin-3, and claudin-4, respectively.

FIGS. 7A, B, C, and D. Quantitative RT-PCR analysis of claudin-3 and claudin-4 expression in chemotherapy naïve versus chemotherapy resistant/recurrent ovarian cancer. The Y axis represents the fold induction relative to normal ovary expression. The X axis represents each sample tested for claudin-3 and claudin-4. FIGS. 7A and 7B: 1 (chemotherapy naïve ovarian cancers=6 OSPC samples, mean±SEM); 2 (chemotherapy resistant/recurrent ovarian cancer=6 OSPC samples, mean±SEM) ($p<0.05$).

DETAILED DESCRIPTION

Definitions

Figure 1:
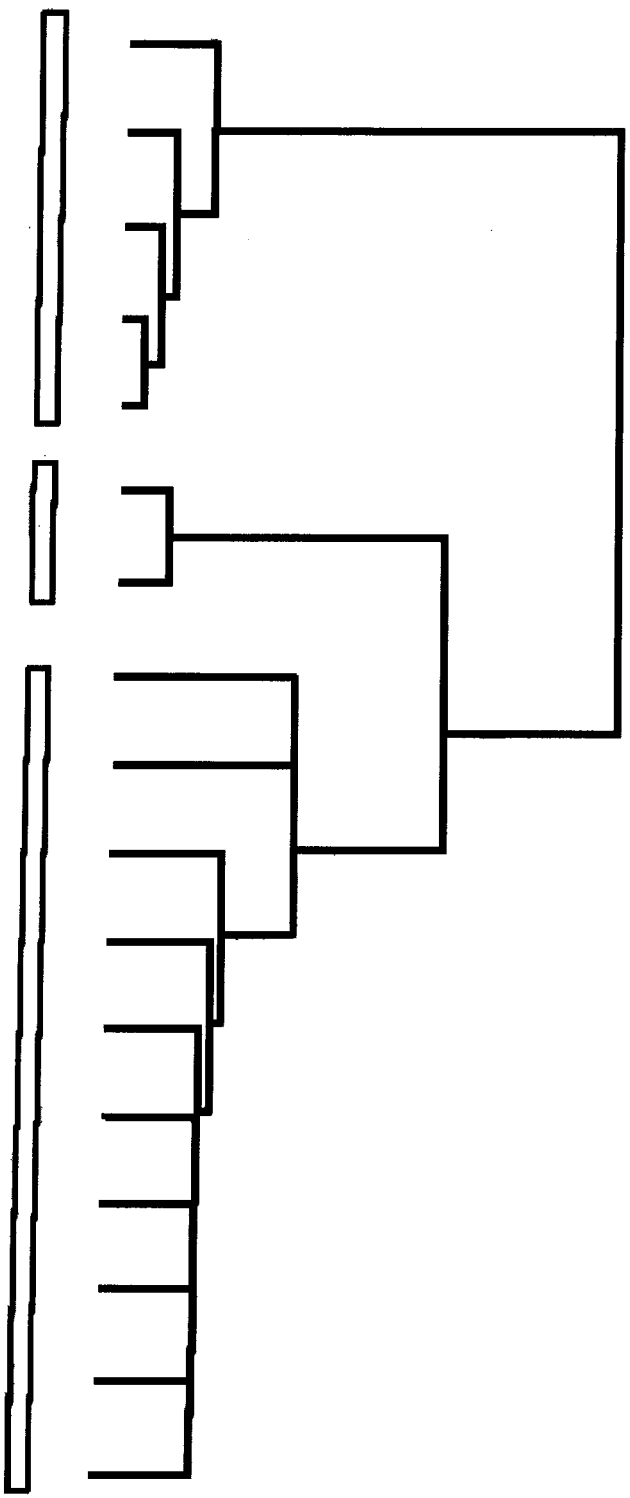
FIG. 1 is a schematic showing hierarchical clustering of 15 primary ovarian cell lines (10 OSPC and 5 NOVA) and 2 established OSPC cell lines (UCI-101 and UCI-107).
Figure 2A:
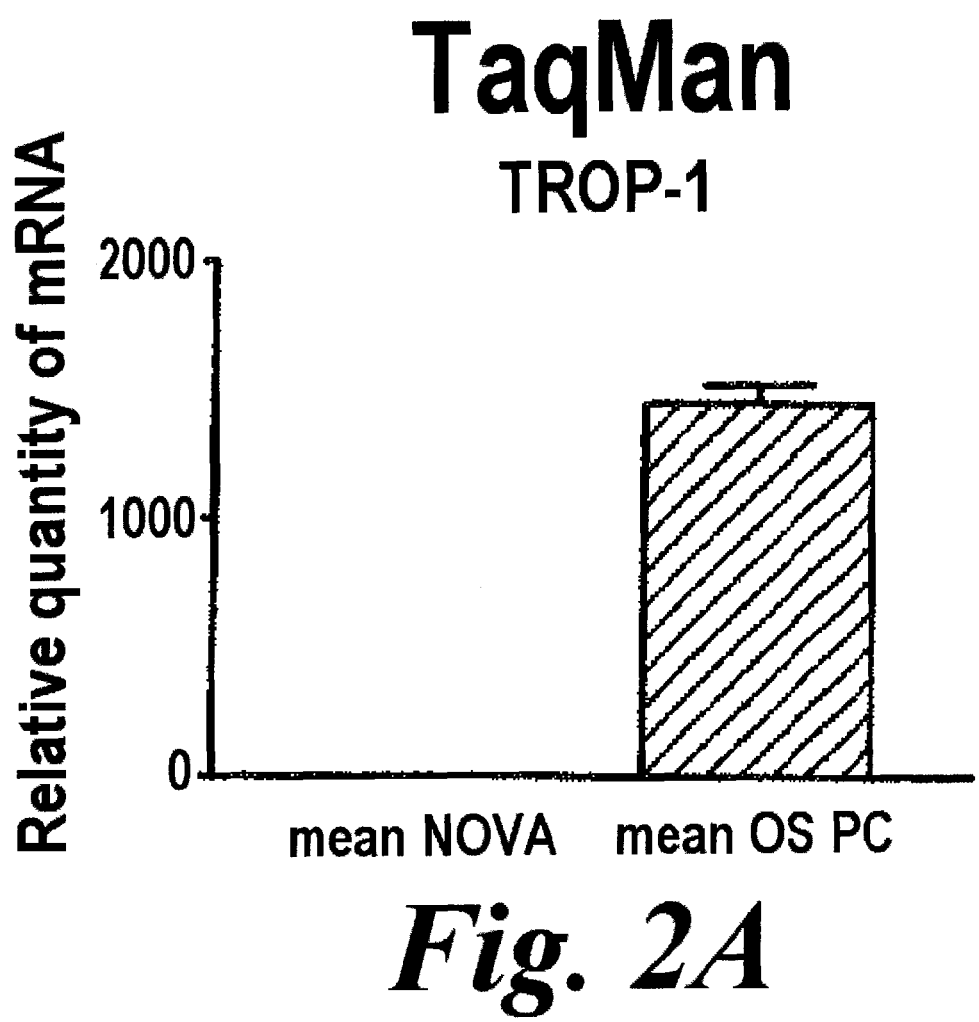
FIGS. 2A, B, C, D, E, F, G, and H show bar graphs of quantitative real-time PCR and microarray expression analyses of TROP-1, CD24, claudin-3, and claudin-4 genes differentially expressed between OSPC and NOVA.
Figure 2B:
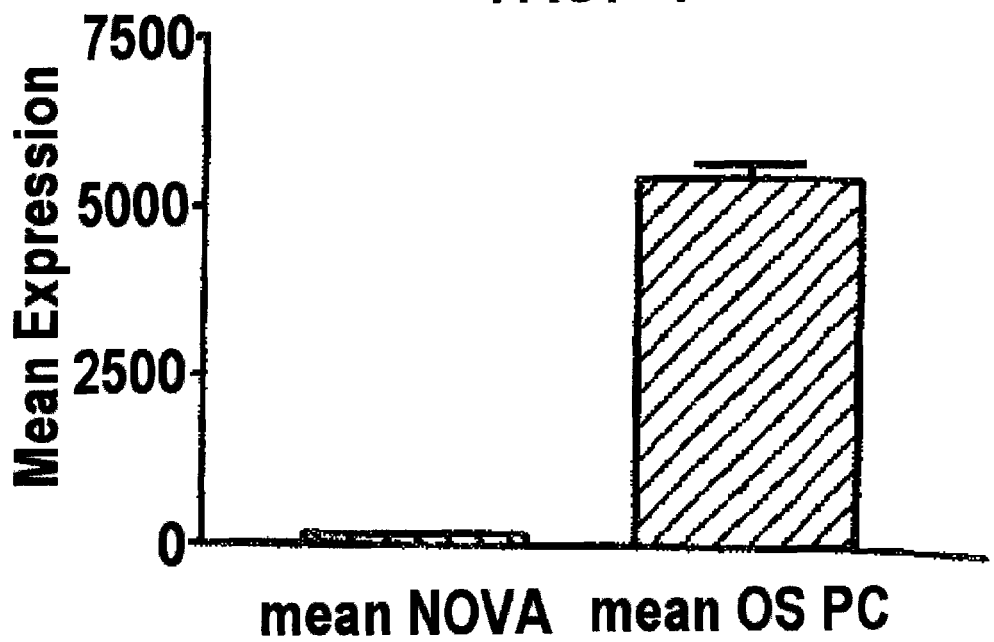
FIG. 2B, FIG. 2D, FIG. 2F, and FIG. 2H show the microarray expression analysis of TROP-1, CD24, claudin-3, and claudin-4, respectively.
Figure 2C:
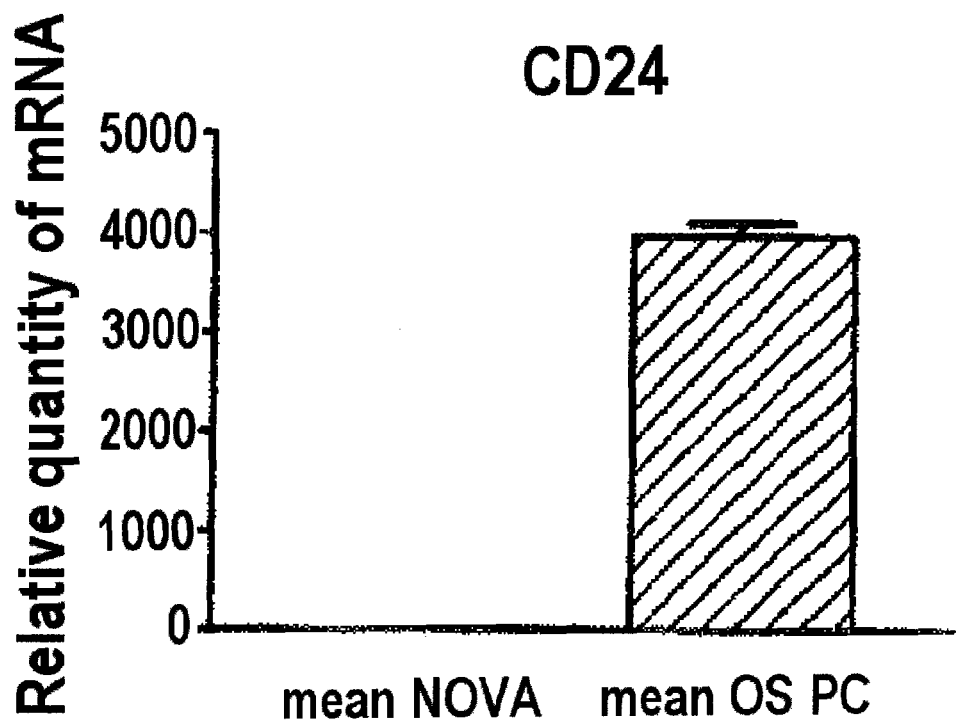
Figure 2D:
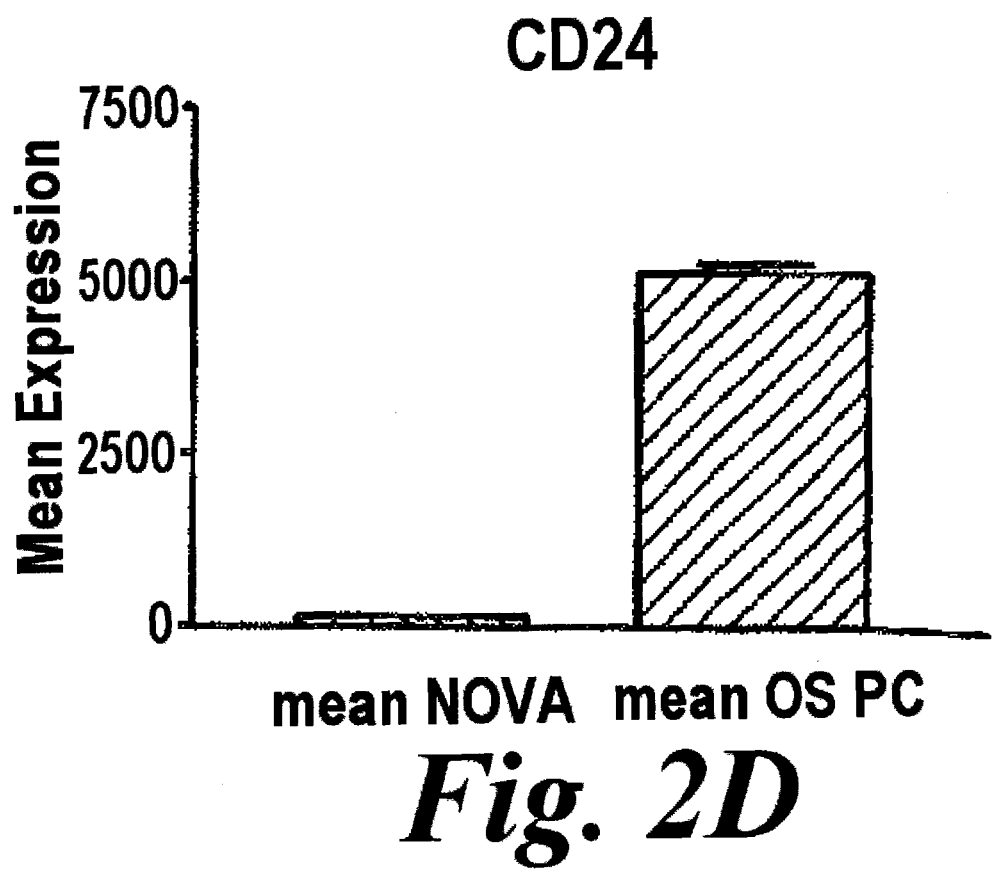
Figure 2E:
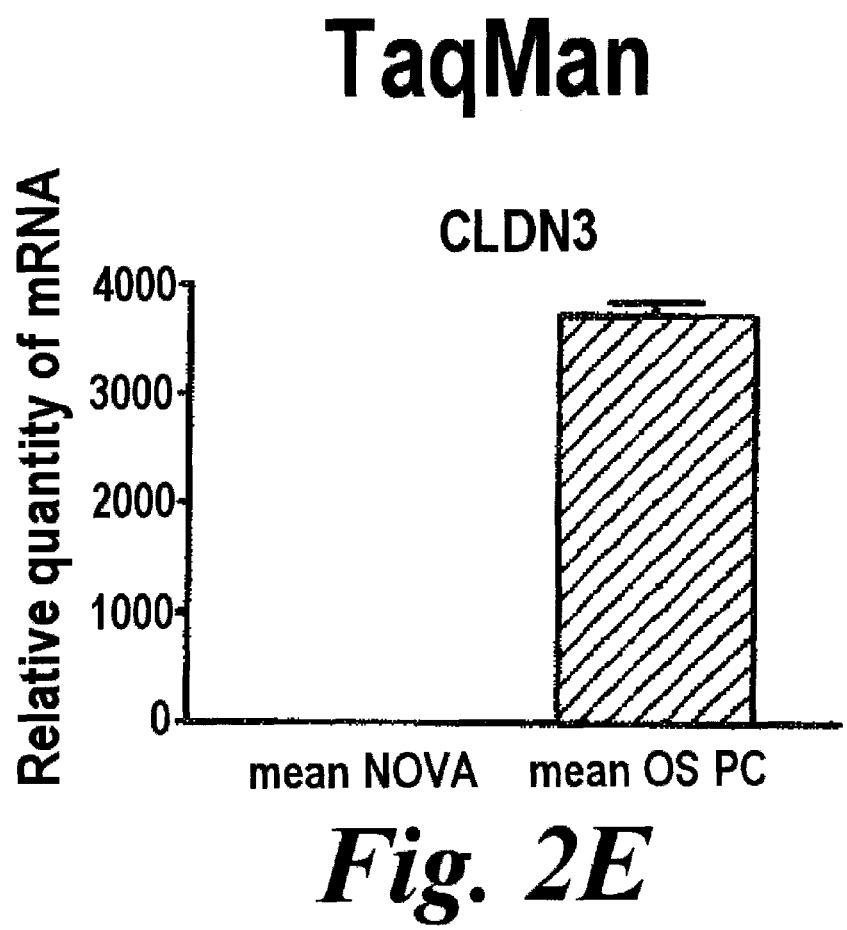
Figure 2F:
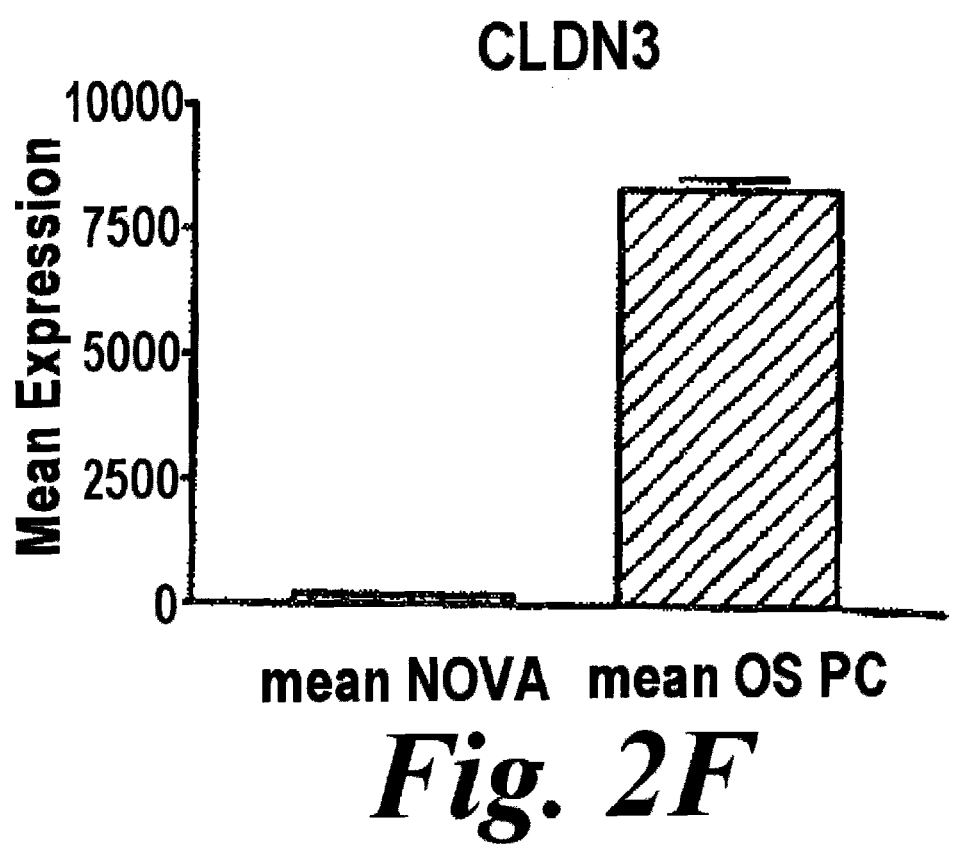
Figure 2G:
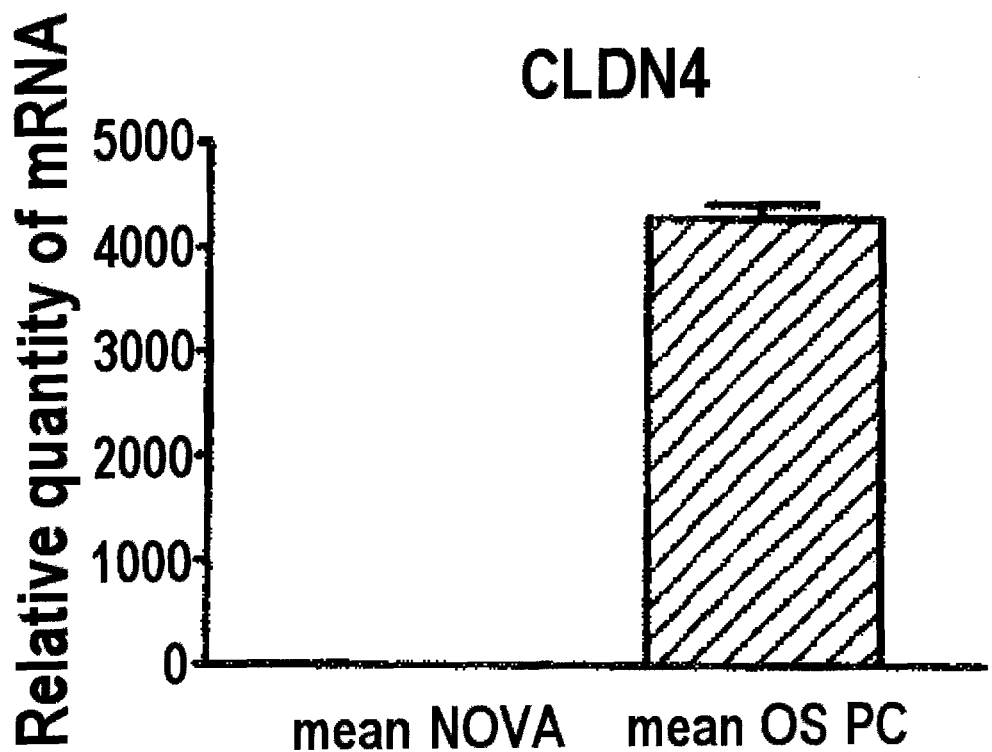
Figure 2H:
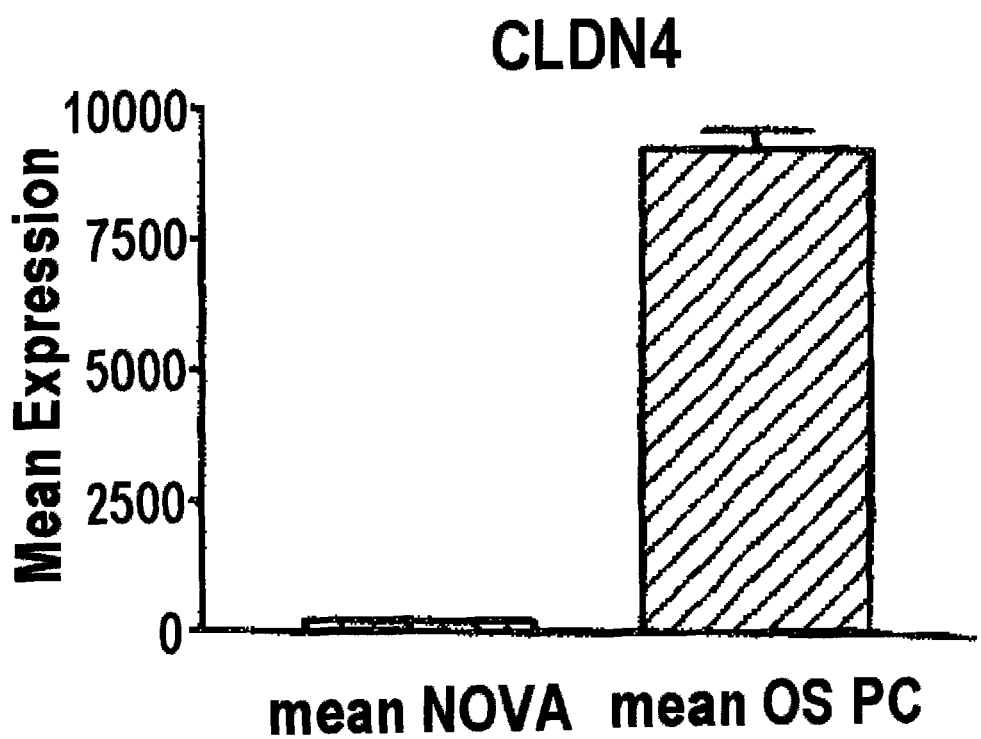
Figure 3A:
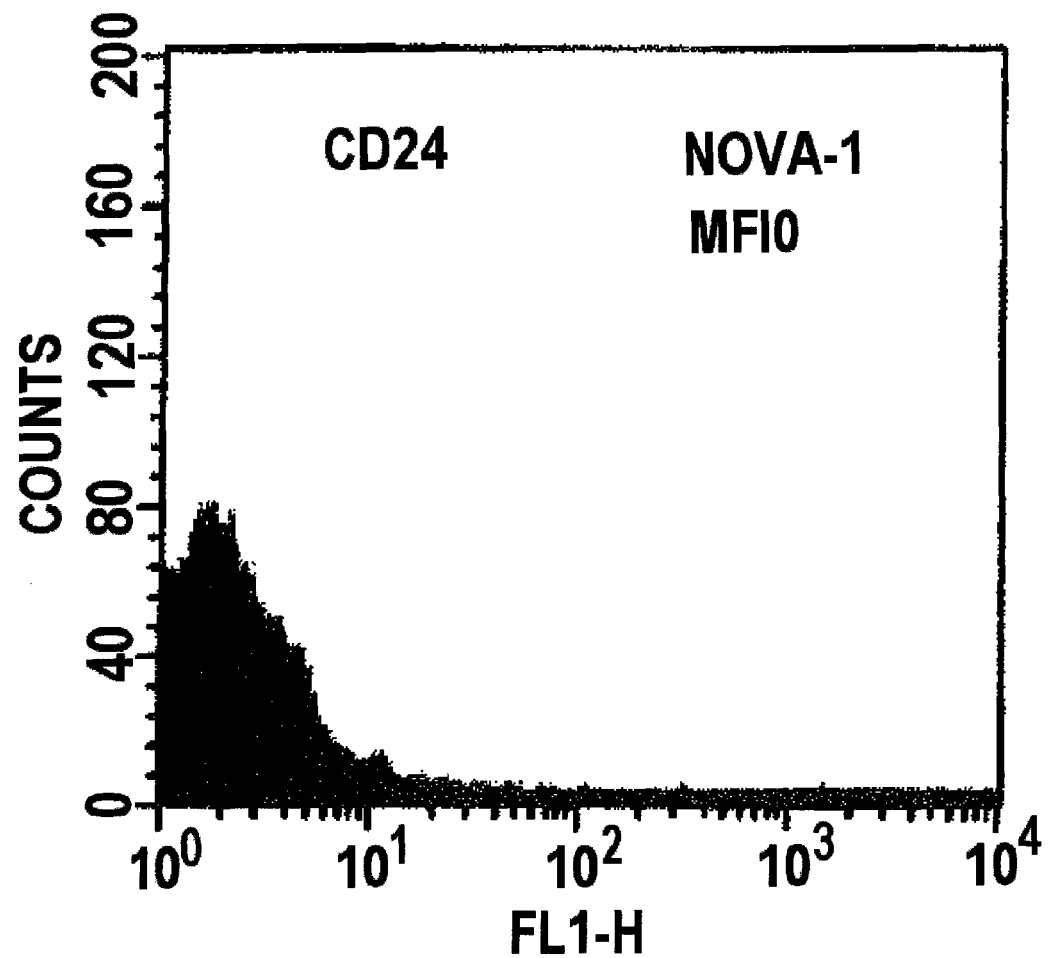
FIGS. 3A, B, C, D, E, and F show representative FACS analyses of CD24 staining (FIG. 3A, FIG. 3C, and FIG. 3E) and TROP-1/Ep-CAM staining (FIG. 3B, FIG. 3D, and FIG. 3F) of 2 primary OSPC cell lines and 1 NOVA cell line. Data on CD24 and TROP-1/Ep-CAM are shown in solid black, while isotype control MAb profiles are shown in white.
Figure 3B:
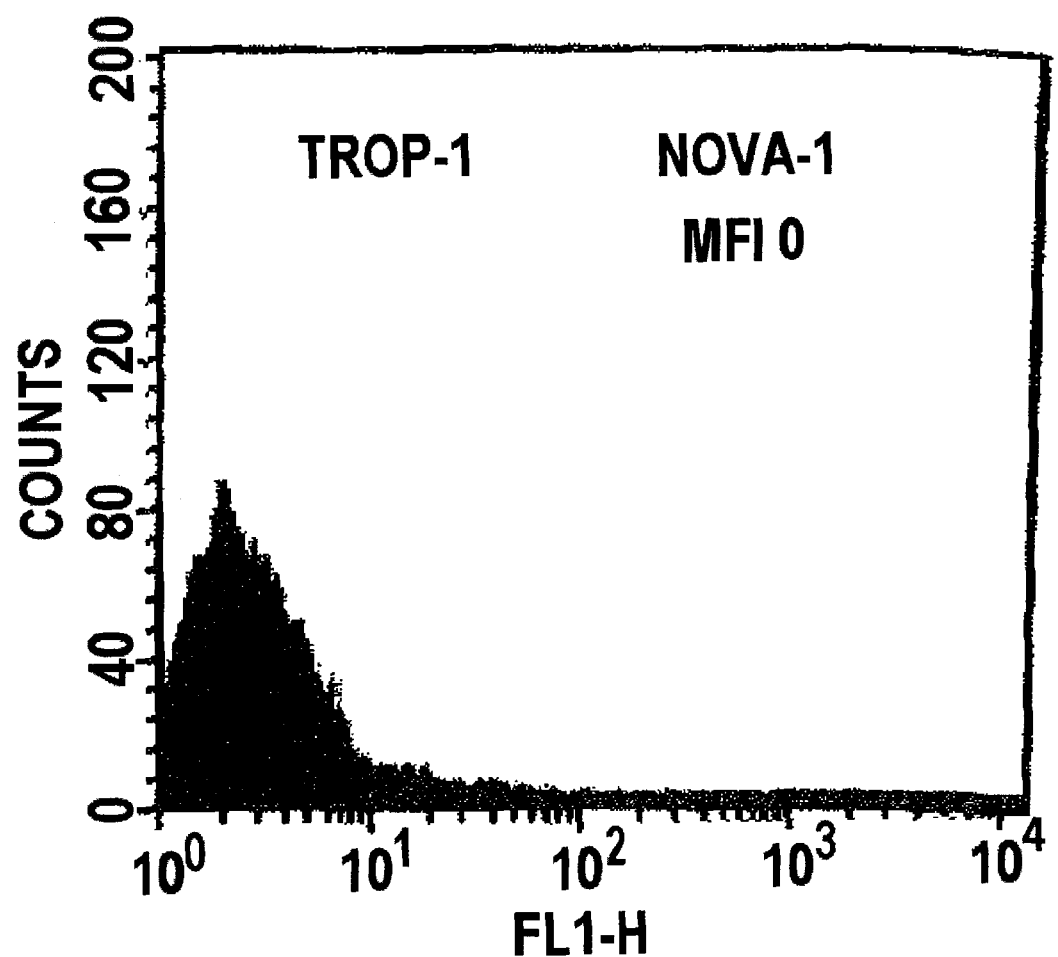
Figure 3C:
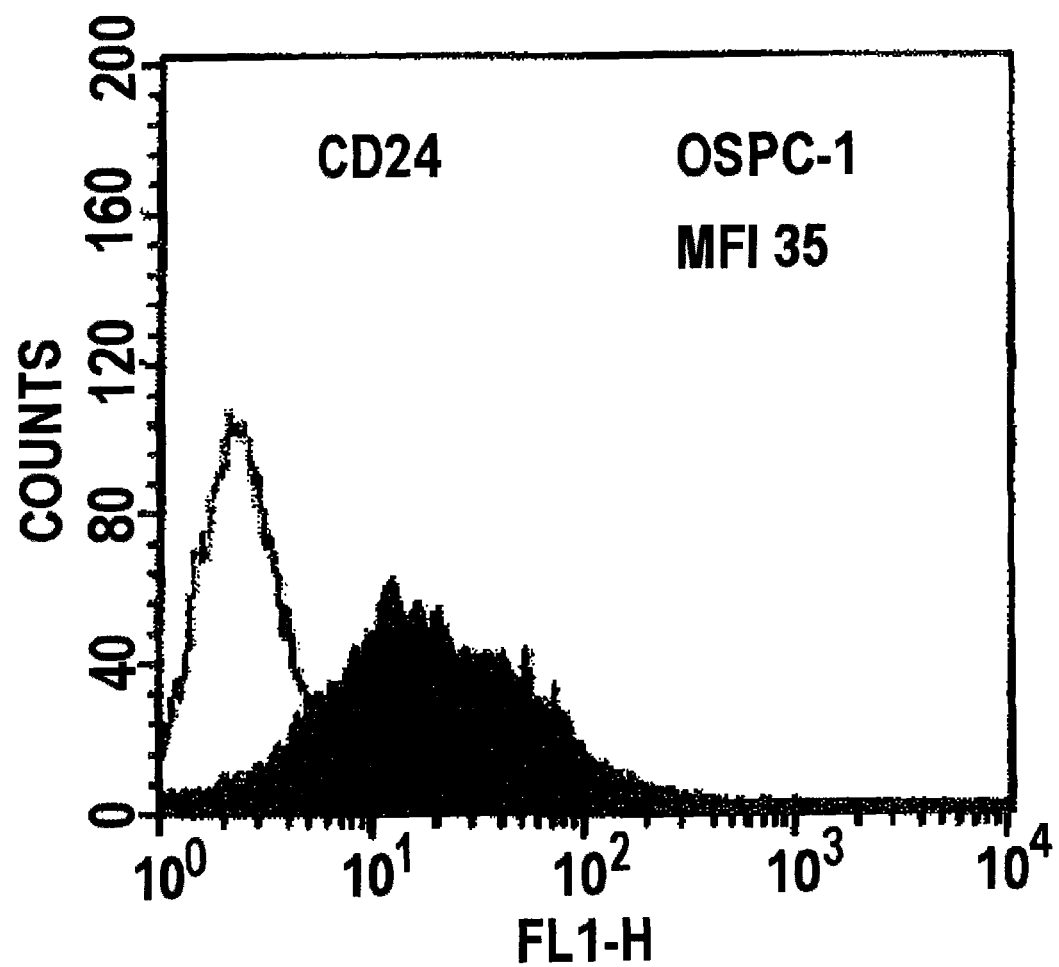
Figure 3D:
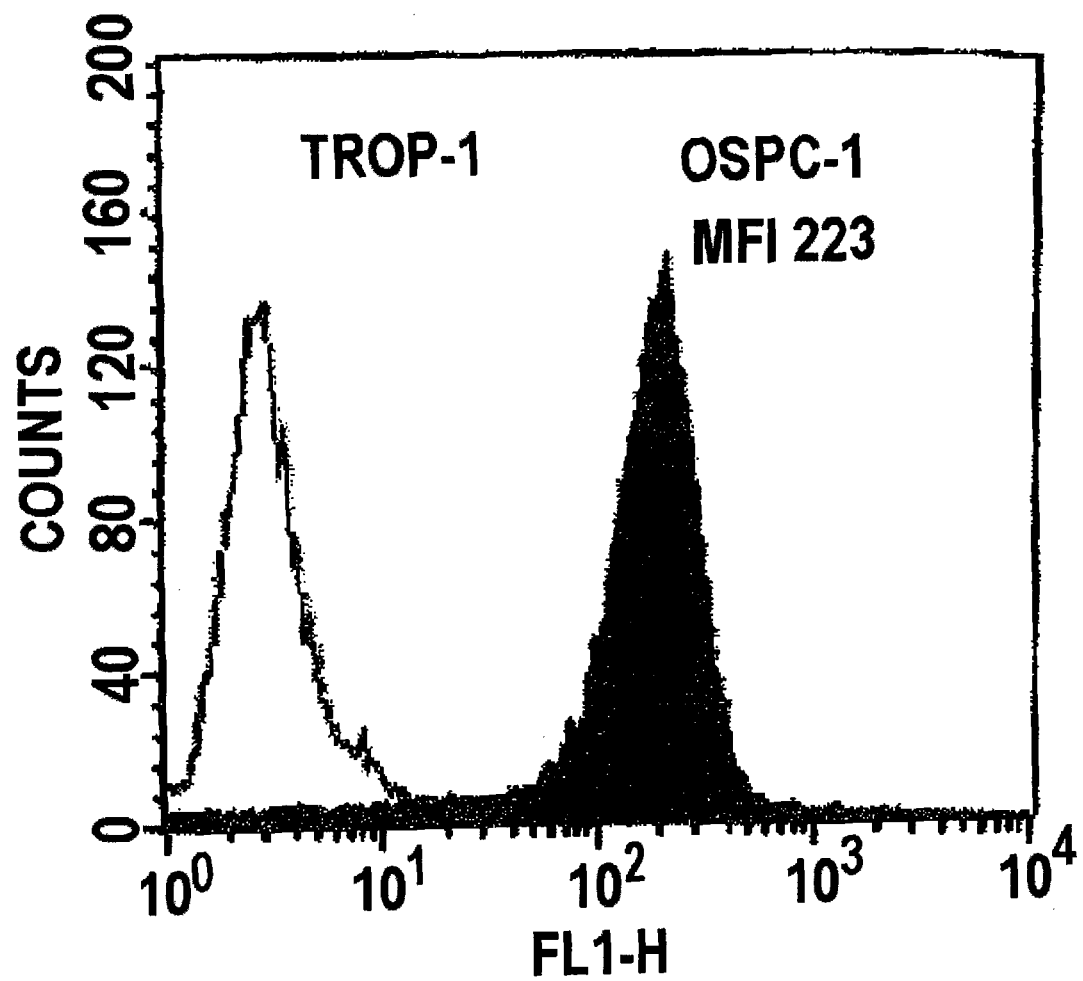
Figure 3E:
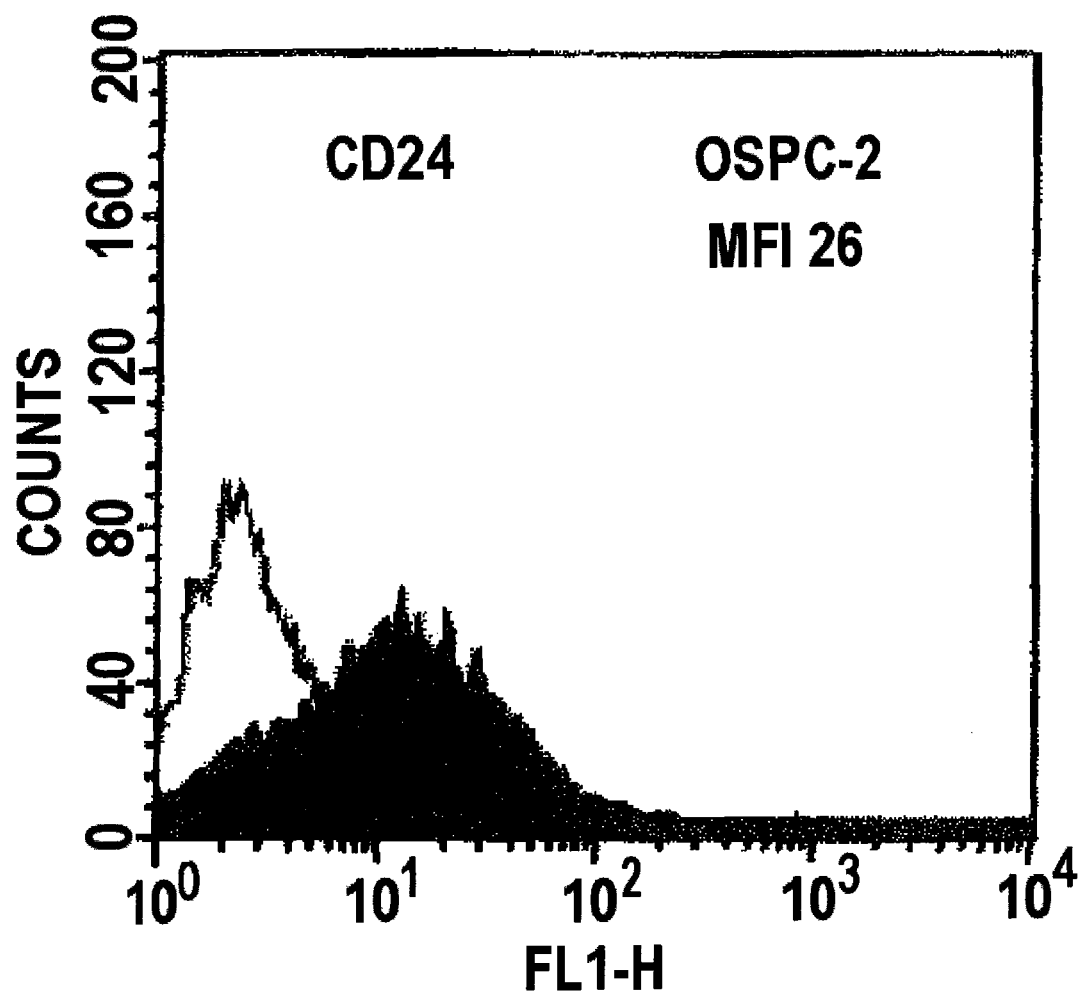
Figure 3F:
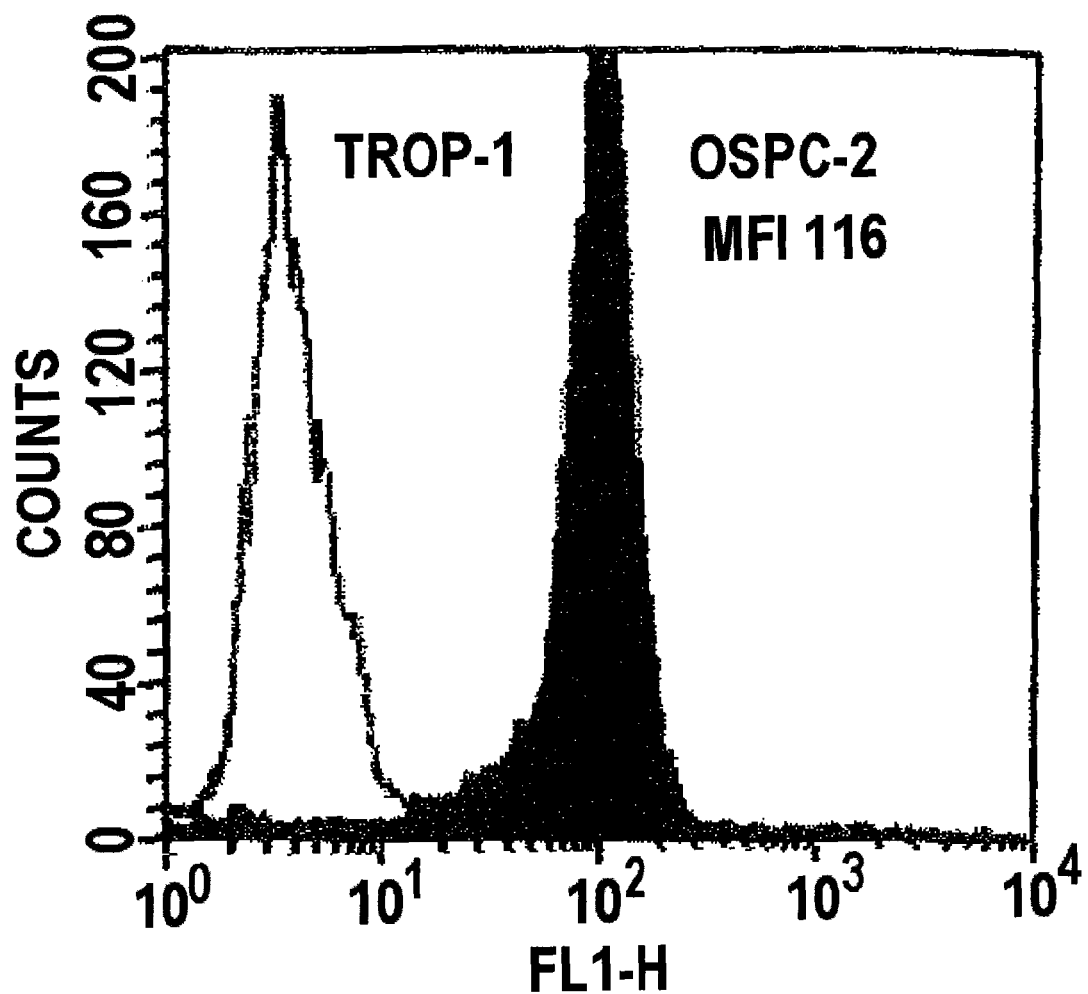

The term "*Clostridium perfringens* enterotoxin" (CPE) includes the native enterotoxin (SEQ ID NO:1) or an engineered, mutant, or variant enterotoxin that is toxic and binds specifically in vivo in a mammal to claudin-3 and/or claudin-4. The portion of native CPE responsible for toxicity is thought to be approximately residues 45-116 of full-length native CPE (SEQ ID NO:1). The portion of native CPE responsible for binding to claudin-3 and claudin-4 is residues 290-319 of SEQ ID NO:1 or a portion thereof (23-27).

The term "chemotherapy-resistant" cancer cells refers to cells of a tumor that has recurred after chemotherapy, not responded to chemotherapy, has demonstrated survival in vitro or in vivo after exposure to doses of one or more chemotherapy agents that would otherwise be considered for use against the tumor, or is of a type of tumor (such as USPC) that, based on data from experimental animals or other patients, is considered to not respond to chemotherapy or recur after chemotherapy.

The term "metastasized" or "metastatic" refers to cancer cells that have spread to a different part of the body from the site where the primary tumor for the cancer originated.

The term "therapeutic index" is defined herein as the ratio of the minimal toxic dose ($LD_{50}$) to the minimal dose that induces a measurable response in vivo, such as arresting tumor growth.

The term "cytotoxic agent" refers to an agent that kills cancerous cells in vitro or in vivo in a mammal. The term "cytotoxic agent" includes agents that are not toxic in the absence of immune system components but that promote an immune response that kills cancerous cells in vivo.

The term "Fc" refers to the constant portion of an immunoglobulin protein.

The terms "pancreatic cancer," "ovarian cancer," "uterine cancer," etc. refer to the organ or tissue type in which the primary tumor of the cancer originated.

Description:

CPE is an enterotoxin responsible for many cases of food poisoning Native CPE is a 319 residue protein (SEQ ID NO:1) that binds specifically to claudin-3 and claudin-4 on the surface of certain cells in the gastrointestinal tract. After CPE binds to its target cell receptor (claudin-3 or claudin-4) a 90 kDa small membrane complex is formed in the target cell plasma membrane containing intact CPE. Additional target cell proteins then associate with the small complex to form a large 160 kDa membrane complex that allows partial insertion of CPE into the membrane, allowing small molecule permeability changes and lysis (21, 22).

Functional domain mapping of the full-length 319 amino acid CPE protein showed that a CPE(290-319) COOH-terminus fragment is sufficient for high affinity binding to receptors and small complex formation, but does not initiate large complex formation and cytolysis. In fact, CPE(290-319) fragment inhibits cytolysis by full-length CPE (26). Deletion from full-length native CPE of the five residues at the C-terminus, residues 315-319, is enough to abolish binding to the receptors (25). Approximately residues 45-116 of CPE are essential for large complex formation and cytolysis. With NH2-terminal residues 1-44 deleted, CPE (45-319) is actually more toxic than full-length CPE (23-27).

Thus, in particular embodiments of the invention, the CPE is a variant CPE comprising residues 45-319 of SEQ ID NO:1. In other particular embodiments, the CPE comprises a sequence at least 80% identical, or at least 90% identical to residues 45-319 of SEQ ID NO:1.

In particular embodiments of the invention, the CPE comprises residues 290-319 of SEQ ID NO:1. In particular embodiments, the CPE comprises a fragment of residues 290-319 of SEQ ID NO:1 that binds specifically to claudin-3 and/or claudin-4. In particular embodiments, the CPE comprises residues 315-319 of SEQ ID NO: 1. In particular embodiments, CPE comprises a variant of residues 290-319 of SEQ ID NO:1 that specifically binds claudin-3 and claudin-4. In particular embodiments, CPE comprises a variant of residues 290-319 of SEQ ID NO:1 that specifically binds claudin-3 or claudin-4.

In particular embodiments, the CPE binds claudin-3 and/or claudin-4 with a $K_D$ of less than 10:M, or more preferably less than about 1:M, most preferably less than about 0.1:M. This can be assayed as described in references 14 and 26.

One embodiment of the invention is a method of treating ovarian cancer or uterine cancer in a mammal involving administering a therapeutically effective amount of CPE or a pharmaceutically acceptable salt thereof.

In a specific embodiment, the cancer includes chemotherapy-resistant malignant cells. As shown below, chemotherapy-resistant ovarian cancer cells have higher expression of claudin-3 and -4 than chemotherapy-naive ovarian cancer cells. USPC, a chemotherapy-resistant and aggressive form of uterine cancer also is shown below to have high expression of claudin-3 and -4. Thus, CPE is particularly suited for treatment of ovarian and uterine cancer. Moreover, since CPE is a toxin, oncologists may be hesitant to use it on a tumor that is thought to be sensitive to less toxic conventional chemotherapy agents.

In another particular embodiment of the method, the cancer includes metastatic malignant cells. It is shown below in Example 3 that metastatic ovarian tumors express higher levels of claudin-3 and -4 than primary ovarian tumors. USPC, an aggressive form of uterine cancer that tends to readily metastasize also is shown below to have high expression of claudin-3 and -4.

In a particular embodiment, the cancer is uterine serous papillary carcinoma (USPC).

In a particular embodiment, the cancer is ovarian serous papillary carcinoma (OSPC).

In a particular embodiment of the method, the CPE or pharmaceutically acceptable salt thereof is administered intraperitoneally.

The dosage of CPE or a pharmaceutically acceptable salt thereof for intraperitoneal administration is 0.2 to 0.8 mg/kg body mass, in a particular embodiment.

In other particular embodiments, the CPE or pharmaceutically acceptable salt thereof is administered intravenously or intratumorally.

In particular embodiments, the CPE or pharmaceutically acceptable salt thereof has a therapeutic index as administered of at least 5. The therapeutic index can depend on the route of administration. Thus, for tumors located in or adjacent to the peritoneal cavity, intraperitoneal administration is likely to have a higher therapeutic index than systemic intravenous administration. The therapeutic index will also depend on the type of cancer. The therapeutic index for treatment of a human is determined by data with experimental animals from the closest animal model of the particular type of cancer involved, or from data on treatment of humans when available. The therapeutic index is defined as the minimal toxic dose (e.g., the lethal dose for 50% of experimental animals) divided by the minimal effective dose (e.g., the minimal dose required to cause measurable tumor shrinkage in 50% of experimental animals).

In other particular embodiments, the CPE or pharmaceutically acceptable salt thereof has a therapeutic index as administered of at least 2.

In other particular embodiments, the CPE or pharmaceutically acceptable salt thereof has a therapeutic index as administered of at least 4, at least 6, at least 8, at least 10, or at least 20.

In some embodiments, the CPE consists of SEQ ID NO:1.

In some embodiments, the CPE is a mutant or engineered CPE. In particular embodiments, the mutant or engineered CPE comprises residues 45-116 of SEQ ID NO:1.

In some embodiments of the methods of the invention, the method involves administering a protective agent that protects cells against CPE toxicity.

A peptide consisting of residues 290-319 of CPE SEQ ID NO:1 has been shown to compete with native CPE for binding to cells and thus inhibit CPE binding (26). Any CPE fragment that includes residues 290-319 and does not include residues 45-116 is expected to be protective. Such a fragment will bind to the CPE receptors (claudin-3 and -4) but not lyse the cells, and will compete with full-length CPE for binding to the receptor (23-27). Fragments of residues 290-319 of SEQ ID NO:1 are also envisioned. In specific embodiments, the fragment includes residues 315-319 of SEQ ID NO:1.

Thus, one protective agent that protects cells against CPE toxicity is a protective agent that comprises residues 290-319 of native CPE, or a homologue thereof.

A protective agent that comprises residues 290-319 of native CPE, or a homologue thereof, is a proteinaceous agent that binds to claudin-3 and/or claudin-4 and does not lyse the cells it binds to. In particular embodiments, the homologue of residues 290-319 of native CPE is at least 80% or at least 90% identical to residues 290-319 of SEQ ID NO:1.

Another embodiment of a protective agent is a protective agent that comprises a fragment of residues 290-319 of SEQ ID NO:1 that binds specifically to claudin-3 and/or claudin-4.

The protective agent can also be an antibody against claudin-3 and/or claudin-4 that inhibits binding of CPE to claudin-3 and/or claudin-4. The term an "antibody against claudin-3 and/or claudin-4" refers to an antibody that specifically binds claudin-3 (i.e., binds claudin-3 and does not bind other proteins in a mammal), specifically binds claudin-4, or specifically binds to both claudin-3 and claudin-4.

The protective agent that is an antibody against claudin-3 and/or claudin-4 can be an antibody comprising an Fc region coupled to a peptide comprising residues 290-319 of SEQ ID NO:1 or a fragment thereof that specifically binds claudin-3 and/or claudin-4.

In particular embodiments, the protective agent is administered intravenously and the CPE or pharmaceutically acceptable salt thereof is administered by a non-intravenous route. For instance, the CPE or salt thereof may be administered intraperitoneally and the protective agent administered intravenously.

In particular embodiments, the protective agent is administered enterally. The CPE or salt thereof may be administered in conjunction with this, e.g., intraperitoneally or intravenously.

In particular embodiments, the protective agent is a non-toxic agent that inhibits CPE binding to claudin-3 and/or claudin-4. The inhibition may be competitive or non-competitive. Preferably the inhibition is competitive.

One embodiment of the invention is a method of treating cancer in a mammal involving intraperitoneally administering to the mammal a therapeutically effective amount of CPE or a pharmaceutically acceptable salt thereof, wherein at least some cancerous cells are located in or adjacent to the peritoneal cavity of the mammal, and the cells are sensitive to CPE. The cancerous cells are considered "adjacent to the peritoneal cavity" of the mammal if intraperitoneal administration of CPE results in a higher therapeutic index (the ratio of the toxic dose to the effective dose) than systemic intravenous administration of CPE. Cancerous cells may also be considered adjacent to the peritoneal cavity if intraperitoneal administration of CPE results in a higher concentration of CPE in the cancerous cells than systemic intravenous administration of CPE.

In a particular embodiment, all detectable cancerous cells are in or adjacent to the peritoneal cavity.

In particular embodiments of the method involving intraperitoneal administration of CPE, the cancerous cells include chemotherapy-resistant cells.

In particular embodiments, the cancerous cells include metastatic cancerous cells.

In particular embodiments, the cancer treated with intraperitoneal administration of CPE is pancreatic cancer. In other embodiments, the cancer is ovarian cancer or uterine cancer.

In particular embodiments, the cancer is uterine serous papillary carcinoma (USPC).

In another particular embodiment, the cancer is ovarian serous papillary carcinoma (OSPC).

In particular embodiments, the cancer is liver cancer, stomach cancer, colon cancer, bladder cancer, kidney cancer, intestinal cancer, testicular cancer, or prostate cancer, wherein cells of the cancer have claudin-3 and/or claudin-4.

The method involving intraperitoneal administration of CPE may involve in addition administering intravenously or enterally a protective agent that protects cells against CPE toxicity. This will provide some protection to healthy non-target tissues.

One embodiment of the invention is a use of CPE to prepare a medicament effective to treat ovarian or uterine cancer in a mammal.

In a particular embodiment, the mammal is a human.

In a particular embodiment, the medicament is adapted for intraperitoneal administration to the mammal.

Another embodiment of the invention is a use of CPE to prepare a medicament effective to treat cancer in a mammal, wherein the medicament is adapted for intraperitoneal administration.

In particular embodiments of the use, the cancer is ovarian cancer, uterine cancer, or pancreatic cancer.

The invention also provides a method of determining the sensitivity of a gynecological malignancy to CPE involving detecting the presence or absence of claudin-3 and/or claudin-4 in a tissue sample comprising a portion of the malignancy.

In particular embodiments, the detecting step involves contacting the tissue sample with a protein containing residues 290-319 of SEQ ID NO:1. In specific embodiments, the protein is CPE. The CPE may be SEQ ID NO:1. In particular embodiments, the protein is an antibody comprising residues 290-319 of SEQ ID NO:1 or a fragment thereof that binds specifically to claudin-3 and/or claudin-4 (e.g., an antibody comprising an Fc coupled to an antigen-binding peptide comprising residues 290-319 of SEQ ID NO:1).

Binding of the protein can be detected in various ways. If the protein is CPE, lysis of the cells can be detected. If the protein is labeled with radioactivity, a fluorescent label, or some other label, the label can be detected. The protein can also include a tag that is recognized by an antibody, where binding of the protein is detected by adding antibody after adding the protein, and detecting binding of the antibody to the tissue sample.

The detecting step can involve detecting lysis of cells.

The detecting step can involve contacting the tissue sample with an antibody against claudin-3 and/or an antibody against claudin-4.

In Example 1 below it is shown that the TROP-1/Ep-CAM gene is overexpressed, and the Ep-CAM protein is found, in ovarian serous papillary carcinoma cells. An anti-Ep-CAM antibody, edrecolomab, has been shown to increase survival in patients harboring stage III colon cancer expressing the Ep-CAM protein (28). Thus, one embodiment of the invention is a method of treating cancer in a mammal involving administering to the mammal a therapeutically effective amount of an anti-Ep-CAM antibody; wherein the cancer is ovarian cancer.

In particular embodiments, the ovarian cancer is OSPC.

In particular embodiments, the antibody is edrecolomab.

The antibody may be radioactive, in which case it can be used for radiation therapy of the cancer.

Another embodiment of the invention is a method of determining the sensitivity of a gynecological malignancy to treatment with an anti-Ep-CAM antibody involving detecting the presence or absence of Ep-CAM in a tissue sample comprising a portion of the malignancy.

The detecting step can include contacting the tissue sample with an antibody against Ep-CAM. The antibody can be polyclonal or monoclonal.

In particular embodiments, the malignancy is ovarian cancer, or specifically OSPC.

Another embodiment of the invention is a method of protecting a mammal from CPE toxicity involving administering a non-toxic protective agent that binds to claudin-3 and/or claudin-4 and inhibits CPE binding to claudin-3 and/or claudin-4. The protective agent can be administered before CPE is administered for treatment. Or the protective agent can be administered after CPE is administered, e.g., as an antidote to an overdose of therapeutic CPE, or as an antidote or treatment for CPE food poisoning.

The protective agent could be an antibody against claudin-3 and/or claudin-4, e.g., a humanized antibody.

The protective agent can also be an agent that comprises residues 290-319 of SEQ ID NO:1, or a homologue thereof, or can be an agent that comprises a fragment of residues 290-319 of SEQ ID NO:1 that binds specifically to claudin-3 and/or claudin-4.

Another embodiment of the invention provides a method of treating cancer in a mammal involving administering to the mammal an antibody against claudin-3 and/or claudin-4, wherein cancerous cells in the mammal contain claudin-3 and/or claudin-4. Preferably, the cancerous cells contain at least 5-times more claudin-3 and/or claudin-4 than normal cells of the same tissue type.

In certain embodiments, the antibody may inhibit CPE binding to claudin-3 and/or claudin-4. But to treat cancer, the antibody does not have to. It need only bind to the claudin-3 or claudin-4 and attract immune attack against the antibody-labeled cells.

The antibody may also carry a therapeutic radioisotope, so that it kills the claudin-3- or claudin-4-containing cells with radioactivity.

In particular embodiments, the cancer treated with antibodies is ovarian cancer (e.g., OSPC) or uterine cancer (e.g., USPC). In other embodiments, the cancer is pancreatic, prostate, or colon cancer. In other embodiments, the cancer is breast cancer or lung cancer.

Antibodies against claudin-3 and claudin-4 and Ep-CAM can be generated by injecting rabbits, mice, goats, or other appropriate vertebrate animals with whole claudin-3 or claudin-4 or Ep-CAM, or peptides from the proteins can be synthesized and coupled to a carrier protein for injection. Preferably, if peptides are used, extracellular domains of the proteins are selected, since these are the portions that will be exposed on the exterior of the cell. The amino acid sequences of human claudin-4 (referred to as human CPE receptor) and claudin-3 (referred to as RVP1) and hydrophobicity plots of the proteins, which suggest the transmembrane domains and the extracellular domains, are disclosed in references 15 and 50. This can be used to select peptides to be used to generate antibodies.

Polyclonal or monoclonal antibodies can be prepared from the immunized animal as described below. The antibodies used should recognize the exposed extracellular portions of claudin-3 and/or claudin-4 in order to bind to cells expressing the proteins. For this reason, monoclonal antibodies may be preferable, since they can be characterized as recognizing a specific epitope found on the outer surface of the cells expressing claudin-3 or claudin-4.

Antibodies obtained can be administered to experimental mammals at a dose of approximately 10 mg/kg every 3-7 days to treat cancer.

Antibodies can be labeled with radioisotopes, such as yttrium-90 or iodine-131 for therapeutic radiation treatment. One procedure for attaching radioisotopes to antibodies is described in reference 122. Radiolabelled antibodies are administered to experimental animals at appropriate radiation doses. For instance, yttrium-90 is administered to humans in the monoclonal antibody ZEVALIN™ for treatment of lymphoma at a dose of 5 mCi. Thus, in some embodiments of the antibodies used in the invention, the antibody carries a therapeutic radionuclide.

One embodiment of the invention is an antibody comprising an antigen-binding region comprising residues 290-319 of SEQ ID NO:1 or a fragment thereof that binds specifically to claudin-3 and/or claudin-4. This can be created by recombinant means as described in Example 4 below. Briefly, a recombinant DNA is engineered to express a fusion polypeptide comprising the CH2 and CH3 domains of the IgG1 heavy chain coupled to residues 290-319 of SEQ ID NO:1. Two heavy chains dimerize in vivo to form an Fc coupled to two peptides containing the residues of CPE that bind specifically to claudin-3 and claudin-4.

Thus, in particular embodiments, an antibody used in the invention is produced by recombinant means.

Other methods for the preparation of antibodies are described below.

Another embodiment of the invention provides a method of treating cancer in a mammal involving administering to the mammal a therapeutically effective amount of a cytotoxic agent that binds specifically to claudin-3 and/or claudin-4, wherein the cancer is uterine cancer or ovarian cancer.

The cytotoxic agent may be CPE or a pharmaceutically acceptable salt thereof.

The cytotoxic agent may also be an antibody that binds specifically to claudin-3 and/or claudin-4.

The cytotoxic agent may include residues 290-319 of SEQ ID NO:1 or a fragment thereof that binds specifically to claudin-3 and/or claudin-4; coupled to a cytotoxic moiety.

In particular embodiments, the cytotoxic moiety is an anti-cancer chemotherapy agent. An anti-cancer chemotherapeutic agent refers to an agent that kills or inhibits the growth of cancer cells while having less effect on non-cancerous cells, typically because it selectively kills dividing cells. Examples suitable for use in creating these cytotoxic agents include amsacrine, azacytidine, bleomycin, busulfan, capecitabine, carboplatin, carmustine, chlorambucil, cisplatin, cladribine, cyclophosphamide, cytarabine, dactinomycin, daunorubicin, decarbazine, docetaxel, doxorubicin, epirubicin, estramustine, etoposide, floxuridine, fludarabine, fluorouracil, gemcitabine, hexamethylmelamine, idarubicin, ifosfamide, irinotecan, lomustine, mechlorethamine, melphalan, mercaptopurine, methotrexate, mitomycin C, mitotane, mitoxantrone, oxaliplatin, paclitaxel, pemetrexed, pentostatin, plicamycin, procarbazine, raltitrexed, semustine, streptozocin, temozolamide, teniposide, thioguanine, thiotepa, topotecan, trimitrexate, valrubicin, vincristine, vinblastine, vindestine, or vinorelbine.

The chemotherapeutic agents can be coupled to the CPE peptide that binds claudin-3/claudin-4 as described in published international patent application PCT/US2004/034704.

In other embodiments, the cytotoxic moiety is a moiety that stimulates cell killing by immune system components, e.g., cell killing by the complement system or T-cells. In particular embodiments, the cytotoxic moiety is an antibody Fc. In other specific embodiments, the cytotoxic moiety is interleukin-2.

It has been shown that interleukin-2 (IL2) can be coupled to an antibody that recognizes an antigen on cancer cells, and the coupled moiety binds to target cells through the antibody portion of the conjugate (123). The interleukin-2 portion of the conjugate is recognized by T-cells, including T-cells that do not specifically recognize the tumor cells (123). The conjugates have been shown to thereby couple target tumor cells to noncognate T-cells (123). The conjugates also induce cell killing of the target tumor cells by T-cells, including T-cells that do not specifically recognize the target tumor cells in the absence of the antibody-IL2 conjugate (123).

Thus, here IL2 can be coupled to residues 290-319 of SEQ ID NO:1 or a fragment thereof that binds specifically to claudin-3 and/or claudin-4. The fusion protein will bind to cells carrying claudin-3 or claudin-4 receptors and induce killing of these cells by cytotoxic T lymphocytes through the T-cells' recognition of, binding to, and stimulation by the IL2 moiety.

In another embodiment of this method of treating cancer using a cytotoxic agent comprising residues 290-319 of SEQ ID NO:1 or a fragment thereof that specifically binds claudin-3 and/or claudin-4; coupled to a cytotoxic moiety, the cytotoxic moiety is a therapeutic radionuclide.

The methods described herein using agents other than CPE are, like the methods using CPE, suitable for treatment of ovarian cancer and uterine cancer. They are also suitable for treatment of ovarian, uterine, and other cancers wherein the cancer includes chemotherapy resistant cells or metastatic malignant cells, or wherein the cancer is a recurrent cancer.

Raising Antibodies

To generate antibodies, claudin-3 or claudin-4 or Ep-CAM can be administered directly to a mammal, or the proteins or peptide fragments thereof can be coupled to a carrier protein. Suitable carrier proteins include keyhole limpet hemocyanin, bovine serum albumin, and ovalbumin. Methods of coupling to the carrier protein include single step glutaraldehyde coupling and other methods disclosed in Harlow, Ed et al., *Antibodies: a laboratory manual*, Cold Spring Harbor Laboratory (1988).

The immunogen is used to immunize a vertebrate animal in order to induce the vertebrate to generate antibodies.

Preferably the immunogen is injected along with an adjuvant such as Freund's adjuvant, to enhance the immune response. Suitable vertebrates include rabbits, mice, rats, hamsters, goats, and chickens.

Hybridomas to synthesize monoclonal antibodies can be prepared by methods known in the art. See, for instance, Wang, H., et al., *Antibody Expression and Engineering*, Am. Chem. Soc., Washington, D.C. (1995). Polyclonal and monoclonal antibodies can be isolated by methods known in the art. See, for instance, id, and Harlow et al.

Native antibodies are tetramers of two identical light (L) chains and two identical heavy (H) chains. The L and H chains each have variable domains that are responsible for antigen recognition and binding. The variability in the variable domains is concentrated in the complementarity determining regions (CDRs).

An antibody that is contemplated for use in the present invention can be in any of a variety of forms, including a whole immunoglobulin, an antibody fragment such as Fv, Fab, and similar fragments, a single chain antibody that includes the CDR, and like forms, all of which fall under the broad term "antibody" as used herein.

The term "antibody fragment" refers to an antigen-binding portion of a full-length antibody. Antibody fragments can be as small as about 4 amino acids, about 10 amino acids, or about 30 amino acids or more. Some types of antibody fragments are the following:

(1) Fab is the fragment that contains a monovalent antigen-binding fragment of an antibody molecule. A Fab fragment can be produced by digestion of whole antibody with the enzyme papain to yield an intact light chain and a portion of one heavy chain. Two Fab fragments are obtained per whole antibody molecule.

(2) Fab' is the fragment of an antibody that can be obtained by treating whole antibody with pepsin, followed by reduction to yield an intact light chain and a portion of the heavy chain. Two Fab' fragments are obtained per whole antibody molecule. Fab' fragments differ from Fab fragments by the addition of a few residues at the carboxyl terminus of the heavy chain CH1 domain including one or more cysteines.

(3) F(ab')$_2$ is the fragment that can be obtained by digestion of whole antibody with pepsin, without reduction. F(ab')$_2$ is a dimer of two Fab' fragments held together by two disulfide bonds.

(4) Fv is the minimum antibody fragment that contains a complete antigen recognition and binding site. Fv consists of a dimer of one H and one L chain variable domain in a tight, non-covalent association ($V_H$-$V_L$ dimer). It is in this configuration that the three CDRs of each variable domain interact to define an antigen-binding site. Collectively, the six CDRs confer antigen binding specificity to the antibody. However, even a single variable domain (or half of an Fv comprising only three CDRs specific for an antigen) has the ability to bind antigen, although at a lower affinity than the complete binding site.

(5) A single chain antibody (SCA) is defined as a genetically engineered molecule containing the variable region of the light chain and the variable region of the heavy chain linked by a suitable polypeptide linker as a genetically fused single chain molecule.

The preparation of polyclonal antibodies is well known to those skilled in the art. See, for example, Coligan et al., in *Current Protocols in Immunology*, section 2.4.1 (1992). The preparation of monoclonal antibodies is likewise conventional. See, for example, Harlow et al., page 726.

Methods of in vitro and in vivo manipulation of monoclonal antibodies are well known to those skilled in the art. For example, the monoclonal antibodies to be used in accordance with the present invention may be made by the hybridoma method first described by Kohler and Milstein, *Nature* 256:495 (1975), or may be made by recombinant methods, e.g., as described in U.S. Pat. No. 4,816,567. The monoclonal antibodies for use with the present invention may also be isolated from phage antibody libraries using the techniques described in Clarkson et al., *Nature* 352:624 (1991), as well as in Marks et al., *J. Mol. Biol.* 222:581 (1991). Another method involves humanizing a monoclonal antibody by recombinant means to generate antibodies containing human specific and recognizable sequences. See, for review, Holmes et al., *J. Immunol.* 158:2192 (1997) and Vaswani et al., *Annals Allergy, Asthma & Immunol.* 81:105 (1998).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) are identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Nat'l. Acad. Sci.* 81:6851 (1984)).

Methods of making antibody fragments are also known in the art (see, for example, Harlow and Lane, *Antibodies: a Laboratory Manual*, Cold Spring Harbor Laboratory, New York (1988)). Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5 S Fab' monovalent fragments. Alternatively, an enzymatic cleavage using pepsin produces two monovalent Fab fragments and an Fc fragment directly. These methods are described, for example, in U.S. Pat. Nos. 4,036,945, and 4,331,647, and references contained therein.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be noncovalent or the variable chains can be linked by an intermolecular disulfide bond or cross-linked by chemicals such as glutaraldehyde. Preferably, the Fv fragments comprise $V_R$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker bridging the two V domains. Methods for producing sFvs are described, for example, by Whitlow et al., *Methods: a Companion to*

Methods in Enzymology, 2:97 (1991); Bird et al., Science 242:423 (1988); Ladner et al., U.S. Pat. No. 4,946,778; and Pack et al., Bio/Technology 11:1271 (1993).

Another form of an antibody fragment is a peptide containing a single complementarity-determining region (CDR). CDR peptides ("minimal recognition units") are often involved in antigen recognition and binding. CDR peptides can be obtained by cloning or constructing genes encoding the CDR of an antibody of interest. Such genes are prepared, for example, by using the polymerase chain reaction to synthesize the variable region from RNA of antibody-producing cells. See, for example, Larrick et al., Methods: a Companion to Methods in Enzymology, 2:106 (1991).

The invention contemplates human and humanized forms of non-human (e.g., murine) antibodies. Such humanized antibodies are chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity.

In some instances, Fv framework residues of the human immunoglobulin are replaced by corresponding non-human residues. Furthermore, humanized antibodies may comprise residues that are found neither in the recipient antibody nor in the imported CDR or framework sequences. These modifications are made to further refine and optimize antibody performance. In general, humanized antibodies will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details, see: Jones et al., Nature 321:522 (1986); Reichmann et al., Nature 332:323 (1988); Presta, Curr. Opinion Struct. Biol. 2:593 (1992); Holmes et al., J. Immunol. 158:2192 (1997); and Vaswani et al., Annals Allergy, Asthma & Immunol. 81:105 (1998).

Antibodies of the invention can also be mutated to optimize their affinity, selectivity, binding strength or other desirable property. One method of mutating antibodies involves affinity maturation using phage display. Affinity maturation using phage display refers to a process described in Lowman et al., Biochemistry 30:10832 (1991); see also Hawkins et al., J. Mol. Biol. 254:889 (1992).

The invention will now be illustrated by the following non-limiting examples.

EXAMPLES

The following materials and methods are common to the Examples.

Materials and Methods

RNA Purification and Microarray Hybridization and Analysis.

Detailed protocols for RNA purification, cDNA synthesis, cRNA preparation, and hybridization to the Affymetrix Human U95Av2 GeneChip microarray were performed according to the manufacturer's protocols, as reported previously (29).

Data Processing.

All data used in the analyses were derived from Affymetrix 5.0 software. GeneChip 5.0 output files are given as a signal that represents the difference between the intensities of the sequence-specific perfect match probe set and the mismatch probe set, or as a detection of present, marginal, or absent signals as determined by the GeneChip 5.0 algorithm. Gene arrays were scaled to an average signal of 1500 and then analyzed independently. Signal calls were transformed by the log base 2 and each sample was normalized to give a mean of 0 and variance of 1.

Gene Expression Data Analysis.

Statistical analyses of the data were performed with the software package SPSS 10.0 (SPSS, Chicago, Ill.). The first test applied was the detection. In each comparison, genes having "present" detection calls in more than half of the samples in the overexpressed gene group were retained. To compare gene expression levels, the nonparametric Wilcoxon rank sum (WRS) test ($p<0.05$) was applied to the normalized signal call. By combining the detection and WRS data, differentially expressed genes were identified between OSPC and NOVA or USPC and NEC.

Quantitative Real-Time PCR.

q-RT-PCR was performed with an ABI Prism 7000 Sequence Analyzer using the manufacturer's recommended protocol (Applied Biosystems, Foster City, Calif.) to validate differential expression of selected genes in samples from all primary cell lines (10 OSPC and 5 NOVA in Example 1; 10 USPC and 5 NEC in Example 2). Each reaction was run in triplicate. The comparative threshold cycle ($C_T$) method was used for the calculation of amplification fold as specified by the manufacturer. Briefly, five µg of total RNA from each sample was reverse transcribed using SUPERSCRIPT™ II Rnase H Reverse Transcriptase (Invitrogen, Carlsbad, Calif.). Ten µl of reverse transcribed RNA samples (from 500 µl of total volume) were amplified by using the TAQMAN™ Universal PCR Master Mix (Applied Biosystems) to produce PCR products specific for the target genes. Primers specific for 18s ribosomal RNA and empirically determined ratios of 18s competimers (Applied Biosystems) were used to control for the amounts of cDNA generated from each sample. Primers for TROP-1, claudin-3 and claudin-4 were obtained from Applied Biosystems as assay on demand products. Assays ID were Hs00158980_m1 (TROP-1), Hs00265816_s1 (claudin-3), and Hs00533616_s1 (claudin-4). CD24 primers sequences were the following (forward, 5'-cccaggtgttactgtaattcctcaa; reverse, 5'-gaacagcaatagctcaacaatgtaaac). Primers for L1CAM, claudin-3, and claudin-4 were obtained from Applied Biosystems as assay on demand products. Assays ID were Hs00170849_m1 (L1CAM), Hs00265816_s1 (claudin-3), and Hs00533616_s1 (claudin-4). GRB7 primer sequences were: forward, 5'-tctacgggatgaccactga-3'; reverse, 5'-cgaagcccctgtgtcca-3'c-erbB2 primer sequences were: forward, 5'-gtatacattcggcgccagct-3'; reverse, 5'-gcagac-gagggtgcagga-3'. CDKN2A/p16 primer sequences were: forward, 5'-cccaaacgcaccgaatagttac-3'; reverse, 5'-attccaat-tcccctgcaaact-3'. CDKN2A/p14ARF primer sequences were: forward, 5'-tgatgctactgaggagccagc-3'; reverse, 5'-agggcctttcctacctggtc-3'. Amplification was carried out by using 1 unit of polymerase in a final volume of 20 µl containing 2.5 mM $MgCl_2$. TAQGOLD™ was activated by incubation at 96° C. for 12 min, and the reactions were cycled 26-30 times at 95° C. for 1 min, 55° C. for 1 min, and 72° C. for 1 min, followed by a final extension at 72° C. for 10 min. PCR products were visualized on 2% agarose gels stained with ethidium bromide, and images were captured by an Ultraviolet Products Image Analysis System. Differences among OSPC and NOVA or USPC and NEC in the q-RT-PCR expression data were tested using the Kruskal-Wallis nonparametric test. Pearson product-moment correlations were used to estimate the degree of association between the microarray and q-RT-PCR data.

Claudin-4 Immunostaining of Formalin-Fixed Tumor Tissues.

Ovarian and uterine tumors were evaluated by immunohistochemical staining on formalin-fixed tumor tissue for claudin-4 surface expression. Study blocks were selected after histopathologic review by a surgical pathologist. The most representative hematoxylin and eosin-stained block sections were used for each specimen. Briefly, immunohistochemical stains were performed on 4 μm-thick sections of formalin-fixed, paraffin embedded tissue. After pretreatment with 10 mM citrate buffer at pH 6.0 using a steamer, they were incubated with mouse anti-claudin-4 antibodies (Zymed Laboratories Inc. San Francisco, Calif.) at 1:2000 dilution. Antigen-bound primary antibodies were detected using standard avidin-biotin immunoperoxidase complex (Dako Corp., Carpinteria, Calif.). Cases with less than 10% staining in tumor cells were considered negative for claudin expression, while positive cases were classified as follows regarding the intensity of claudin-4 protein expression: (a) +, focal membrane staining; (b) ++, diffuse membrane staining; and c) +++, diffuse membrane and cytoplasmic staining.

Example 1

Gene Expression Profiles in Primary Ovarian Serous Papillary Tumors and Normal Ovarian Epithelium: Identification of Candidate Molecular Markers for Ovarian Cancer Diagnosis and Therapy The goal of this study was to identify genes with differential patterns of expression between ovarian serous papillary carcinoma (OSPC) and normal ovarian (NOVA) epithelium and use this knowledge for the development of novel diagnostic and therapeutic markers for ovarian cancer. Gene expression in 10 primary OSPC cell lines, 2 establish OSPCT cell lines (UCI-101, UCI-107), and 5 primary NOVA epithelial cultures was analyzed by oligonucleotide microarrays with probe sets complementary to 12,533 genes.

Materials and Methods

Establishment of OSPC and NOVA Primary Cell Lines.

A total of fifteen primary cell lines (i.e., 10 OSPC and 5 NOVA) were established after sterile processing of the samples from surgical biopsies as previously described for ovarian carcinoma specimens (30,19,31). UCI-101 and UCI-107, two previously characterized OSPC cell lines (32,33) were also included in the analysis. All fresh tumor samples were obtained with appropriate consent according to IRB guidelines. Tumors were staged according to the F.I.G.O operative staging system. Radical tumor debulking, including a total abdominal hysterectomy and omentectomy, was performed in all ovarian carcinoma patients while normal ovarian tissue was obtained from consenting similar age donors undergoing surgery for benign pathology. No patient received chemotherapy before surgery. Patient characteristics are described in Table 1. Briefly, normal tissue was obtained by scraping epithelial cells from the ovarian surface and placing cells in RPMI 1640 medium (Sigma Chemical Co., St. Louis, Mo.) containing 10% fetal bovine serum (FBS, Invitrogen, Grand Island, N.Y.), 200 u/ml penicillin, and 200 μg/ml streptomycin. The epithelial explants were then allowed to attach and proliferate. Once the epithelial cells reached confluency, explants were trypsinized and subcultured for 3 to 4 passages before being collected for RNA extraction. Viable tumor tissue was mechanically minced in RPMI 1640 to portions no larger than 1-3 mm³ and washed twice with RPMI 1640. The portions of minced tumor were then placed into 250 ml flasks containing 30 ml of enzyme solution [0.14% collagenase Type I (Sigma, St. Louis, Mo.) and 0.01% DNAse (Sigma, 2000 KU/mg)] in RPMI 1640, and incubated on a magnetic stirring apparatus overnight at 4° C. Enzymatically dissociated tumor was then filtered through 150 μm nylon mesh to generate a single-cell suspension. The resultant cell suspension was then washed twice in RPMI 1640 plus 10% FBS. Primary cell lines were maintained in RPMI 1640, supplemented with 10% FBS, 200 u/ml penicillin, 200 μg/ml streptomycin at 37° C., 5% $CO_2$. The epithelial nature and the purity of OSPC and NOVA cultures was verified by immunohistochemical staining and flow cytometric analysis with antibodies against cytokeratin as previously described (30,31). Only primary cultures which had at least 90% viability and contained >99% epithelial cells were used for total RNA extraction.

Gene Cluster/Treeview.

The hierarchical clustering of average-linkage method with the centered correlation metric was used (34). The dendrogram was constructed with a subset of genes from 12,588 probe sets present on the microarray, whose expression levels varied the most among the 11 samples, and were thus most informative. For the hierarchical clustering shown in FIGS. 1 and 2, only genes significantly expressed and whose average change in expression level was at least five-fold were chosen. The expression value of each selected gene was re-normalized to have a mean of zero.

Flow Cytometry.

To validate microarray data on primary OSPC and NOVA cell lines at the protein level, TROP-1/EP-CAM and CD24 expression were evaluated by flow cytometric analysis of a total of 13 primary cell lines (i.e., 10 OSPC and 3 NOVA). Unconjugated anti-TROP-1/EP-CAM (IgG2a), anti-CD24 (IgG2a) and isotype control antibodies (mouse IgG2a) were all obtained from BD PharMingen (San Diego, Calif.). Goat anti-murine FITC-labeled mouse Ig was purchased from Becton Dickinson (San Jose, Calif.). Analysis was conducted with a FACScan, utilizing cell Quest software (Becton Dickinson).

TROP-1 and CD24 Immunostaining of Formalin-Fixed Tumor Tissues.

To evaluate whether the differential TROP-1 and CD24 expression detected by flow cytometry on primary OSPC cell lines were comparable to the expression of TROP-1 and CD24 of uncultured OSPC from which the primary cell lines were derived, protein expression was evaluated by standard immunohistochemical staining on formalin fixed tumor tissue from all surgical specimens (i.e., 10 OSPC and 5 NOVA controls). Study blocks were selected after histopathologic review by a surgical pathologist. The most representative hematoxylin and eosin-stained block sections were used for each specimen. Briefly, immunohistochemical stains were performed on 4 μm-thick sections of formalin-fixed, paraffin embedded tissue. After pretreatment with 10 mM citrate buffer at pH 6.0 using a steamer, they were incubated with anti-Ep-CAM Ab-3 MAb and anti-CD24 (Neo Markers, Fremont, Calif.) at 1:2000 dilution. Slides were subsequently labeled with streptavidin-biotin (DAKO, Glostrup, Denmark), stained with diaminobenzidine and counterstained with hematoxylin. The intensity of staining was graded as 0 (staining not greater than negative control), 1+(light staining), 2+(moderate staining), or 3+(heavy staining).

Results

Characteristics of the Patients.

The characteristics of the patients from whom the 10 primary OSPC cell lines were derived are listed in Table 1.

TABLE 1

| Patient | Age | Grade | Stage | Presence of Ascites | Chemotherapy Regimen | Response to Therapy |
|---|---|---|---|---|---|---|
| OSPC 1 | 42 | G2/3 | IV A | yes | TAX + CARB | Complete response |
| OSPC 2 | 67 | G3 | III B | yes | TAX + CARB | Complete response |
| OSPC 3 | 61 | G3 | III C | no | TAX + CARB | Partial response |
| OSPC 4 | 60 | G3 | III C | no | TAX + CARB | Complete response |
| OSPC 5 | 59 | G2/3 | III C | yes | TAX + CARB | Complete response |
| OSPC 6 | 72 | G3 | IV A | yes | TAX + CARB | Stable disease |
| OSPC 7 | 63 | G3 | III C | yes | TAX + CARB | Progressive Disease |
| OSPC 8 | 74 | G2/3 | III C | no | TAX + CARB | Partial response |
| OSPC 9 | 68 | G3 | III B | yes | TAX + CARB | Complete response |
| OSPC 10 | 77 | G2/3 | III C | no | TAX + CARB | Complete response |

Gene Expression Profiles Distinguish OSPC from NOVA and Identify Differentially Expressed Genes.

Flash frozen biopsies from ovarian tumor tissue are known to contain significant numbers of contaminant stromal cells as well as a variety of host derived immune cells (e.g., monocytes, dendritic cells, lymphocytes). In addition, because ovarian epithelial cells represent a small proportion of the total cells found in the normal ovary, it is difficult to collect primary material that is free of contaminating ovarian stromal cells in sufficient quantities to conduct comparative gene expression analyses. However, ovarian epithelial cells can be isolated and expanded in culture for about 15 passages (30,19) while the majority of primary ovarian carcinomas can be expanded in vitro for several passages (31). Thus, short term primary OSPC and NOVA cell cultures, minimizing the risk of a selection bias inherent in any long term in vitro growth, may provide an opportunity to study differential gene expression between relatively pure populations of normal and tumor-derived epithelial cells. Accordingly, comprehensive gene expression profiles of 10 primary OSPC and 5 primary NOVA cell lines were generated using high-density oligonucleotide arrays with 12,533 probe sets, which in total interrogated some 10,000 genes. In addition, gene expression profiles derived from two established and previously characterized OSPC cell lines (i.e., UCI-101 and UCI-107) were also analyzed. By combining the detection levels of genes significantly expressed in primary and established OSPC cultures very little correlation between the two groups of OSPC was found. Indeed, as shown in FIG. 1, UCI-101 and UCI-107 established cell lines grouped together in the leftmost columns of the dendrogram while all ten primary OSPC clustered tightly together in the rightmost columns separately by the 5 NOVA controls. Because of these results the analysis was focused on the detection of differentially expressed genes between the two homogeneous groups of primary OSPC and NOVA cell lines. Using the nonparametric WRS test ($p<0.05$) that readily distinguished between the two groups of primary cultures, 1,518 genes differentially expressed between OSPC and NOVA were found. The cluster analysis was based on hybridization intensity values for each cell line for 299 gene segments whose average change in expression level was at least five-fold (data not shown). All 10 OSPC were grouped together. Similarly, all 5 NOVA were found to cluster tightly together. The tight clustering of OSPC from NOVA was "driven" by two distinct profiles of gene expression. The first was represented by a group of 129 genes that were highly expressed in OSPC and underexpressed in NOVA (Table 2). Many genes shown previously to be involved in ovarian carcinogenesis are present on these lists, providing some validity to the array analysis, while others are novel in ovarian carcinogenesis. Included in the genes overexpressed in OSPC are laminin, claudin-3 (CLDN3) and claudin-4 (CLDN4), tumor-associated calcium signal transducer 1 and 2 (TROP-1/Ep-CAM; TROP-2), ladinin 1, S100A2, SERP1N2 (PAI-2), CD24, lipocalin 2, osteopontin, kallikrein 6 (protease M) and kallikrein 10, matriptase (TADG-15) and stratifin (Table 2). Importantly, TROP-1/Ep-CAM gene encoding for a transmembrane glycoprotein previously found to be overexpressed in various carcinoma types including colorectal and breast (35) and where antibody-directed therapy has resulted in improved survival of patients (28), was 39-fold differentially expressed in OSPC when compared to NOVA (Table 2). The second profile was represented by 170 genes that were highly expressed in NOVA and underexpressed in OSPC (data not shown). Included in this latter group of genes are transforming growth factor beta receptor III, platelet-derived growth factor receptor alpha, SEMACAP3, ras homolog gene family, member I (ARHI), thrombospondin 2 and disabled-2/differentially expressed in ovarian carcinoma 2 (Dab2/DOC2).

TABLE 2

Upregulated genes expressed at least 5 fold higher in OSPC compared with NOVA

| Probe Set | Gene Symbol | Score(d)(SAM) | p of WRS | Ratio Ova/Nova |
|---|---|---|---|---|
| 35280_at | LAMC2 | 1.68927386 | 0.006 | 46.45 |
| 35276_at | CLDN4 | 1.734410451 | 0.015 | 43.76 |
| 33904_at | CLDN3 | 1.650076713 | 0.02 | 40.24 |
| 575_s_at | TACSTD1 | 1.705816336 | 0.02 | 39.36 |
| 32154_at | TFAP2A | 1.667038647 | 0.002 | 33.31 |
| 39015_f_at | KRT6E | 1.062629117 | 0.047 | 28.02 |
| 1713_s_at | CDKN2A | 1.137682905 | 0.015 | 26.96 |
| 41376_i_at | UGT2B7 | 0.939735032 | 0.047 | 24.81 |
| 38551_at | L1CAM | 1.151935363 | 0.008 | 24.66 |
| 291_s_at | TACSTD2 | 1.249487388 | 0.047 | 24.46 |
| 33282_at | LAD1 | 1.422481563 | 0.006 | 24.31 |
| 34213_at | KIBRA | 1.533570321 | 0.002 | 23.06 |
| 38489_at | HBP17 | 1.522882814 | 0.004 | 22.54 |
| 36869_at | PAX8 | 1.43906836 | 0.004 | 22.20 |
| 38482_at | CLDN7 | 1.307716566 | 0.027 | 20.01 |
| 37909_at | LAMA3 | 1.121654521 | 0.027 | 19.24 |
| 34674_at | S100A1 | 1.219106334 | 0.008 | 19.01 |
| 1620_at | CDH6 | 0.908193479 | 0.036 | 18.69 |
| 32821_at | LCN2 | 1.99990601 | 0.008 | 18.13 |
| 522_s_at | FOLR3 | 1.113781518 | 0.02 | 17.90 |
| 39660_at | DEFB1 | 0.837612681 | 0.036 | 17.34 |
| 2011_s_at | BIK | 1.594057668 | 0.006 | 17.23 |
| 41587_g_at | FGF18 | 0.965726983 | 0.02 | 17.10 |
| 36929_at | LAMB3 | 1.115590892 | 0.047 | 16.76 |
| 35726_at | S100A2 | 1.036576352 | 0.004 | 15.05 |
| 1887_g_at | WNT7A | 1.186990893 | 0.004 | 14.75 |
| 35879_at | GAL | 1.223278825 | 0.002 | 14.65 |
| 266_s_at | CD24 | 1.756569076 | 0.004 | 14.45 |
| 1108_s_at | EPHA1 | 1.242309171 | 0.006 | 14.36 |

TABLE 2-continued

Upregulated genes expressed at least 5 fold higher in OSPC compared with NOVA

| Probe Set | Gene Symbol | Score(d)(SAM) | p of WRS | Ratio Ova/Nova |
|---|---|---|---|---|
| 37483_at | HDAC9 | 1.406744957 | 0.006 | 14.28 |
| 31887_at | — | 1.311220827 | 0.011 | 13.68 |
| 1788_s_at | DUSP4 | 1.22421987 | 0.003 | 13.65 |
| 32787_at | ERBB3 | 0.996784565 | 0.02 | 13.21 |
| 41660_at | CELSR1 | 1.634286803 | 0.004 | 13.11 |
| 33483_at | NMU | 1.100849065 | 0.004 | 13.04 |
| 31792_at | ANXA3 | 0.896090153 | 0.011 | 12.90 |
| 36838_at | KLK10 | 1.026306829 | 0.02 | 12.71 |
| 1585_at | ERBB3 | 1.102058608 | 0.011 | 12.51 |
| 1898_at | TRIM29 | 1.071987353 | 0.002 | 12.44 |
| 37185_at | SERPINB2 | 0.815945986 | 0.027 | 12.26 |
| 406_at | ITGB4 | 1.296194559 | 0.006 | 11.66 |
| 1914_at | CCNA1 | 0.936342778 | 0.011 | 11.21 |
| 977_s_at | CDH1 | 0.93637461 | 0.036 | 11.19 |
| 37603_at | IL1RN | 1.103624942 | 0.015 | 11.14 |
| 35977_at | DKK1 | 1.123240701 | 0.006 | 10.74 |
| 36133_at | DSP | 1.280269127 | 0.002 | 10.69 |
| 36133_s_at | TNNT1 | 1.269558595 | 0.002 | 10.19 |
| 1802_s_at | ERBB2 | 0.787465706 | 0.006 | 9.61 |
| 2092_s_at | SPP1 | 1.34315986 | 0.02 | 9.53 |
| 35699_at | BUB1B | 1.026388835 | 0.006 | 9.49 |
| 37554_at | KLK6 | 0.895036336 | 0.027 | 9.45 |
| 38515_at | BMP7 | 0.945367 | 0.027 | 9.32 |
| 34775_at | TSPAN-1 | 1.001195829 | 0.02 | 9.01 |
| 37558_at | IMP-3 | 1.023799379 | 0.011 | 8.99 |
| 38324_at | LISCH7 | 1.308000521 | 0.006 | 8.96 |
| 39610_at | HOXB2 | 1.355268631 | 0.006 | 8.64 |
| 572_at | TTK | 1.122796615 | 0.006 | 8.53 |
| 1970_s_at | FGFR2 | 1.022708001 | 0.02 | 8.30 |
| 160025_at | TGFA | 1.065272755 | 0.015 | 8.28 |
| 41812_s_at | NUP210 | 1.392787031 | 0.006 | 8.26 |
| 34282_at | NFE2L3 | 1.165273649 | 0.008 | 8.06 |
| 2017_s_at | CCND1 | 1.114984456 | 0.002 | 8.04 |
| 33323_r_at | SFN | 1.202433185 | 0.008 | 8.01 |
| 38766_at | SRCAP | 1.131917941 | 0.008 | 7.99 |
| 41060_at | CCNE1 | 1.151246634 | 0.006 | 7.97 |
| 39016_r_at | KRT6E | 0.973486831 | 0.008 | 7.91 |
| 31610_at | MAP17 | 1.0156502 | 0.027 | 7.81 |
| 2027_at | S100A2 | 0.941919001 | 0.008 | 7.76 |
| 418_at | MKI67 | 0.826426448 | 0.011 | 7.46 |
| 1536_at | CDC6 | 1.08868941 | 0.017 | 7.37 |
| 634_at | PRSS8 | 0.899891713 | 0.02 | 7.30 |
| 34342_s_at | SPP1 | 1.318723271 | 0.02 | 7.27 |
| 182_at | ITPR3 | 1.107167336 | 0.006 | 7.27 |
| 32382_at | UPK1B | 0.731294678 | 0.047 | 7.16 |
| 863_g_at | SERPINB5 | 0.783530451 | 0.015 | 7.14 |
| 904_s_at | TOP2A | 0.971648429 | 0.02 | 7.12 |
| 40095_at | CA2 | 0.798857154 | 0.027 | 7.02 |
| 41294_at | KRT7 | 1.082553892 | 0.011 | 7.00 |
| 39951_at | PLS1 | 0.995091449 | 0.006 | 6.94 |
| 38051_at | MAL | 0.819842532 | 0.036 | 6.82 |
| 40726_at | KIF11 | 0.803689697 | 0.036 | 6.78 |
| 1148_s_at | — | 0.683569558 | 0.047 | 6.72 |
| 37920_at | PITX1 | 0.996497645 | 0.015 | 6.67 |
| 37117_at | ARHGAP8 | 1.129131077 | 0.002 | 6.65 |
| 38881_i_at | TRIM16 | 0.721698355 | 0.047 | 6.59 |
| 34251_at | HOXB5 | 1.219463307 | 0.002 | 6.52 |
| 41359_at | PKP3 | 1.047269618 | 0.004 | 6.50 |
| 40145_at | TOP2A | 0.961173129 | 0.02 | 6.48 |
| 37534_at | CXADR | 0.888147605 | 0.006 | 6.32 |
| 40303_at | TFAP2C | 0.948734146 | 0.004 | 6.30 |
| 31805_at | FGFR3 | 0.969764101 | 0.011 | 6.28 |
| 33245_at | MAPK13 | 0.877514586 | 0.011 | 6.27 |
| 885_g_at | ITGA3 | 0.702747685 | 0.036 | 6.19 |
| 34693_at | STHM | 0.872525584 | 0.008 | 6.15 |
| 38555_at | DUSP10 | 0.880305317 | 0.008 | 6.12 |
| 38418_at | CCND1 | 1.071102249 | 0.002 | 5.97 |
| 33730_at | RAI3 | 0.813298748 | 0.011 | 5.90 |
| 39109_at | TPX2 | 1.040973216 | 0.011 | 5.87 |
| 36658_at | DHCR24 | 1.122129795 | 0.004 | 5.81 |
| 35281_at | LAMC2 | 0.747766326 | 0.047 | 5.78 |
| 38749_at | MGC29643 | 0.683275086 | 0.036 | 5.77 |
| 1083_s_at | MUC1 | 0.746980491 | 0.027 | 5.75 |
| 40079_at | RAI3 | 0.709840659 | 0.02 | 5.73 |
| 2047_s_at | JUP | 0.815282235 | 0.011 | 5.62 |
| 32275_at | SLP1 | 0.940625784 | 0.02 | 5.61 |
| 2020_at | CCND1 | 0.926408163 | 0.002 | 5.51 |
| 33324_s_at | CDC2 | 1.026683994 | 0.008 | 5.47 |
| 36863_at | HMMR | 0.96343264 | 0.006 | 5.46 |
| 1657_at | PTPRR | 0.764510362 | 0.02 | 5.41 |
| 37985_at | LMNB1 | 0.895475347 | 0.008 | 5.36 |
| 36497_at | C14orf78 | 0.942921564 | 0.008 | 5.33 |
| 2021_s_at | CCNE1 | 0.893228297 | 0.006 | 5.33 |
| 37890_at | CD47 | 0.775908217 | 0.015 | 5.33 |
| 40799_at | C16orf34 | 0.852774782 | 0.008 | 5.30 |
| 35309_at | ST14 | 0.852534105 | 0.008 | 5.30 |
| 1599_at | CDKN3 | 0.925527261 | 0.02 | 5.29 |
| 981_at | MCM4 | 1.058558782 | 0.006 | 5.28 |
| 32715_at | VAMP8 | 0.938171642 | 0.006 | 5.28 |
| 38631_at | TNFAIP2 | 0.72369235 | 0.015 | 5.26 |
| 34715_at | FOXM1 | 1.31035831 | 0.008 | 5.24 |
| 33448_at | SPINT1 | 0.924028022 | 0.015 | 5.21 |
| 419_at | MKI67 | 0.938133197 | 0.015 | 5.16 |
| 1651_at | UBE2C | 1.436239741 | 0.008 | 5.14 |
| 35769_at | GPR56 | 0.937347548 | 0.015 | 5.08 |
| 37310_at | PLAU | 0.885110741 | 0.036 | 5.08 |
| 36761_at | ZNF339 | 0.937123503 | 0.011 | 5.05 |
| 37343_at | ITPR3 | 1.001079303 | 0.003 | 5.05 |
| 40425_at | EFNA1 | 0.813414458 | 0.047 | 5.04 |
| 1803_at | CDC2 | 0.732852195 | 0.027 | 5.00 |

Validation of the Microarray Data.

Quantitative RT-PCR assays were used to validate the microarray data. Four highly differentially expressed genes between OSPC and NOVA (i.e., TROP-1, CD24, Claudin-3 and Claudin-4) were selected for q-RT-PCR analysis. A comparison of the microarray and q-RT-PCR data for these genes is shown in FIG. 2. Expression differences between OSPC and NOVA for TROP-1, (p=0.002), CD24 (p=0.03), claudin-3 (p=0.002) claudin-4 (p=0.001) were readily apparent (Table 2 and FIG. 2). Moreover, for all four genes tested, the q-RT-PCR data were highly correlated to the microarray data (p<0.001) (r=0.90, 0.82. 0.80 and 0.75, respectively), as estimated from the samples (i.e., 10 OSPC and 5 NOVA) included in both the q-RT-PCR and microarray experiments. The q-RT-PCR data mirror the microarray data, both qualitatively and quantitatively, and suggest that most array probe sets are likely to accurately measure the levels of the intended transcript within a complex mixture of transcripts.

TROP-1 and CD24 Expression by Flow Cytometry on Primary OSPC and NOVA Cell Lines.

An important issue is whether differences in gene expression result in meaningful differences in protein expression. Because TROP-1/Ep-CAM gene encodes the target for the anti-Ep-CAM antibody (17-1A) Edrecolomab (Panorex) that has previously been shown to increase survival in patients harboring stage III colon cancer (28), expression of Ep-CAM protein by FACS analysis was analyzed on 13 primary cell lines (i.e., 10 OSPC and 3 NOVA). As positive controls, breast cancer cell lines (i.e., BT-474 and SK-BR-3, American Type Culture Collection) known to overexpress TROP-1/Ep-CAM were also studied. High TROP-1/Ep-CAM expression was found on all three primary OSPC cell lines tested (100% positive cells for all three OSPC), with mean fluorescence intensity (MFI) ranging from 116 to 280 (FIG. 3). In contrast, primary NOVA cell lines were negative for TROP-1/Ep-CAM surface expression (p<0.001) (FIG. 3). Similarly, CD24 expression was found on all three primary OSPC cell lines tested (100% positive cells for all three OSPC), with mean fluorescence intensity (MFI) ranging from 26 to 55 (FIG. 3). In contrast, primary NOVA cell lines were negative for CD24 surface expression (p<0.005) (FIG. 3). These results show that high expression of the TROP-1/Ep-CAM and CD24 gene products by OSPC correlate tightly with high protein expression by the tumor cells. Breast cancer positive controls were found to express high levels of TROP-1/Ep-CAM (data not shown).

TROP-1/Ep-CAM and CD24 Expression by Immunohistology on OSPC and NOVA Tissue Blocks.

To determine whether the high (OSPC) or low (NOVA) expression of the genes and Ep-CAM and CD24 protein expression detected by microarray and flow cytometry, respectively, in primary cell lines is the result of a selection of a subpopulation of cancer cells present in the original tumor, or whether in vitro expansion conditions may have modified gene expression, immunohistochemical analysis of TROP-1/Ep-CAM and CD24 protein expression on formalin fixed tumor tissue from all uncultured primary surgical specimens of OSPC and NOVA was performed. Heavy apical membranous staining for CD24 protein expression was noted in all OSPC specimens that also overexpressed the CD24 gene and its gene product by microarray and flow cytometry, respectively. In contrast, negative or low (i.e., score 0 or 1+) staining was found in all NOVA samples tested by immunohistochemistry. Similarly, heavy membranous staining for TROP-1/Ep-CAM protein expression (i.e., score 3+) was noted in all OSPC specimens that also overexpressed the TROP-1/Ep-CAM gene and its gene product by microarray and flow cytometry, respectively. In contrast, negative or low (i.e., score 0 or 1+) staining was found in all NOVA samples tested by immunohistochemistry (data not shown).

Discussion

Because of the lack of an effective ovarian cancer screening program and the common development of chemotherapy resistant disease after an initial response to cytotoxic agents (e.g., a platinum based regimen), ovarian cancer remains the most lethal among the gynecologic malignancies. Thus, identification of novel ovarian tumor markers to be used for early detection of the disease as well as the development of effective therapy against chemotherapy resistant/recurrent ovarian cancer remains a high priority.

High-throughput technologies for assaying gene expression, such as high-density oligonucleotide and cDNA microarrays, may offer the potential to identify clinically relevant genes highly differentially expressed between ovarian tumors and normal control ovarian epithelial cells (19, 30,36,37,38,39,40,41). This report represents the communication of an investigation involving the genome-wide examination of differences in gene expression between primary OSPC and normal ovarian epithelial cells (NOVA). In this study short-term primary OSPC and NOVA cultures were used (to minimize the risk of a selection bias inherent in any long term in vitro growth) to study differential gene expression in highly enriched populations of epithelial tumor cells. In this work, only the cancer cells derived from papillary serous histology tumors, which is the most common histological type of ovarian cancer, were included to limit the complexity of gene expression analysis.

It was found that hierarchical clustering of the samples and gene expression levels within the samples led to the unambiguous separation of OSPC from NOVA. Of interest, the expression patterns detected in primary OSPC cells were consistently different from those seen in established serous papillary ovarian carcinoma cell lines (i.e., UCI-101 and UCI-107). These data, thus, further highlight the divergence of gene expression that occurs as the result of long-term in vitro growth. Furthermore, these data emphasize that, although established ovarian cancer cell lines provide a relatively simple model to examine gene expression, primary OSPC and NOVA cultures represent a better model system of normal and cancerous ovarian tissues in comparative gene expression analysis. OVA 2, an OSPC with mixed clear cell features (i.e., a biologically aggressive variant of ovarian cancer characterized by a poor prognosis) clustered on a sub-branch with OSPC. Because of these results, the decision was made to focus the analysis on the detection of differentially expressed genes between the two homogeneous groups of primary OSPC and NOVA.

299 genes differentially expressed between OSPC and NOVA whose average change in expression level between the two groups was at least five-fold were detected. The known function of some of these genes may provide insights in the biology of serous ovarian tumors while others may prove to be useful diagnostic and therapeutic markers against OSPC. For example, laminin gamma 2 gene was found to be the most highly differentially expressed gene in OSPC with over 46-fold up-regulation relative to NOVA. Cell migration of ovarian epithelial cells is considered essential for cell dissemination and invasion of the submesothelial extracellular matrix commonly seen in ovarian cancer. Consistent with this view, the laminin gamma 2 isoform has been previously suggested to play an important role in tumor cell adhesion, migration, and scattering of ovarian carcinoma cells (42,43,44). Thus, it is likely that the high laminin expression found in ovarian tumor cells may be a marker correlated with the invasive potential of OSPC. Consistent with this view, increased cell surface expression of laminin has been reported in highly metastatic tumors cells compared to cells of low metastatic potential (45). Importantly, previous work has also shown that attachment and metastases of tumor cells can be inhibited by incubation with antilaminin antibodies (46), or synthetic laminin peptides (47), underscoring a novel potential approach for the treatment of chemotherapy resistant ovarian cancer.

TROP-1/Ep-CAM (also called 17-1A, ESA, EGP40) is a 40 kDa epithelial transmemebrane glycoprotein found overexpressed in several normal epithelia and in various carcinomas including colorectal and breast cancer (35). In most adult epithelial tissues, enhanced expression of Ep-CAM is closely associated with either benign or malignant proliferation. Among mammals, Ep-CAM is an evolutionarily highly conserved molecule (48), suggesting an important biologic function of this molecule in epithelial cells and tissue. In this regard, Ep-CAM is known to function as an intercellular adhesion molecule and could have a role in tumor metastasis (49). Because a randomized phase II trial with MAb CO17-1A in colorectal carcinoma patients has demonstrated a significant decrease in recurrence and mortality of MAb-treated patients versus control patients (28), TROP-1/Ep-CAM antigen has attracted substantial attention as a target for immunotherapy for treating human carcinomas. Importantly, in this work TROP-1/Ep-CAM was found 39-fold overexpressed in OSPC when compared to NOVA. These data provide support for the notion that anti-Ep-CAM antibody therapy can be a novel, and effective, treatment option for OSPC patients with residual/resistant disease after surgical and cytotoxic therapy. Protein expression data obtained by flow cytometry on primary OPSC cell lines and by immunohistochemistry on uncultured OSPC blocks support this view.

Claudin-3 and claudin-4, two members of claudin family of tight junction proteins, were two of the top five differentially expressed genes in OSPC. These results are consistent with a previous report on gene expression in ovarian cancer (19). Although the function of claudin proteins in ovarian cancer is still unclear, these proteins likely represents a transmembrane receptor (50). Claudin-3 and claudin-4 are low- and high-affinity receptors, respectively, for CPE and are sufficient to mediate CPE binding and trigger subsequent toxin-mediated cytolysis (51). These known functions of claudin-3 and claudin-4, combined with their extremely high level of expression in OSPC suggest the use of CPE as a novel therapeutic strategy for the treatment of chemotherapy resistant disease in ovarian cancer patients.

Plasminogen activator inhibitor-2 (PAI-2), a gene whose expression has been linked to cell invasion in several human malignancies (52,53), as well as to protection from tumor necrosis factor-α (TNF-α)-mediated apoptosis (54) was found 12-fold differentially expressed in OSPC when compared to NOVA. High PAI-2 levels are independently predictive of a poor disease-free survival (55). Interestingly, a 7-fold increase in PAI-2 content was found in the omentum of ovarian cancer patients compared to the primary disease suggesting that metastatic tumors may overexpress PAI-2 (55). Other studies, however, have identified PAI-2 production as a favorable prognostic factor in epithelial ovarian cancer (56). Indeed, high PAI-2 expression in invasive ovarian tumors was limited to a group of OSPC patients which experienced a more prolonged disease free and overall survival (56). The reasons for these differences are not clear, but, as previously suggested (57), may be related at least in part to the actions of macrophage colony stimulating factor-1 (CSF-1), a cytokine which has been shown to stimulate the release of PAI-2 by ovarian cancer cells.

CD24 is a small heavily glycosylated glycosylphosphatidylinositol-linked cell surface protein, which is expressed in hematological malignancies as well as in a large variety of solid tumors (58-62). However, it is only recently that CD24 overexpression has been reported at the RNA level in ovarian cancer (39). Consistent with this recent report, in the present study CD24 gene was found 14-fold differentially expressed in OSPC when compared to NOVA. Because CD24 is a ligand of P-selectin, an adhesion receptor on activated endothelial cells and platelets, its expression may contribute to the metastasizing capacities of CD24-expressing ovarian tumor cells (63-65). Importantly, CD24 expression has recently been reported as an independent prognostic marker for ovarian cancer patient survival (64). That data combined with the present findings further suggest that this marker may delineate aggressive ovarian cancer disease and may be targeted for therapeutic and/or diagnostic purposes.

Among the genes identified herein, lipocalin-2 has not been previously linked to ovarian cancer. Lipocalin-2 represents a particularly interesting marker because of several features. Lipocalins are extracellular carriers of lipophilic molecules such as retinoids, steroids, and fatty acid, all of which may play important roles in the regulation of epithelial cell growth (66,67). In addition, because lipocalin is a secreted protein, it may play a role in the regulation of cell proliferation and survival (66,67). Of interest, two recent publications on gene expression profiling of breast and pancreatic cancer have proposed lipocalin-2 as a novel therapeutic and diagnostic marker for prevention and treatment of these diseases (66,67). On the basis of the present findings, lipocalin-2 may be added to the known markers for ovarian cancer.

Osteopontin (SPP1) is an acidic, calcium-binding glycophosphoprotein that has recently been linked to tumorigenesis in several experimental animal models and human patient studies (68,69,70). Because of its integrin-binding arginine-glycine-aspartate (RDG) domain and adhesive properties, osteopontin has been reported to play a crucial role in the metastatic process of several human tumors (68,71). However, it is only recently that the upregulated expression of osteopontin in ovarian cancer has been identified (72). Importantly, because of the secreted nature of this protein, osteopontin has been proposed as a novel biomarker for the early recognition of ovarian cancer (72). In this study, the SPP1 gene was found 10-fold differentially expressed in OSPC when compared to NOVA. Taken together these data confirm a high expression of osteopontin in OSPC.

The organization of kallikreins, a gene family now consisting of 15 genes which all encode for trypsin-like or chymotrypsin-like serine proteases, has been recently elucidated (73). Serine proteases have been described to have well characterized roles in diverse cellular activities, including blood coagulation, wound healing, digestion, and immune responses, as well as tumor invasion and metastasis (reviewed in 73). Importantly, because of the secreted nature of some of these enzymes, prostate-specific antigen (PSA) and kallikrein 2 have already found important clinical application as prostate cancer biomarkers (73). Of interest, kallikrein 6 (also known as zyme/protease M/neurosin), kallikrein 10 and matriptase (TADG-15/MT-SP1), were all found to be highly differentially expressed genes in OSPC when compared to NOVA. These data confirm previous results showing high expression of several kallikrein genes and proteins in ovarian neoplasms (73,74,75,76,77). Moreover, these results obtained by high-throughput technologies for assaying gene expression further emphasize the view that some members of the kallikrein family have the potential to become novel cancer markers for early diagnosis of ovarian cancer (77) as well as targets for novel therapies against recurrent/refractory ovarian disease (78). Other highly ranked genes in OSPC included stratifin, desmoplakin, S100A2, cytokeratins 6 and 7, and MUC-1.

A large number of down-regulated (at least 5-fold) genes in OSPC versus NOVA such as transforming growth factor beta receptor III, platelet-derived growth factor receptor alpha, SEMACAP3, ras homolog gene family member I (ARHI), thrombospondin 2 and disabled-2/differentially expressed in ovarian carcinoma 2 (Dab2/DOC2) have been identified in this analysis. Some of these genes encode for widely-held tumor suppressor genes such as SEMACAP3, ARHI, and Dab2/DOC2 (79), others for proteins important for ovarian tissue homeostasis or that have been previously implicated in apoptosis, proliferation, adhesion or tissue maintenance.

The identification of TROP-1/Ep-CAM and CPE epithelial receptors as some of the most highly differentially expressed genes in OSPC compared to NOVA indicate that novel therapeutic strategies targeting TROP-1/Ep-CAM by monoclonal antibodies and/or claudin-3 and 4 by local and/or systemic administration of *Clostridium Perfringens* enterotoxin can be an effective therapeutic modalities in patients harboring OSPC refractory to standard treatment.

Conclusions

Gene expression data identified 129 and 170 genes that exhibited >5-fold up-regulation and down-regulation, respectively, in primary OSPC when compared to NOVA. Genes overexpressed in established OSPC cell lines were found to have little correlation with those overexpressed in primary OSPC, highlighting the divergence of gene expression that occurs as the result of long-term in vitro growth. Hierarchical clustering of the expression data readily distinguished normal tissue from primary OSPC. Laminin, claudin-3 and claudin-4, tumor-associated calcium signal transducer 1 and 2 (TROP-1/Ep-CAM; TROP-2), ladinin 1, S100A2, SERPIN2 (PAI-2), CD24, lipocalin 2, osteopontin, kallikrein 6 (protease M) and kallikrein 10, matriptase (TADG-15) and stratifin were found among the most highly overexpressed genes in OSPC when compared to NOVA. Differential expression of some of these genes including claudin-3 and claudin-4, TROP-1 and CD24 was validated by quantitative RT-PCR as well as by flow cytometry on primary OSPC and NOVA. Immunohistochemical staining of formalin fixed paraffin embedded tumor specimens from which primary OSPC cultures were derived further confirmed differential expression of CD24 and TROP-1/Ep-CAM markers on OSPC vs. NOVA.

Example 2

Gene Expression Fingerprint of Uterine Serous Papillary Carcinoma: Identification of Novel Molecular Markers for Uterine Serous Cancer Diagnosis and Therapy The goal of this study was to identify genes with a differential pattern of expression between uterine serous papillary carcinoma (USPC) and normal endometrial cells (NEC) and to use this knowledge to develop novel diagnostic and therapeutic markers for uterine cancer. Oligonucleotide microarrays were used to interrogate the expression of 10,000 known genes to analyze gene expression profiling of 10 highly purified USPC cultures and 5 primary NEC. mRNA fingerprints readily distinguished USPC from normal endometrial epithelial cells and identified a number of genes highly differentially expressed between NEC and USPC.

Materials and Methods

Establishment of USPC and NEC Primary Cell Lines.

A total of fifteen primary cell lines (i.e., 10 USPC and 5 NEC) were established after sterile processing of samples from surgical biopsies collected between 1997 and 2003 at the University of Arkansas for Medical Sciences, as previously described for USPC specimens (80) and normal endometrial cell cultures (81,82). All fresh samples were obtained with appropriate consent according to IRB guidelines. Tumors were staged according to the F.I.G.O. operative staging system. A total abdominal hysterectomy with bilateral salpingo oophorectomy and bilateral pelvic lymphadenectomy was performed in all uterine carcinoma patients while normal endometrial tissue was obtained from consenting donors undergoing surgery for benign pathology. No patient received chemotherapy or radiation before surgery. The patient characteristics are described in Table 3. Briefly, normal tissue was obtained from healthy endometria, mechanically minced and enzymatically dissociated with 0.14% collagenase Type I (Sigma, St. Louis, Mo.) in RPMI 1640 as described previously by Bongso et al. with minor modifications (81). After 1-2 hrs incubation with enzyme on a magnetic stirring apparatus at 37° C. in an atmosphere of 5% $CO_2$, the resulting suspension was collected by centrifugation at 100 g for 5-10 minutes and washed twice with RPMI 1640 medium (Sigma) containing 10% fetal bovine serum (FBS, Invitrogen, Grand Island, N.Y.). The final pellet was then placed in RPMI 1640 (Sigma) containing 10% FBS, 200 u/ml penicillin, and 200 µg/ml streptomycin in tissue culture flasks or Petri dishes (Invitrogen). The epithelial explants were then allowed to attach and proliferate. Explants were trypsinized and subcultured for 1 to 2 passages before being collected for RNA extraction. Tumor tissue was mechanically minced in RPMI 1640 to portions no larger than 1-3 $mm^3$ and washed twice with RPMI 1640. The portions of minced tumor were then placed into 250 ml flasks containing 30 ml of enzyme solution [0.14% collagenase Type I (Sigma) and 0.01% DNAse (Sigma, 2000 KU/mg)] in RPMI 1640, and either incubated on a magnetic stirring apparatus for 1-2 hrs at 37° C. in an atmosphere of 5% $CO_2$ or overnight at 4° C. Enzymatically dissociated tumor was then filtered through 150 µm nylon mesh to generate a single cell suspension. The resultant cell suspension was then washed twice in RPMI 1640 plus 10% FBS. Primary cell lines were maintained in RPMI 1640, supplemented with 10% FBS, 200 u/ml penicillin, 200 µg/ml streptomycin at 37° C., 5% $CO_2$. Tumor cells were collected for RNA extraction at a confluence of 50% to 80% after a minimum of two to a maximum of ten passages in vitro. The epithelial nature and the purity of USPC and NEC cultures was verified by immunohistochemical staining and flow cytometric analysis with antibodies against cytokeratin and vimentin as previously described (80,82). Only primary cultures which had at least 90% viability and contained >99% epithelial cells were used for total RNA extraction.

TABLE 3

| Patient | Age | Stage |
| --- | --- | --- |
| USPC 1 | 65 | IV B |
| USPC 2 | 75 | III C |
| USPC 3 | 75 | IV A |
| USPC 4 | 59 | IV A |
| USPC 5 | 59 | III C |
| USPC 6 | 62 | IV B |
| USPC 7 | 63 | III C |
| USPC 8 | 61 | III C |
| USPC 9 | 78 | III C |
| USPC 10 | 64 | IV A |

Gene Cluster/Treeview.

The hierarchical clustering of average-linkage method with the centered correlation metric was used (35). For the unsupervised hierarchical clustering shown in FIG. 4, a total of 7,328 probe sets were scanned across 10 USPCs and 5 NECs. The 7,328 probe sets were derived from 12,588 by filtering out all control genes, all genes with absent detections, and genes not fulfilling the test of standard deviation greater than 0.5 (0.5 being the log base 2 of the signal). Table 4 shows only genes significantly expressed by both WRS and SAM analyses and whose average change in expression level was at least five-fold.

Results

Gene Expression Profiles Distinguish USPC from NEC and Identify Differentially Expressed Genes.

Figure 4:
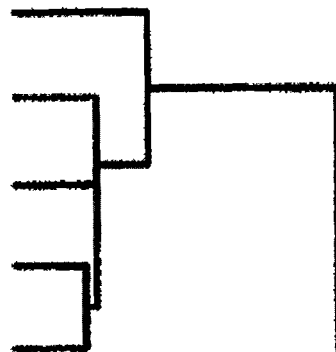
FIG. 4 depicts an unsupervised hierarchical clustering of fifteen primary uterine cell lines (10 USPC and 5 NEC).
Figure 5A:
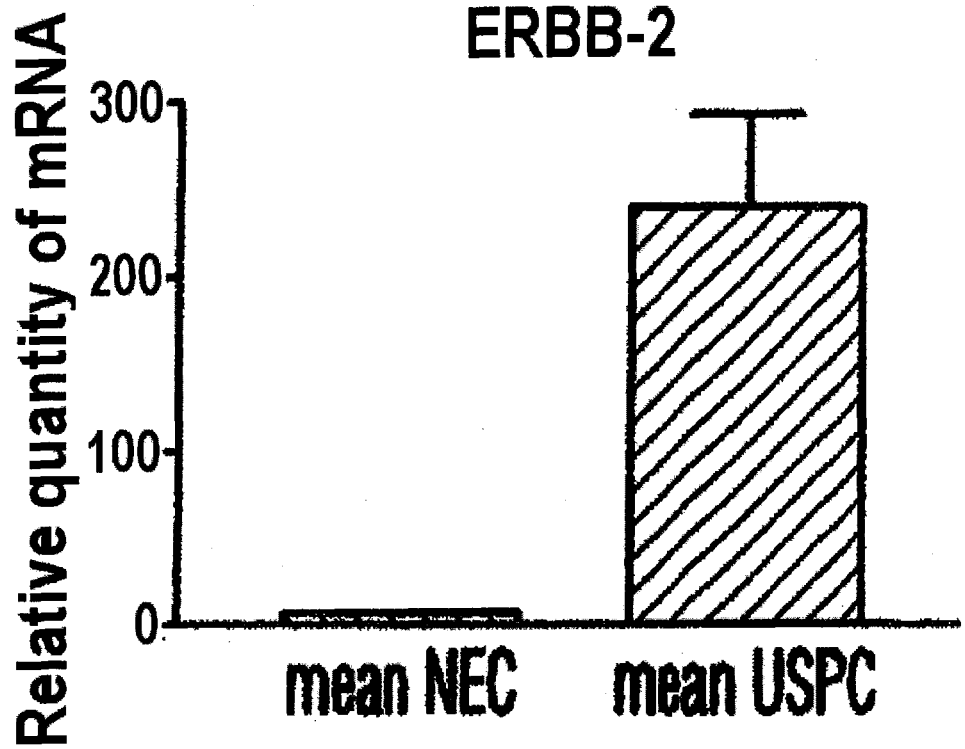
FIGS. 5A, B, C, D, E, F, G, H, I, J, K, and L show bar graphs of quantitative RT-PCR and microarray expression analysis of CDKN2A/p16, CDKN2A/p14ARF, L1CAM, claudin-3, claudin-4, GRB-7, and c-erbB2 genes differentially expressed between USPC and NEC.
Figure 5B:
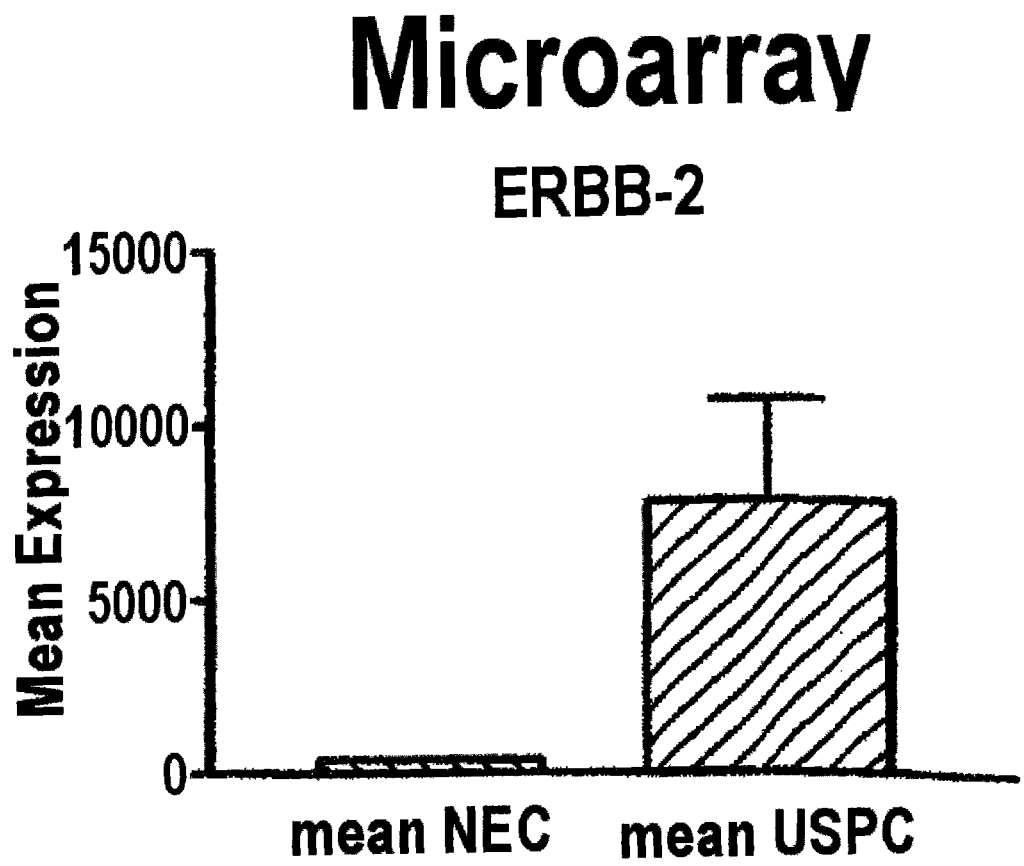
FIG. 5B, FIG. 5D, FIG. 5F, FIG. 5H, FIG. 5J, and FIG. 5L show the microarray expression analysis of c-erbB2, GRB-7, CDKN2A/p14ARF, CDKN2A/p16, claudin-3, and claudin-4, respectively.
Figure 5C:
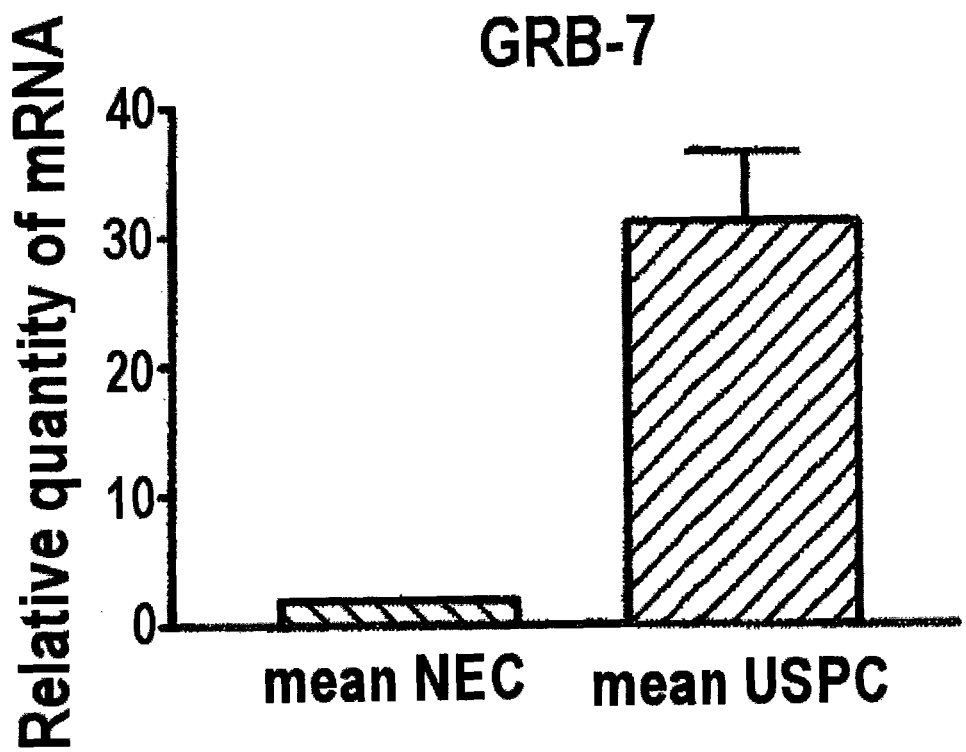
Figure 5D:
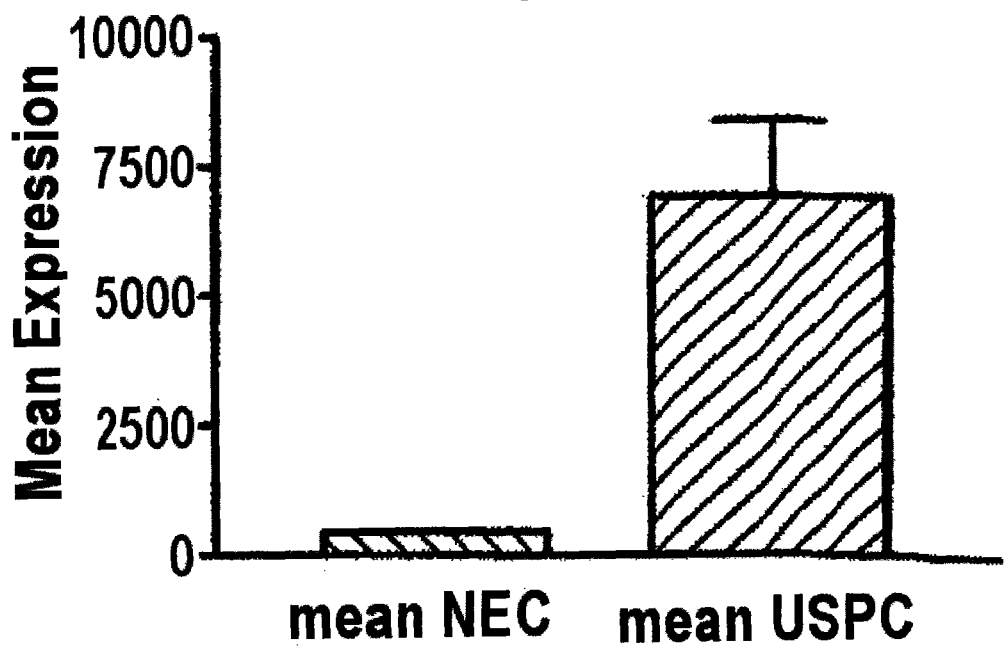
Figure 5E:
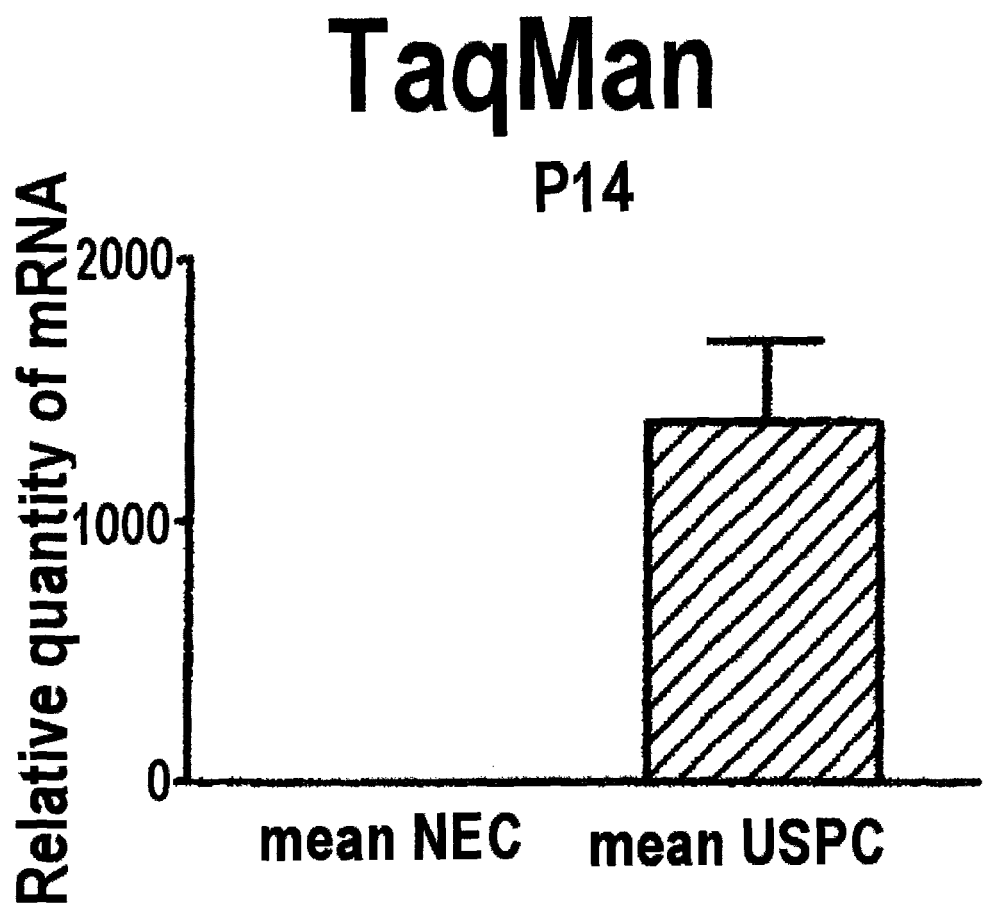
Figure 5F:
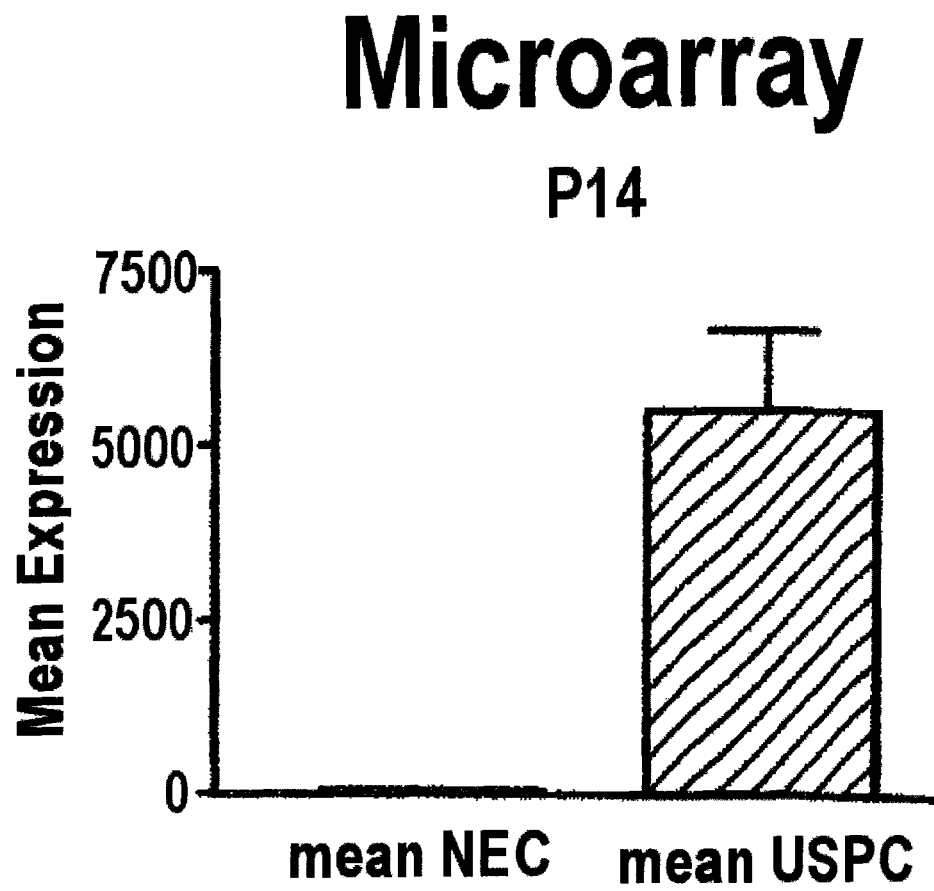
Figure 5G:
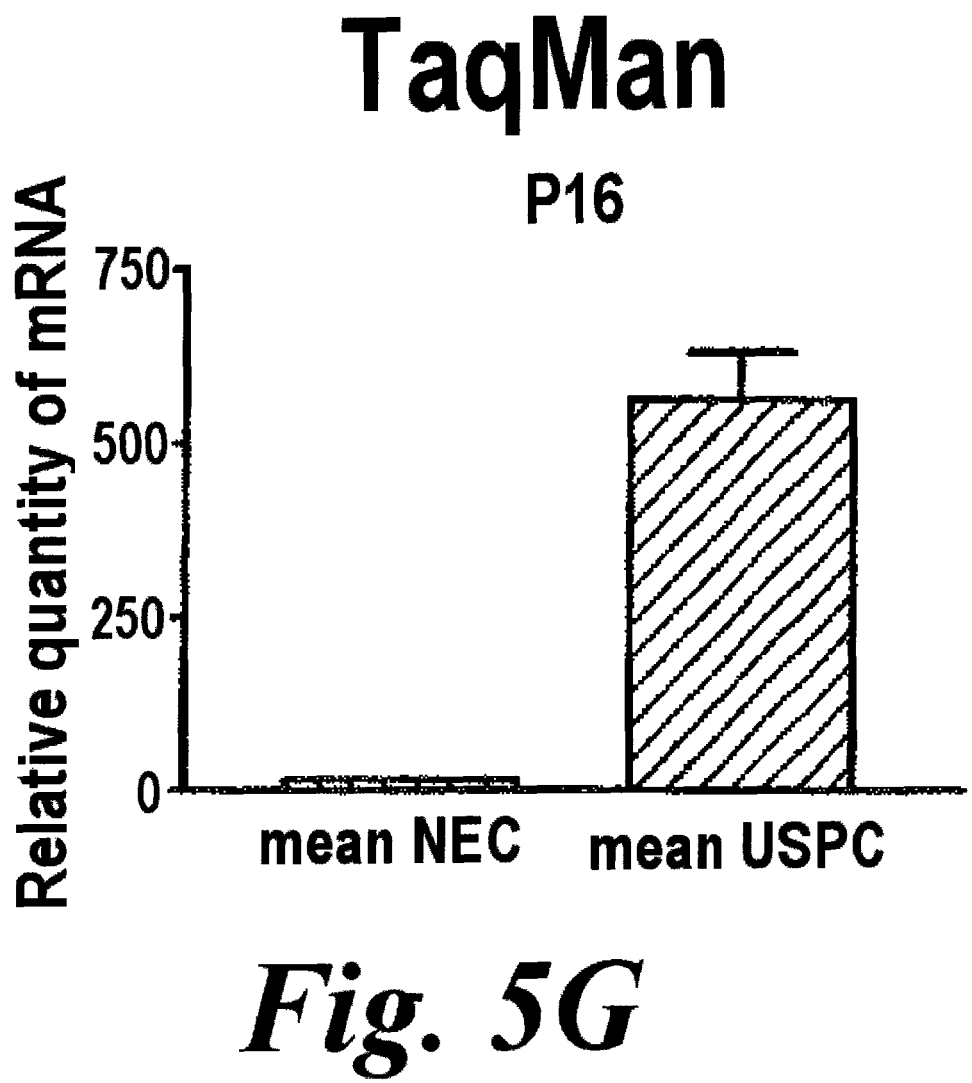
Figure 5H:
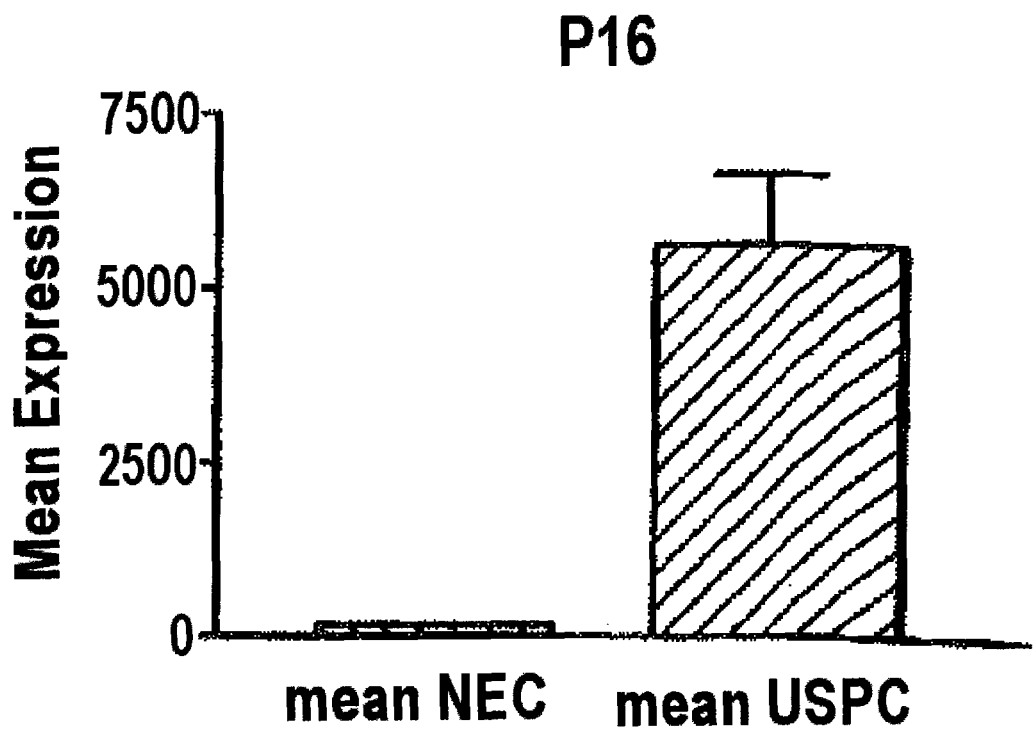
Figure 5I:
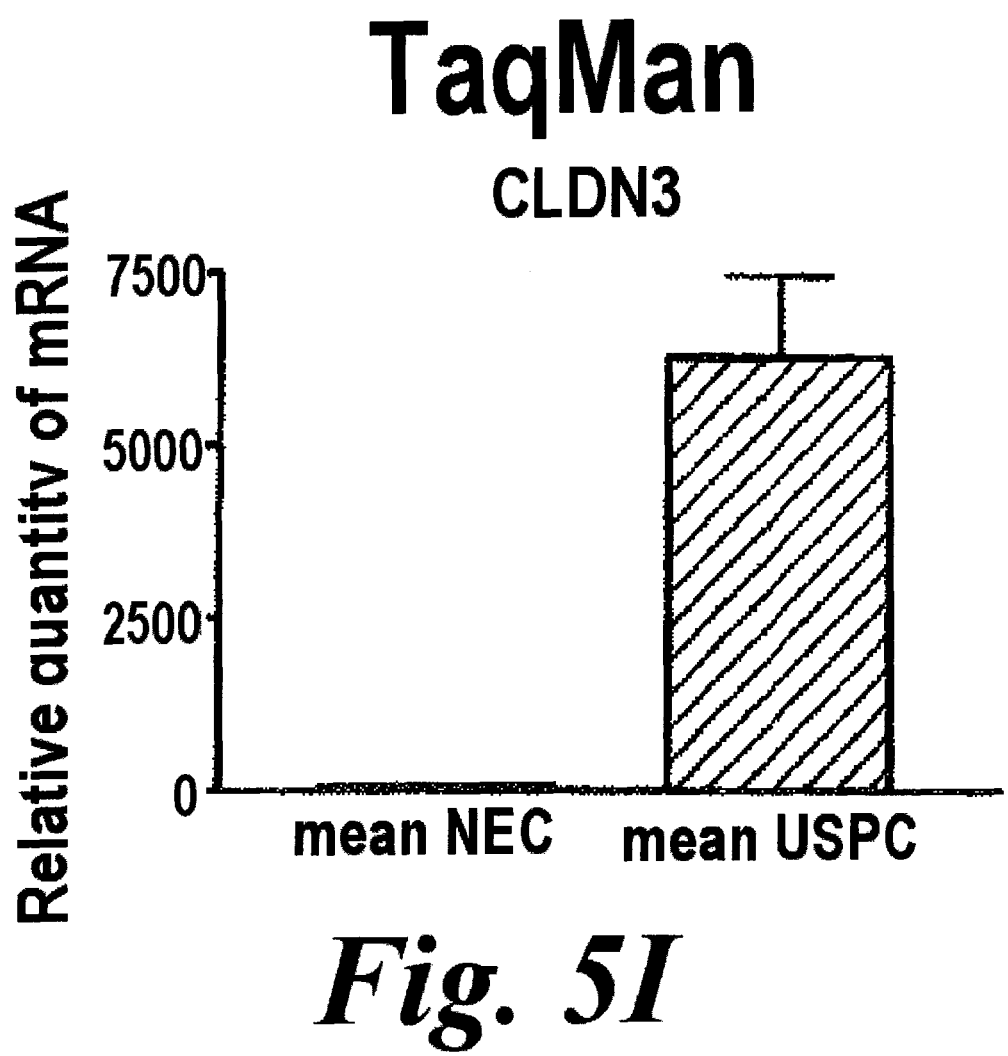
Figure 5J:
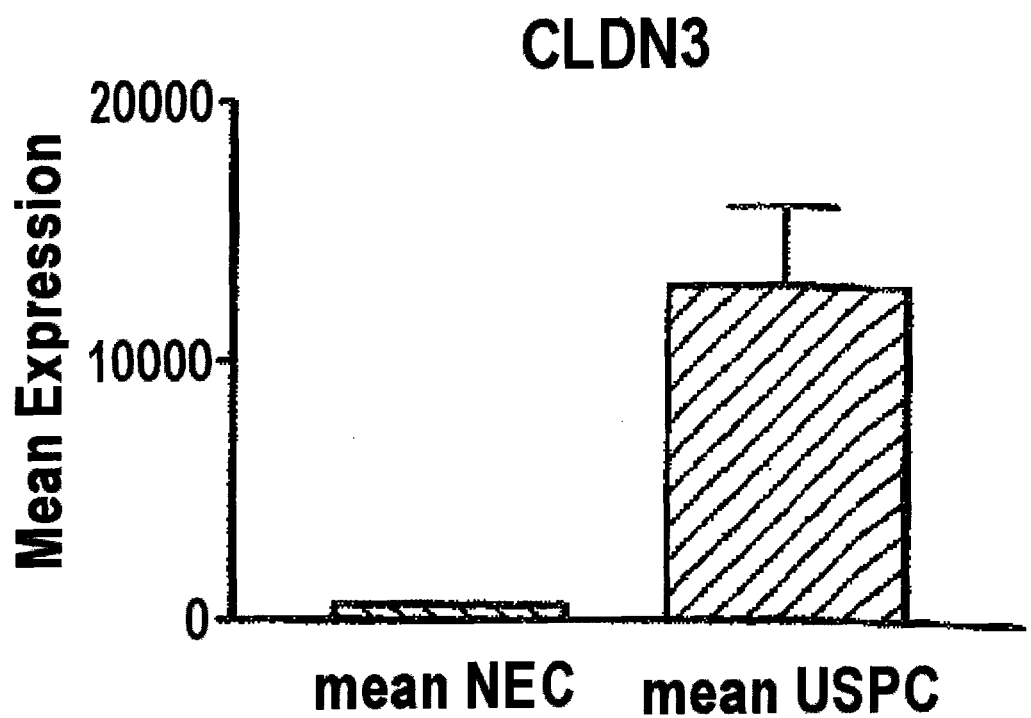
Figure 5K:
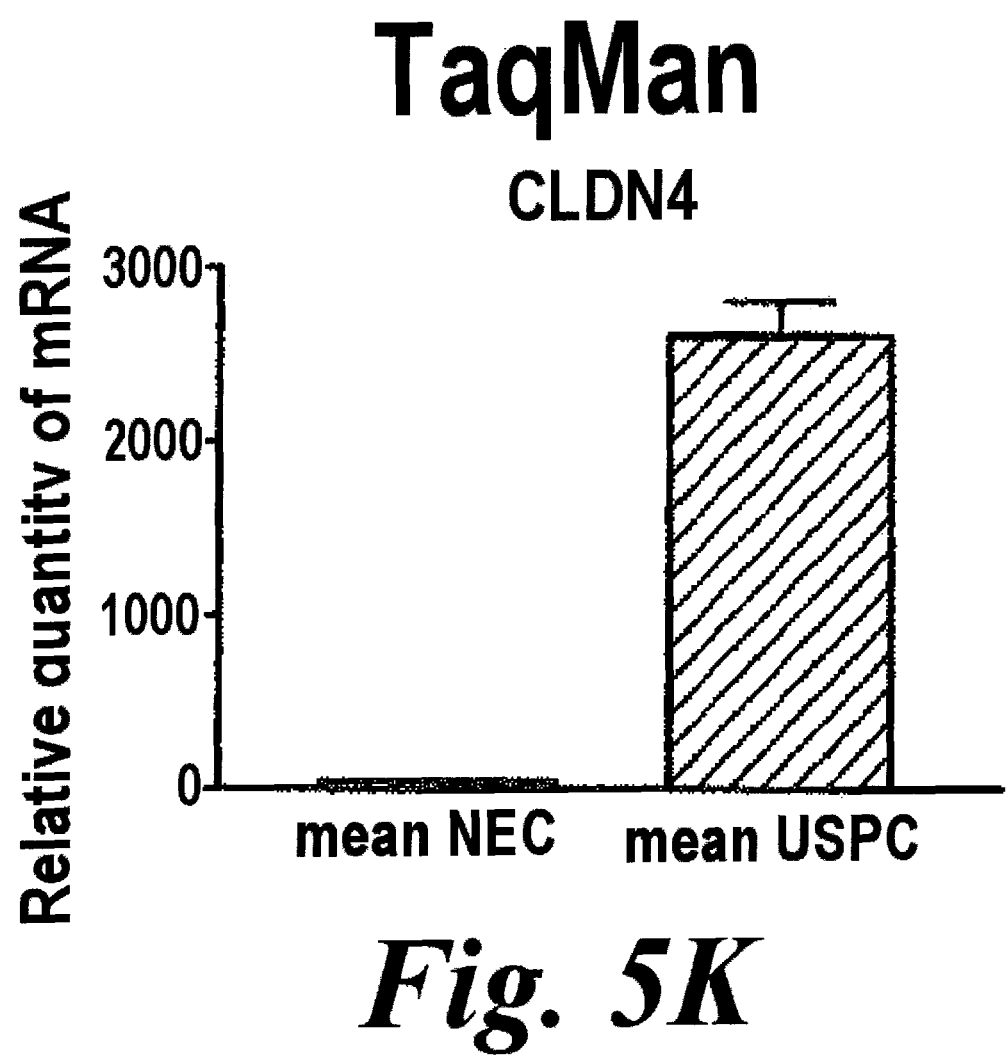
Figure 5L:
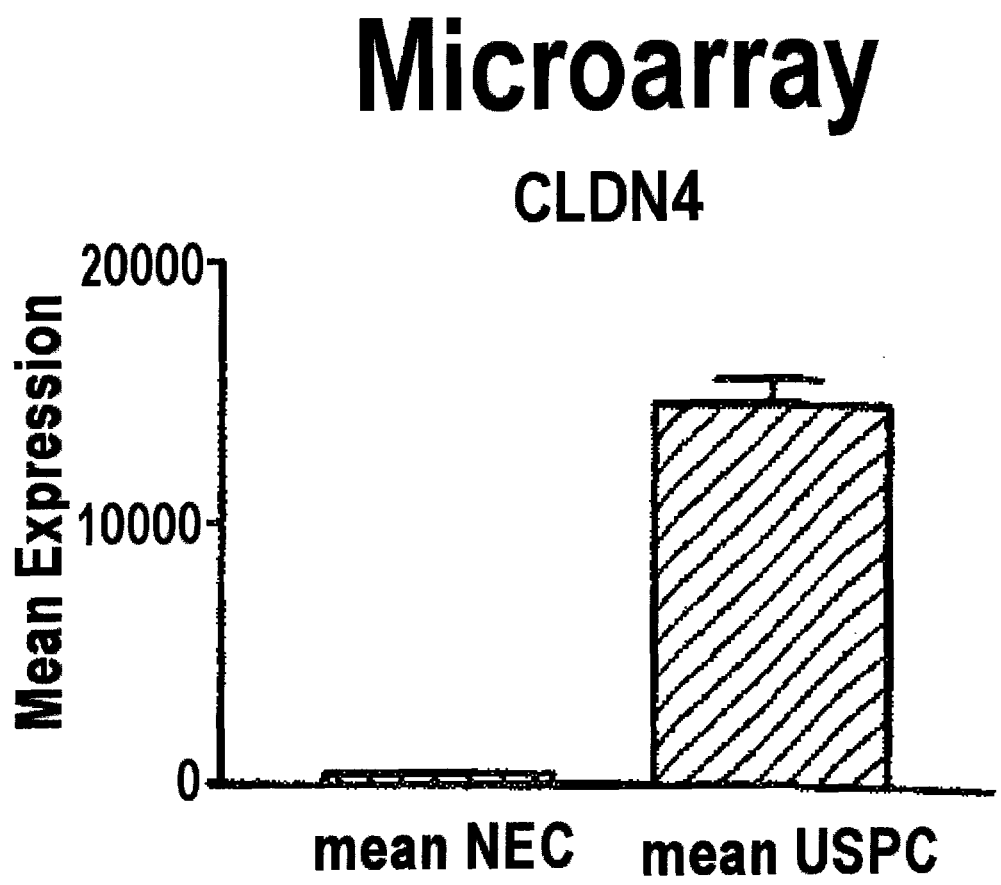

Tumor tissue flash frozen biopsies are known to contain significant numbers of contaminant stromal cells as well as a variety of host derived immune cells (e.g., monocytes, dendritic cells, lymphocytes). In addition, USPC represent rare tumors which may present in either pure forms, or admixed with endometrioid or clear cell tumor cells (i.e., mixed USPC) (9,10). To minimize the risk of contamination of USPC RNA with that of normal cells or tumor cells with different histology (i.e., endometrioid or clear cells), as well as to reduce the complexity of gene expression data analysis, in this study RNA was extracted only from short term primary tumor cell cultures collected only from USPC with single type differentiation. Short term USPC and NEC cell cultures, minimizing the risk of a selection bias inherent in any long term in vitro growth, may provide an opportunity to study differential gene expression between highly enriched populations of normal and tumor-derived epithelial cells. Accordingly, comprehensive gene expression profiles of 10 primary USPC and 5 primary NEC cell lines were generated using high-density oligonucleotide arrays with 12,533 probe sets, which in total interrogated some 10,000 genes. Characteristics of the 10 patients from whom the primary USPC cell lines were derived are shown in Table 3. Using unsupervised hierarchical cluster analysis with 7,238 probe sets, differences in gene expression between USPC and NEC were identified that readily distinguished the two groups of primary cultures. As shown in FIG. 4, all 10 USPC were found to group together in the rightmost columns of the dendrogram. Similarly, in the leftmost columns all 5 NEC were found to cluster tightly together. After filtering out most "absent" genes, the SAM and the nonparametric WRS test (p<0.05) were performed to identify genes differentially expressed between USPC and NEC. A total of 2,829 probe sets were found differentially expressed between USPC and NEC with p<0.05 by WRS and with a median FDR of 0.35% and a 90th percentile FDR of 0.59% by SAM. Of the 2,829 aforementioned probe sets, there were 529 probe sets showing >5-fold change. As shown in Table 4, a group of 139 probe sets were found highly expressed in USPC and underexpressed in NEC. Included in this group of genes are CDKN2A/p16/p14ARF, L1 cell adhesion molecule (L1 CAM), claudin-3 (CLDN3) and claudin-4 (CLDN4), kallikrein 6 (protease M) and kallikrein 10 (NES1), interleukin-6, interleukin-18 and plasminogen activator receptor (PLAUR) (Table 4). Importantly, c-erbB2 was 14-fold more highly expressed in USPC than in NEC (Table 4). The second profile was represented by 390 genes that were highly expressed in NEC and underexpressed in USPC (data not shown). Included in this group of genes are transforming growth factor beta receptor III, platelet-derived growth factor receptor alpha, SEMACAP3, ras homolog gene family, member I (ARHI), and differentially downregulated in ovarian carcinoma 1 (DOC1).

TABLE 4

Upregulated genes expressed at least 5-fold higher in USPC compared with NEC

| Probe Set | Gene Symbol | SAM Score(d) | p of wrs | Ratio uspc/nec |
|---|---|---|---|---|
| 1713_s_at | CDKN2A | 10.59223007 | 0.0027 | 101.9077377 |
| 36288_at | KRTHB1 | 4.573430656 | 0.0027 | 77.3983986 |
| 33272_at | SAA1 | 3.777977393 | 0.0063 | 45.74937337 |
| 41294_at | KRT7 | 7.173346265 | 0.0027 | 41.46788873 |
| 32154_at | TFAP2A | 7.636996321 | 0.0027 | 32.47929396 |
| 31610_at | MAP17 | 3.621151787 | 0.0093 | 30.28302802 |
| 408_at | — | 4.070053148 | 0.0063 | 30.14111158 |
| 32821_at | LCN2 | 5.126089463 | 0.0027 | 27.69975608 |
| 35174_i_at | EEF1A2 | 2.839620426 | 0.0278 | 26.80482891 |
| 38551_at | L1CAM | 3.115032534 | 0.0196 | 25.60938089 |
| 38249_at | VGLL1 | 5.273984976 | 0.0027 | 24.69495091 |
| 35879_at | GAL | 5.593811144 | 0.0027 | 23.48953559 |
| 36838_at | KLK10 | 3.455062978 | 0.0136 | 23.17518549 |
| 38299_at | IL6 | 3.62957424 | 0.0041 | 19.05873079 |
| 38051_at | MAL | 4.877642645 | 0.0041 | 17.51555106 |
| 41469_at | PI3 | 2.853526521 | 0.0063 | 16.90464558 |
| 40412_at | PTTG1 | 5.218191198 | 0.0027 | 16.61222352 |
| 1886_at | WNT7A | 3.544426758 | 0.0196 | 16.11519778 |
| 33128_s_at | CST6 | 4.221666931 | 0.0136 | 15.97856318 |
| 38414_at | CDC20 | 7.317470579 | 0.0027 | 15.64601435 |
| 34012_at | KRTHA4 | 2.410988057 | 0.0278 | 15.37247475 |
| 37554_at | KLK6 | 3.784630357 | 0.0093 | 15.23781352 |
| 1802_s_at | ERBB2 | 2.566389361 | 0.0136 | 14.52012028 |
| 41060_at | CCNE1 | 6.092165808 | 0.0027 | 14.16647068 |
| 36837_at | KIF2C | 6.129605781 | 0.0027 | 14.1328483 |
| 34213_at | KIBRA | 5.300586641 | 0.0027 | 13.27228177 |

TABLE 4-continued

Upregulated genes expressed at least 5-fold higher in USPC compared with NEC

| Probe Set | Gene Symbol | SAM Score(d) | p of wrs | Ratio uspc/nec |
|---|---|---|---|---|
| 1651_at | UBE2C | 5.554093545 | 0.0027 | 12.87617243 |
| 35276_at | CLDN4 | 6.381184288 | 0.0027 | 12.74825421 |
| 36990_at | UCHL1 | 4.623383279 | 0.0027 | 12.30505908 |
| 35977_at | DKK1 | 4.494993915 | 0.0041 | 12.25382636 |
| 36113_s_at | TNNT1 | 4.071523595 | 0.0027 | 11.93824813 |
| 2011_s_at | BIK | 3.451043397 | 0.0063 | 11.66959681 |
| 543_g_at | CRABP1 | 3.193471228 | 0.0093 | 11.55494382 |
| 34852_g_at | STK6 | 6.224691811 | 0.0027 | 11.51812047 |
| 33483_at | NMU | 4.093975777 | 0.0027 | 11.42057993 |
| 39109_at | TPX2 | 6.161639109 | 0.0027 | 11.29208457 |
| 37018_at | HIST1H1C | 2.26997194 | 0.0278 | 10.74270622 |
| 1165_at | IL18 | 3.220966429 | 0.0041 | 10.65596528 |
| 36477_at | TNNI3 | 2.867426116 | 0.0136 | 10.61101382 |
| 572_at | TTK | 3.720282658 | 0.0093 | 9.723902052 |
| 31542_at | FLG | 2.622102112 | 0.0196 | 9.600831601 |
| 35937_at | MICB | 4.238382451 | 0.0093 | 9.460109582 |
| 36155_at | SPOCK2 | 2.277735266 | 0.0278 | 9.216570003 |
| 32186_at | SLC7A5 | 4.148798845 | 0.0063 | 9.121679665 |
| 35766_at | KRT18 | 5.933225457 | 0.0027 | 9.01220054 |
| 35822_at | BF | 3.266560726 | 0.0063 | 8.952514469 |
| 35714_at | PDXK | 6.549900892 | 0.0027 | 8.898191704 |
| 1369_s_at | — | 2.679010624 | 0.0196 | 8.773380878 |
| 40079_at | RAI3 | 4.515766371 | 0.0063 | 8.626843209 |
| 37168_at | LAMP3 | 2.837727959 | 0.0136 | 8.616807346 |
| 39704_s_at | HMGA1 | 5.322233414 | 0.0027 | 8.597894471 |
| 1887_g_at | WNT7A | 3.003097491 | 0.0196 | 8.491813649 |
| 36929_at | LAMB3 | 5.769944566 | 0.0027 | 8.354149098 |
| 527_at | CENPA | 6.125858747 | 0.0027 | 8.32992789 |
| 41081_at | BUB1 | 4.882654417 | 0.0027 | 8.213759056 |
| 885_g_at | ITGA3 | 4.447267172 | 0.0027 | 8.20660555 |
| 2021_s_at | CCNE1 | 4.399072926 | 0.0041 | 8.199388463 |
| 33904_at | CLDN3 | 3.296023945 | 0.0136 | 8.020010794 |
| 33730_at | RAI3 | 4.648262631 | 0.0041 | 7.923899439 |
| 34736_at | CCNB1 | 5.077963775 | 0.0063 | 7.896644626 |
| 757_at | ANXA2 | 3.514460359 | 0.0063 | 7.870466864 |
| 910_at | TK1 | 3.933693732 | 0.0093 | 7.869091533 |
| 34851_at | STK6 | 4.491412407 | 0.0041 | 7.764803777 |
| 34703_f_at | — | 2.275488598 | 0.0278 | 7.710260816 |
| 34715_at | FOXM1 | 5.318031066 | 0.0027 | 7.659023602 |
| 38971_r_at | TNIP1 | 6.799881197 | 0.0027 | 7.595036872 |
| 32263_at | CCNB2 | 4.245537907 | 0.0063 | 7.578513543 |
| 1680_at | GRB7 | 4.013375211 | 0.0027 | 7.471384928 |
| 38247_at | F2RL1 | 3.185259514 | 0.0093 | 7.432476326 |
| 160025_at | TGFA | 6.08814344 | 0.0027 | 7.355344272 |
| 1945_at | CCNB1 | 5.297806506 | 0.0041 | 7.291039832 |
| 31792_at | ANXA3 | 4.872657477 | 0.0041 | 7.266892828 |
| 182_at | ITPR3 | 5.431705752 | 0.0027 | 7.172450367 |
| 1117_at | CDA | 2.936875649 | 0.0093 | 7.114518646 |
| 902_at | EPHB2 | 5.186069433 | 0.0027 | 7.065363569 |
| 634_at | PRSS8 | 5.21560703 | 0.0041 | 7.001894703 |
| 41169_at | PLAUR | 3.982498409 | 0.0063 | 7.00139089 |
| 33203_s_at | FOXD1 | 3.4642857 | 0.0093 | 6.989749222 |
| 40095_at | CA2 | 4.285159359 | 0.0027 | 6.946396937 |
| 38940_at | AD024 | 5.064744169 | 0.0041 | 6.928406028 |
| 34348_at | SPINT2 | 6.262957935 | 0.0027 | 6.877224695 |
| 33933_at | WFDC2 | 3.343526736 | 0.0136 | 6.820073691 |
| 35281_at | LAMC2 | 3.346662529 | 0.0093 | 6.7580474 |
| 349_g_at | KIFC1 | 5.275031682 | 0.0041 | 6.700913018 |
| 33218_at | ERBB2 | 2.710053625 | 0.0027 | 6.615105998 |
| 38881_i_at | TRIM16 | 3.000641338 | 0.0196 | 6.506893575 |
| 1536_at | CDC6 | 4.666131295 | 0.0041 | 6.463305623 |
| 38482_at | CLDN7 | 4.930843791 | 0.0041 | 6.409117877 |
| 40697_at | CCNA2 | 3.396480338 | 0.0093 | 6.40768505 |
| 41688_at | TM4SF11 | 4.390330663 | 0.0027 | 6.366861533 |
| 38158_at | ESPL1 | 6.007466409 | 0.0027 | 6.225688779 |
| 38474_at | CBS | 3.379648389 | 0.0093 | 6.212078913 |
| 36483_at | GALNT3 | 3.889728637 | 0.0041 | 6.181109111 |
| 35372_r_at | IL8 | 2.359705895 | 0.0278 | 6.133149591 |
| 41585_at | KIAA0746 | 4.436299723 | 0.0027 | 6.092207586 |
| 36832_at | B3GNT3 | 5.456967667 | 0.0027 | 5.941291793 |
| 1107_s_at | G1P2 | 3.937533177 | 0.0063 | 5.923287019 |
| 35207_at | SCNN1A | 3.076038486 | 0.0136 | 5.920739634 |
| 36863_at | HMMR | 2.830001586 | 0.0196 | 5.905038013 |
| 38631_at | TNFAIP2 | 4.924314508 | 0.0027 | 5.897745642 |

TABLE 4-continued

Upregulated genes expressed at least 5-fold higher in USPC compared with NEC

| Probe Set | Gene Symbol | SAM Score(d) | p of wrs | Ratio uspc/nec |
|---|---|---|---|---|
| 36813_at | TRIP13 | 5.665655915 | 0.0027 | 5.870351247 |
| 41048_at | PMAIP1 | 3.489974054 | 0.0062 | 5.853172336 |
| 2084_s_at | ETV4 | 3.742551143 | 0.0093 | 5.798002338 |
| 33245_at | MAPK13 | 3.774897977 | 0.0136 | 5.766618762 |
| 37347_at | CKS1B | 5.542650247 | 0.0027 | 5.762817533 |
| 34282_at | NFE2L3 | 2.668167751 | 0.0136 | 5.734907375 |
| 330_s_at | — | 4.026422371 | 0.0041 | 5.726752495 |
| 41732_at | na | 6.920337146 | 0.0027 | 5.706487141 |
| 1516_g_at | — | 6.725730866 | 0.0027 | 5.63870137 |
| 904_s_at | TOP2A | 3.418887485 | 0.0063 | 5.634251452 |
| 36041_at | EXO1 | 4.970840916 | 0.0027 | 5.59235892 |
| 33143_s_at | SLC16A3 | 4.007293245 | 0.0063 | 5.56591457 |
| 37228_at | PLK | 4.500601808 | 0.0041 | 5.564532365 |
| 1854_at | MYBL2 | 4.116712652 | 0.0063 | 5.54317592 |
| 40407_at | KPNA2 | 4.188947411 | 0.0041 | 5.51635645 |
| 33282_at | LAD1 | 3.904051584 | 0.0063 | 5.509367036 |
| 40145_at | TOP2A | 3.30652637 | 0.0093 | 5.48127065 |
| 1100_at | IRAK1 | 5.530078337 | 0.0027 | 5.470162749 |
| 37883_i_at | AF038169 | 3.159630542 | 0.0027 | 5.460495655 |
| 37343_at | ITPR3 | 5.257721251 | 0.0027 | 5.449013729 |
| 31598_s_at | GALE | 4.646763029 | 0.0027 | 5.442955253 |
| 889_at | ITGB8 | 2.743766192 | 0.0093 | 5.370592815 |
| 37558_at | IMP-3 | 3.122846843 | 0.0093 | 5.364127468 |
| 32715_at | VAMP8 | 5.685902454 | 0.0027 | 5.352873419 |
| 36312_at | SERPINB8 | 3.611288676 | 0.0027 | 5.327343554 |
| 37210_at | INA | 3.550708512 | 0.0063 | 5.307526088 |
| 35699_at | BUB1B | 3.664553007 | 0.0196 | 5.279075308 |
| 32787_at | ERBB3 | 2.657607539 | 0.0041 | 5.247404657 |
| 32275_at | SLPI | 3.726091901 | 0.0041 | 5.221163981 |
| 893_at | E2-EPF | 3.774672918 | 0.0063 | 5.196412396 |
| 41583_at | FEN1 | 5.481105111 | 0.0027 | 5.196005796 |
| 41781_at | PPFIA1 | 4.113488223 | 0.0027 | 5.194931774 |
| 40726_at | KIF11 | 2.94101083 | 0.0093 | 5.1806793 |
| 41400_at | TK1 | 4.245983179 | 0.0093 | 5.167172588 |
| 41409_at | C1orf38 | 3.109232321 | 0.0063 | 5.100239097 |
| 40425_at | EFNA1 | 2.738432716 | 0.0196 | 5.067718102 |
| 32081_at | CIT | 6.162032917 | 0.0027 | 5.043567722 |
| 1108_s_at | EPHA1 | 4.863995126 | 0.0027 | 5.040980858 |
| 33338_at | STAT1 | 3.274771895 | 0.0063 | 5.029498048 |

Validation of the Microarray Data.

Quantitative-RT-PCR assays were used to validate the microarray data. Seven highly differentially expressed genes between USPC and NEC (i.e., CDKN2A/p16, CDKN2A/p14ARF, L1 CAM, claudin-3, claudin-4, GRB-7 and c-erbB2) were selected for q-RT-PCR analysis. A comparison of the microarray and q-RT-PCR data for these genes is shown in FIG. 5. Expression differences between USPC and NEC for CDKN2A/p16=0.002), CDKN2A/p14 ARF (p=0.002), L1CAM, (p=0.01), claudin-3 (p=0.01), claudin-4 (p=0.002) GRB-7 (p=0.002) and c-erbB2 (p=0.01) were readily apparent (Table 4 and FIG. 4). Moreover, for all seven genes tested, the q-RT-PCR data were highly correlated to the microarray data (p<0.001)(r=0.81, 0.80, 0.75, 0.69, 0.82, 0.71 and 0.65, respectively), with all the samples (i.e., 10 USPC and 5 NEC) included in both the q-RT-PCR and microarray experiments. Thus, q-RT-PCR data suggest that most array probe sets are likely to accurately measure the levels of the intended transcript within a complex mixture of transcripts.

Claudin-4 Expression by Immunohistology on USPC and NEC Tissue Blocks.

To determine whether the high or low expression of the claudin-4 gene detected by microarray and q-RT-PCR assays in primary USPC and NEC cell lines, respectively, is the result of a selection of a subpopulation of cancer cells present in the original tumor, or whether in vitro expansion conditions may have modified gene expression, immunohistochemical analysis of claudin-4 protein expression on formalin fixed tumor tissue was performed on the uncultured primary surgical specimens from which the USPC cell lines were derived. Both cytoplasmic and membranous staining for claudin-4 protein expression was noted in the majority of USPC specimens (i.e., 90% score 3+ and 2+) (Table 5, micrographs not shown). In contrast, only low levels of membranous staining for claudin-4 protein was found in the NEC tissue samples tested by immunohistochemistry (Table 5, p=0.02 USPC vs. NEC by student t test). To confirm and validate the immunohistochemical results in an independent series of USPC, formalin fixed tumor tissue blocks from 8 further surgical specimens (i.e., USPC 11 to 18, Table 5) similarly obtained from patients harboring advanced stage disease were tested for claudin-4 expression. Again, heavy cytoplasmic and/or membranous staining for the claudin-4 receptor was found in the striking majority of the further USPC sample tested.

TABLE 5

Claudin-4 staining

| Patient | Claudin-4 positivity |
|---|---|
| NEC 1 | 1+ |
| NEC 2 | 1+ |
| NEC 3 | 1+ |
| NEC 4 | 1+ |
| NEC 5 | 1+ |
| USPC 1 | 3+ |
| USPC 2 | 3+ |
| USPC 3 | 3+ |
| USPC 4 | 2+ |
| USPC 5 | 3+ |
| USPC 6 | 2+ |
| USPC 7 | 3+ |
| USPC 8 | 1+ |
| USPC 9 | 3+ |
| USPC 10 | 3+ |
| USPC 11 | 3+ |
| USPC 12 | 3+ |
| USPC 13 | 1+ |
| USPC 14 | 2+ |
| USPC 15 | 3+ |
| USPC 16 | 2+ |
| USPC 17 | 3+ |
| USPC 18 | 2+ |

Discussion

Hierarchical clustering of the samples and gene expression levels within the samples led to the unambiguous separation of USPC from NEC. This study identified 529 genes differentially expressed between USPC and NEC whose average change in expression level between the two groups was at least five-fold and which were found significant with both WRS test and SAM analysis. The known function of some of these genes may provide insights in the molecular pathogenesis and the highly aggressive biologic behavior of uterine serous tumors while others may prove to be useful diagnostic and therapeutic markers against this disease.

For example, the cyclin-dependent kinase inhibitor 2A (CDKN2A) gene was found to be the most highly differentially expressed gene in USPC with over 101-fold up-regulation relative to NEC. Importantly, the CDKN2A gene is a putative oncosuppressor gene encoding two unrelated proteins, both cellular growth inhibitors, in different reading frames (83). One is p16, which regulates retinoblastoma protein (pRb)-dependent G1 arrest, and the second is p14ARF, which blocks MDM2-induced p53 degradation, resulting in an increase in p53 levels and consequent cell cycle arrest (83). Although loss of p53 function is considered critical for the molecular pathogenesis of USPC (84,85), it is only recently that abnormality of the Rb pathway has been suggested to define a subgroup of aggressive endometrial carcinomas with poor prognosis (86). Quantitative RT-PCR analysis of expression of both p16 and p14ARF in the USPC series found extremely high levels of both transcripts, suggesting that the marked overexpression of the CDKN2A gene may be attributable to a negative feedback loop due to the loss of function of both pRb and p53 proteins (84,85,86). Consistent with this view, an inverse relationship between the expression of p16 and p14ARF proteins and the presence of normal or functional Rb and p53 in human cancer cells has been previously demonstrated (87,88). Thus, these data suggest for the first time that CDKN2A gene overexpression may represent a consistent genetic anomaly of USPC secondary to an autoregulatory feedback loop due to disruption of both the p16-CDK4/cyclin D1-pRb pathway and the p14ARF-MDM2-p53 pathway.

Among the genes identified here, lipocalin-2 has not been previously linked to uterine cancer. Lipocalins are extracellular carriers of lipophilic molecules such as retinoids, steroids, and fatty acid, all of which may play important roles in the regulation of epithelial cell growth (70,71). In addition, because lipocalin is a secreted protein, it may play a role in the regulation of cell proliferation and survival (70,71). Of interest, two recent publications on gene expression profiling of breast and pancreatic cancer have proposed lipocalin-2 as a novel therapeutic and diagnostic marker for prevention and treatment of these diseases (89,90). On the basis of the present findings, lipocalin-2 may be added to the known markers for USPC.

Among the several potential therapeutic target gene products identified, genes encoding tight junction (TJ) proteins claudin-3 and claudin-4 were consistently found as two of the most highly up-regulated genes in USPC, with over 8 and 12-fold up-regulation, respectively, relative to NEC. Although the exact function of claudin-3 and claudin-4 in USPC is still unclear, these proteins have been shown to represent the epithelial receptors for *Clostridium perfringens* enterotoxin (CPE), and to be the only family members of the transmembrane tissue-specific claudin proteins capable of mediating CPE binding and cytolysis. Protein expression data obtained by immunohistochemistry with anti-claudin-4 antibody on USPC blocks further support the proposal that claudins may represent therapeutic targets.

The organization of kallikreins, a gene family now consisting of 15 genes that encode for trypsin-like or chymotrypsin-like serine proteases, has been recently elucidated (77). Serine proteases have well characterized roles in diverse cellular activities, including blood coagulation, wound healing, digestion, and immune responses, as well as tumor invasion and metastasis (reviewed in 77). Secreted serine proteases such as prostate-specific antigen (PSA) and kallikrein 2 have already found important clinical application as prostate cancer biomarkers (77). Of interest, kallikrein 6 (also known as zyme/protease M/neurosin), and kallikrein-10 (NES1), two serine proteases recently shown to be present at high levels in the circulation of a subset of ovarian cancer patients (80,81,91), were both highly differentially expressed genes in USPC when compared to NEC. Kallikrein 6 and kallikrein 10 overexpression has been shown to correlate with intrinsic resistance to adjuvant chemotherapy and with a poor prognosis in ovarian cancer patients (81,014). These data are thus consistent with the present results showing high expression of kallikreins 6 and kallikrein 10 in USPC, a variant of endometrial carcinoma characterized by an aggressive biologic behavior and an inborn resistance to chemotherapy (7,8,9,10,12).

c-erbB2 gene was found to be one of the most highly differentially expressed genes in USPC with over 14-fold up-regulation compared with NEC. Furthermore, the growth factor receptor-bound protein 7 (GRB7), a gene tightly linked to c-erbB2 and previously reported coamplified and coexpressed with this gene in several cancer types (92) was also highly differentially expressed in USPC compared to NEC. These data confirm our recent discovery of a striking overexpression of the c-erbB2 gene product HER2/neu on 80% of pure USPC (93). Thus, HER2/neu overexpression may represent a distinctive molecular marker that in addition to having the potential to facilitate differentiation of USPC from the histologically indistinguishable high grade serious ovarian tumors, may also provide insights into the disproportionately poor prognosis of USPC patients (94,95,96,97). Previous studies have reported that HER2/neu overexpression in USPC patients may be associated with resistance to chemotherapeutic drugs and shorter survival (96,97). However, high overexpression of the c-erbB2 gene on USPC provides support for the notion that trastuzumab (HERCEPTIN™, Genentech, San Francisco, Calif.), a humanized anti-HER-2/Neu antibody that is showing great promise for treatment of metastatic breast cancer patients overexpressing HER-2/Neu protein (98), may be a novel, potentially highly effective therapy against USPC. Consistent with this view, high sensitivity of USPC natural killer (NK) cell-mediated antibody-dependent cytotoxicity triggered by anti-HER-2/Neu-specific antibody in vitro (93), as well as clinical responses in vivo (99) have recently been reported with the use of Herceptin in USPC patients.

L1 adhesion molecule (L1CAM), is a 200-220 kD type I membrane glycoprotein of the immunoglobulin family which plays an important function for development of the nervous system by regulating cell adhesion and migration (100). In addition, L1 CAM has been recently reported to be expressed on a variety of human tumor cell lines such as neuroblastomas, melanomas, and lung carcinomas (101,102, 103). Because overexpression of L1CAM by tumor cells may enhance cell migration on various extracellular membrane substrates, this molecule has been suggested to play a role in the adhesion and migration events crucial for tumor spreading (100,101). In the present analysis, L1CAM was found to be one of the most highly differentially expressed genes in USPC, with over 25-fold up-regulation relative to NEC. These data are in agreement with a recent report showing high expression of L1 CAM in a subset of ovarian and uterine cancers (104). Importantly, patients with L1-positive carcinomas had a poorer prognosis and shorter survival time compared with patients whose tumors were L1-negative (104), suggesting a direct correlation between L1CAM overexpression and aggressive biologic behavior. Of interest, however, high levels of soluble L1 CAM molecules resulting from cleavage of its ectodomain by the metalloproteinase ADAM10 (105) have been detected in serum samples of patients with ovarian and uterine tumors (104). These observations, combined with the results herein, support the use of L1 CAM as a novel biomarker for prediction of clinical outcome in USPC patients.

Several other highly ranked genes have been identified in this USPC gene expression profiling analysis including membrane-associated protein 17 (MAP 17), galanin, urokinase plasminogen activator receptor (UPAR), interleukin-6, forkhead box M1, interleukin-18, dickkopf homolog 1 (DKK1), coagulation factor II (thrombin) receptor-like 1, transforming growth factor, alpha, interleukin 8, topoisomerase (DNA) II alpha, hyaluronan-mediated motility receptor (RHAMM) and secretory leukocyte protease inhibitor (antileukoproteinase). For most of the genes found differentially expressed in these experiments a correlation with USPC cancer development and progression has not been recognized before. DKK1, for example, has been recently reported by our group to play an important role in the development of osteolytic lesions in multiple myeloma (106), but its possible role in USPC pathogenesis and/or progression has not been elucidated. For other genes such as UPAR, a glycosyl-phosphatidylinositol-anchored glycoprotein whose role in promoting tumor cell invasion and metastases has been well established in a number of experimental studies (107,108,109), a correlation with high expression in the uterine serous papillary carcinoma phenotype has been recently reported (110). In this regard, because UPAR protein exists in two forms, as the glycosyl-phosphatidylinositol-anchored glycoprotein (50-60 kDa) present on the surface of cells, and as a soluble form of UPAR (sU-PAR), produced after cleavage of UPAR by urokinase (35 kDa), measurement of UPAR levels by ELISA, in analogy to breast cancer (111), can be used as a prognostic marker to identify early recurrences in endometrial cancer patients associated with poor outcome. Finally, the recent demonstration of UPAR as a suitable cancer target for both therapeutic and diagnostic application by specific antibody directed against its ligand binding domain (112) may provide a foundation for the development of a new type-specific therapy against this highly aggressive disease.

A large number of down-regulated (at least 5-fold) genes in USPC versus NEC such as transforming growth factor beta receptor III, platelet-derived growth factor receptor alpha, SEMACAP3, ras homolog gene family member I (ARHI), and differentially downregulated in ovarian carcinoma 1 (DOC1) have been identified in this analysis. Some of these genes encode for widely-held tumor suppressor genes such as SEMACAP3, ARHI, and DOC1 (113), others for proteins important for tissue homeostasis or that have been previously implicated in apoptosis, proliferation, adhesion or tissue maintenance.

In conclusion, multiple USPC restricted markers have been identified in this analysis. Most of these genes have not been previously linked with this disease and thus represent novel findings. The identification of HER2/neu and CPE epithelial receptors among the others as some of the most highly differentially expressed genes in USPC when compared to NEC indicate that therapeutic strategies targeting HER2/neu by monoclonal antibodies (93,99) and claudin-3 and claudin-4 by local and/or systemic administration of *Clostridium Perfringens* enterotoxin can be effective modalities for the treatment of patients harboring this highly aggressive and chemotherapy resistant variant of endometrial cancer.

Conclusions

Unsupervised analysis of mRNA fingerprints readily distinguished USPC from NEC and identified 139 and 390 genes that exhibited >5-fold up-regulation and down-regulation, respectively, in primary USPC when compared to NEC. Many of the genes up-regulated in USPC were found to represent adhesion molecules, secreted proteins and oncogenes, such as L1 cell adhesion molecule (L1CAM), claudin-3 and claudin-4, kallikrein 6 (protease M) and kallikrein 10, (NES1), interleukin-6, interleukin-18, urokinase plasminogen activator receptor (UPAR), and c-erbB2. Down-regulated genes in USPC included transforming growth factor beta receptor III, platelet-derived growth factor receptor alpha, SEMACAP3, ras homolog gene family, member I (ARHI), and differentially downregulated in ovarian carcinoma gene 1 (DOC1). Quantitative RT-PCR was used to validate differences in gene expression between USPC and NEC for some of these genes, including cyclin-dependent kinase inhibitor 2A (CDKN2A/p16 and CDKN2A/p14ARF), L1CAM, claudin-3, claudin-4, GRB-7 and c-erbB2. Finally, expression of the high affinity epithelial receptor for *Clostridium perfringens* enterotoxin (CPE) claudin-4, was further validated through immunohistochemical analysis of formalin-fixed paraffin-embedded specimens from which the primary USPC cultures were obtained, as well as an independent set of archival specimens.

Example 3

Treatment of Chemotherapy-Resistant Human Ovarian Cancer Xenografts in C.B-17/SCID Mice by Intraperitoneal Administration of *Clostridium Perfringens* Enterotoxin (CPE)

In this study, real-time PCR was used to quantify the expression levels of claudin-3 and claudin-4 receptors in several chemotherapy naïve and chemotherapy resistant freshly explanted ovarian tumors. In addition, the ability of CPE to kill chemotherapy sensitive and chemotherapy resistant ovarian cancers overexpressing claudin-3 and/or claudin-4-in vitro was tested. Finally, the in vivo efficacy of CPE therapy in SCID mouse xenografts was studied in a highly relevant clinical model of chemotherapy resistant freshly explanted human ovarian cancer (i.e., OVA-1).

Materials and Methods

Cloning and Purification of $NH_2$ Terminus his-Tagged CPE.

*Clostridium perfringens* strain 2917 obtained from American Type Culture Collection (Manassas, Va.) was grown from a single colony and used to prepare bacterial DNA with the INSTAGENE™ kit, according to manufacturer's directions (Bio-Rad Lab, Hercules, Calif.). The bacterial DNA fragment encoding full-length CPE gene (GenBank AJ000766) was PCR amplified (primer 1, 5'-AGA TGT TAA TGG ATC CAT GCT TAG TAA CAA TTT AAA TCC-3' (SEQ ID NO:6); primer 2, 5'-AAA GCT TTT AAA ATT TTT GAA ATA ATA TTG AAT AAG GG-3' (SEQ ID NO:7)). The PCR products were digested with the restriction enzymes SphI/HindIII and cloned into a SphI/HindIII-digested pQE-30 expression vector (Qiagen, Valencia, Calif.) to generate an in-frame $NH_2$-terminus His-tagged CPE expression plasmid, pQE-30-6×HIS-CPE. His-tagged CPE toxin was prepared from pQE-30-6×HIS-CPE transformed *Escherichia coli* M15. Transformed bacteria were grown at 37° C. to 0.3-0.4 optical density at 600 nm, after which CPE protein expression was induced overnight with 1 mM isopropyl β-D-thio-galactoside, and the cells harvested, resuspended in 150 mM $NaH_2PO_4$, 25 mM Tris-HCL, and 8 M urea pH 8.0 buffer, and lysed by centrifugation at 10.000 rpm for 30 min. The fusion protein was isolated from the supernatant on a POLY-PREP™ Chromatography column (Bio-Rad). His-tagged CPE was washed with 300 mM $NaH_2PO_4$, 25 mM Tris-HCl, and 10 M urea pH 6.0, and eluted from the column with 200 mM $NaH_2PO_4$, 25 mM Tris-HCl, and 8 M urea pH 6.0. In order to reduce the level of endotoxin from His-tagged CPE protein 10 washings with ice-cold PBS with TRITON-X-114™ (from 1% to 0.1%) and 10 washings with ice-cold PBS alone were performed. Dialysis ($M_r$ 3,500 cutoff dialysis tubing) against PBS was performed overnight. Purified CPE protein was then sterilized by 0.2 μm filtration and frozen in aliquots at −70° C.

Primary and Established Cell Lines.

Fresh human ovarian cancer cell lines (i.e., eleven chemotherapy naïve tumors generated from samples obtained at the time of primary surgery and six chemotherapy resistant tumors obtained from samples collected at the time of tumor recurrence), and 5 established ovarian cancer cell lines (UCI 101, UCI 107, CaOV3, OVACAR-3, OVARK-5) were evaluated for claudin-3 and claudin-4 expression by real time-PCR. Patient characteristics from which primary specimens were obtained are depicted in Table 6. Three of the six ovarian tumor specimens found resistant to chemotherapy in vivo, including OVA-1, a fresh ovarian serous papillary carcinoma (OSPC) used to establish ovarian xenografts in SCID mice, were confirmed to be highly resistant to multiple chemotherapeutic agents when measured as percentage cell inhibition (PCI) by in vitro Extreme Drug Resistance (EDR) assay (Oncotech Inc. Irvine, Calif.) (114) (data not shown). UCI-101 and UCI-107, two previously characterized and established human serous ovarian cancer cell lines were kindly provided by Dr. Alberto Manetta, University of California, Irvine, while CaOV3, OVACAR-3, were purchased from ATCC (Manassas, Va.), and OVARK-5 was established from a stage IV ovarian cancer patient, as previously described (115). Other control cell lines evaluated in the CPE assays included Vero cells, normal ovarian epithelium (NOVA), normal endometrial epithelium, normal cervical keratinocytes, primary squamous and adenocarcinoma cervical cancer cell lines, Epstein-Barr transformed B lymphocytes (LCL), and human fibroblasts. With the exception of normal cervical keratinocytes and cervical cancer cell lines which were cultured in serum-free keratinocyte medium, supplemented with 5 ng/ml epidermal growth factor and 35 to 50 μg/ml bovine pituitary extract (Invitrogen, Grand Island, N.Y.) at 37° C., 5% CO2, all other fresh specimens were cultured in RPMI 1640 medium (Invitrogen) containing 10% fetal bovine serum (FBS; Gemini Bio-products, Calabasas, Calif.), 200 u/ml penicillin, and 200 μg/ml streptomycin, as previously described (115,19, 116). All samples were obtained with appropriate consent according to IRB guidelines. Tumors were staged according to the F.I.G.O. operative staging system. Radical tumor debulking, including a total abdominal hysterectomy and omentectomy, was performed in all ovarian carcinoma patients while normal tissues was obtained from consenting similar age donors undergoing surgery for benign pathology. Tumors were established after sterile processing of the samples from surgical biopsies as previously described for ovarian and cervical carcinoma specimens (115,19,116), while normal ovarian tissue was obtained by scraping epithelial cells from the ovarian surface. Briefly, viable tumor tissue was mechanically minced in RPMI 1640 to portions no larger than 1-3 mm$^3$ and washed twice with RPMI 1640. The portions of minced tumor were then placed into 250 ml flasks containing 30 ml of enzyme solution [0.14% collagenase Type I and 0.01% DNAse 2000 KU/mg; (Sigma)] in RPMI 1640, and incubated on a magnetic stirring apparatus overnight at 4° C. Enzymatically dissociated tumor was then filtered through 150 μm nylon mesh to generate a single cell suspension. The resultant cell suspension was then washed twice in RPMI 1640 plus 10% FBS. The epithelial nature and the purity of epithelial tumor cultures was verified by immunohistochemical staining and flow cytometric analysis with antibodies against cytokeratin as previously described (115,19,116). RNA extraction was performed at a tumor cell confluence of 50% to 80% after a minimum of two to a maximum of ten passages in vitro. Only primary cultures which had at least 90% viability and contained >99% epithelial cells were used for sensitivity to CPE in vitro.

TABLE 6

| Patient | Age | Grade | Stage | Histology |
|---------|-----|-------|-------|-----------|
| OSPC 1* | 42 | G2/3 | IV A | OSPC |
| OSPC 2 | 67 | G3 | III B | OSPC |
| OSPC 3 | 61 | G3 | III C | OSPC |
| OSPC 4* | 60 | G3 | III C | OSPC |
| OSPC 5 | 59 | G2/3 | III C | OSPC |
| OSPC 6* | 72 | G3 | IV A | OSPC |
| OSPC 7 | 63 | G3 | III C | CC |
| OSPC 8 | 74 | G2/3 | III C | CC |
| OSPC 9 | 68 | G3 | III B | CC |
| OSPC 10 | 77 | G2/3 | III C | CC |
| OVA 11 | 65 | G3 | IIIC | CC |
| OVA 12R | 81 | G3 | IV A | OSPC |
| OVA 13R | 62 | G3 | IV A | OSPC |
| OVA 14R | 58 | G3 | IIIC | OSPC |

*Patients from which matched chemotherapy naïve and chemotherapy resistant/recurrent disease were both available. OVA-R: Patients with chemotherapy resistant/recurrent disease. OSPC: ovarian serous papillary carcinoma; CC: clear cell ovarian carcinoma.

CPE Treatment of Cell Lines and Trypan Blue Exclusion Test.

Tumor samples and normal control cells were seeded at a concentration of $1 \times 10^5$ cells/well into 6-well culture plates (Costar, Cambridge, Mass.) with the appropriate medium. Adherent tumor samples, fibroblasts and normal epithelial control cell lines were grown to 80% confluence. After washing and renewal of the medium, CPE was added to final concentrations ranging from 0.03 to 3.3 μg/mL. After incubation for 60 minutes to 24 hrs at 37° C., 5% $CO_2$, floating cells were removed and stored, and attached cells were trypsinized and pooled with the floating cells. After staining with trypan blue, viability was determined by counting the number of trypan blue-positive cells and the total cell number.

SCID Mouse Tumor Xenografts and CPE Treatment.

C.B-17/SCID female mice 5-7 weeks old (16-18 g in weight) were obtained from Harlan Sprague-Dawley (Indianapolis, Ind.) and housed in a pathogen-free environment at the University of Arkansas for Medical Sciences (UAMS). They were given commercial basal diet and water ad libitum. The experimental protocol for the use of these animals for these studies was approved by the UAMS Institutional Animal Care and Use Committee. Animals were used to generate ovarian tumor xenografts. The OVA-1 cancer cell line was injected intraperitoneally (i.p.) at a dose of 5 to $7.5 \times 106$ into C.B-17/SCID mice in groups of five. In the first set of experiments (i.e., large ovarian tumor burden challenge), four weeks after i.p. tumor injection, mice were injected i.p. with 5.0, 5.5, 6.5 μg of CPE dissolved in 1 ml of sterile saline at 72 hrs intervals. In a second set of experiments, groups of five mice received 7.5 μg or 8.5 μg of CPE i.p. at 72 hrs intervals 1 week after i.p. OVA-1 tumor injection at a dose of $5 \times 10^6$ tumor cells. All animals were observed twice daily and weighed weekly, and survival was monitored. In addition, groups of mice injected i.p. at a dose of 5 to $7.5 \times 10^6$ OVA-1 tumor cells were killed at one, two, three and four weeks for necropsy and pathologic analysis. The remaining animals were killed and examined just before they died of intraperitoneal carcinomatosis and malignant ascites.

Statistics.

Statistical differences in claudin-3 and claudin-4 expression between chemotherapy naïve and chemotherapy recurrent/resistant ovarian tumors were tested using the student t test. For the OVA-1 animal model, survivals were plotted using Kaplan-Meier methods and compared using the log-rank test. A p value less than 0.05 (p<0.05) was used for statistical significance.

Results

Claudin-3 and Claudin-4 Transcript Levels in Chemotherapy Sensitive and Chemotherapy Resistant Ovarian Tumors.

Figure 6A:
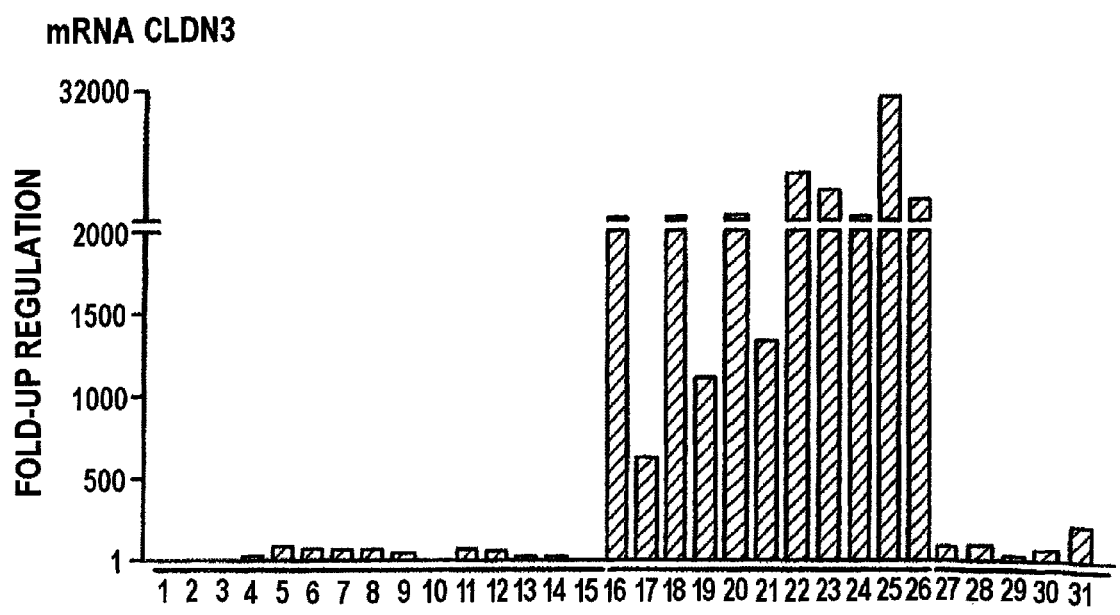
FIGS. 6A and B. Quantitative RT-PCR analysis of claudin-3 and claudin-4 expression. The Y axis represents the fold induction relative to normal ovary expression (sample 1). The X axis represents each sample tested for claidin-3 (FIG. 6A) and claudin-4 (FIG. 6B). The first 15 bars represent normal ovarian epithelium (1-3), normal endometrial epithelium (4-6), normal cervical keratinocytes (7), primary squamous cervical cancer cell lines (8-10), primary adenocarcinoma cervical cancer cell lines (11-13), Epstein-Barr transformed B lymphocytes (LCL) (14), and human fibroblasts (15). The following 16 bars represent primary ovarian cancer cell lines (16-21 serous papillary ovarian cancers, 22-26 clear cell ovarian tumors) and established serous ovarian cancer cell lines, 27-31 (i.e., UCI 101, UCI 107, CaOV3, OVACAR-3, and OVARK-5).
Figure 6B:
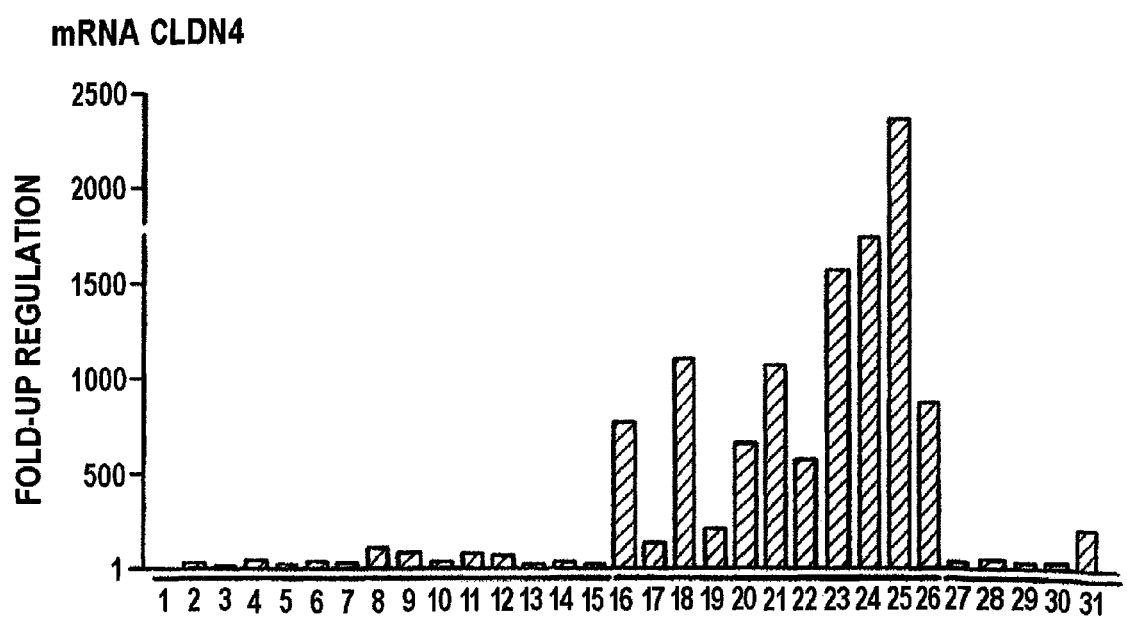
Figure 7C:
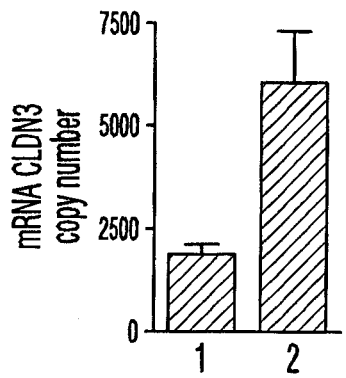
FIGS. 7C and 7D: 1 (chemotherapy naïve) and 2 (chemotherapy resistant) represent claudin-3 and claudin-4 expression in autologous matched OVA-1 tumors. 3 (chemotherapy naïve) and 4 (chemotherapy resistant) represent claudin-3 and claudin-4 expression in autologous matched OVA-4 tumors. 5 (chemotherapy naïve) and 6 (chemotherapy resistant) represent claudin-3 and claudin-4 expression in autologous matched OVA-6 tumors.
Figure 7C:
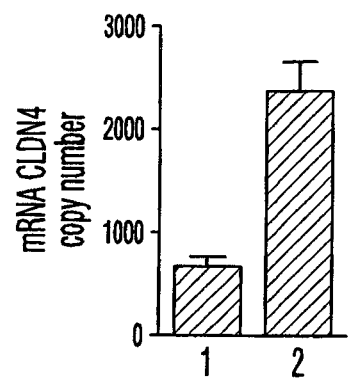
Figure 7C:
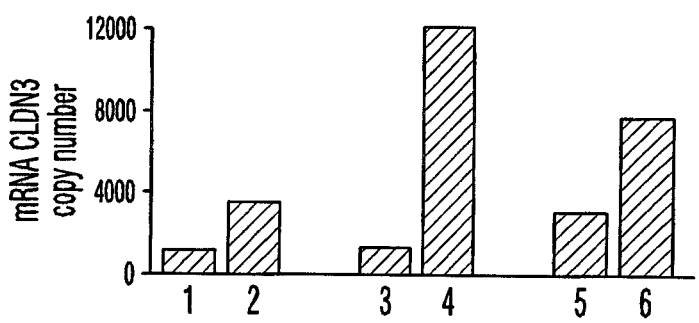
Figure 7D:
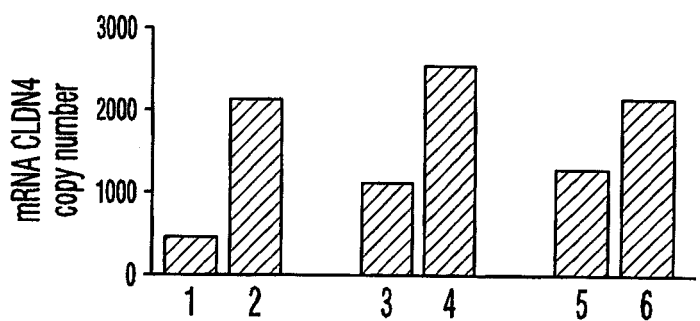

Quantitative RT-PCR assays were used to get highly sensitive measurements of claudin-3 and claudin-4 expression in normal tissues and fresh and established human tumors. Both claudin-3 and/or claudin-4 genes were highly expressed in all primary ovarian cancers studied when compared with normal ovarian epithelial cells as well as other normal cells or other gynecologic tumors (FIG. 6). Of interest, established ovarian cancer cell lines (UCI 101, UCI 107, CaOV3, OVACAR-3, OVARK-5), were found to express much lower levels of claudin-3 and/or claudin-4 compared to primary ovarian tumors (FIG. 6). Finally, claudin-3 and/or claudin-4 expression was extremely low in all control tissues examined including normal ovarian epithelium, normal endometrial epithelium, normal cervical keratinocytes, and normal human fibroblasts (FIG. 6).

When OSPC collected at the time of primary debulking surgery (6 cases) were compared for claudin-3 and/or claudin-4 receptor expression to those collected at the time of tumor recurrence after multiple courses of chemotherapy (6 cases), chemotherapy resistant tumors were found to express significantly higher levels of claudin-3 and/or claudin-4 receptors (p<0.05, FIG. 7). Importantly, when 3 primary ovarian cancers naïve to chemotherapy were compared to recurrent ovarian cancers recovered from the same patients following chemotherapy (i.e., matched autologous tumor samples), chemotherapy resistant tumors were again found to express higher levels of claudin-3 and claudin-4 (FIG. 7).

Claudin-3 and Claudin-4 Transcript Levels in Metastatic and Primary Tumors.

Figure 8A:
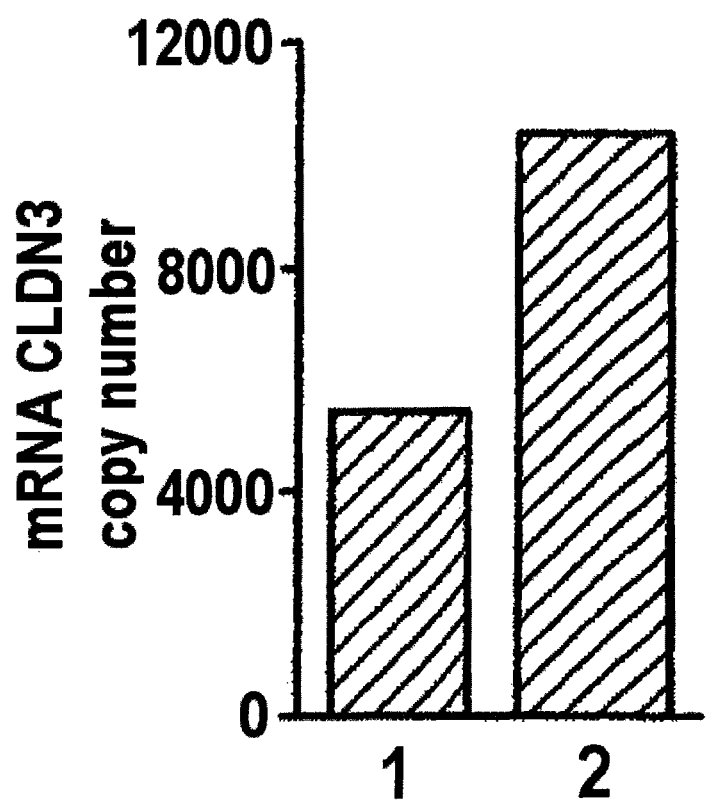
FIGS. 8A and B. Quantitative RT-PCR analysis of claudin-3 (FIG. 8A) and claudin-4 (FIG. 8B) expression in primary vs. metastatic ovarian cancer tumors. The Y axis represents the fold induction of claudin-3 (FIG. 8A) and claudin-4 (FIG. 8B) relative to normal ovary expression. The sample tested is indicated on the X axis as (1) OVA-1 primary tumor, and (2) OVA-1 metastatic tumor.
Figure 8B:
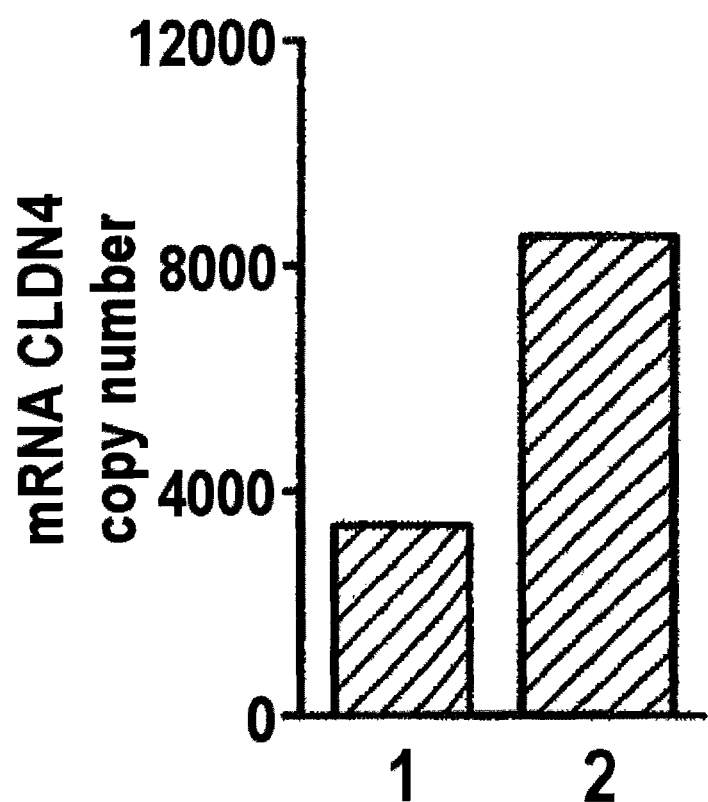

Claudin-3 and claudin-4 mRNA copy numbers were quantified in an OVA-1 primary tumor and in a metastatic ovarian tumor (omentum metastasis) later taken from the same patient. The results are shown in FIG. 8. Transcript levels for both claudin-3 and claudin-4 were more than twice as high in the metastatic cells as in the primary tumor.

Claudin-4 Expression by Immunohistology on OSPC and NOVA Tissue Blocks.

To determine whether the high expression of the claudin-4 gene detected by q-RT-PCR assays in primary ovarian cancer cell lines is the result of a selection of a subpopulation of cancer cells present in the original tumor, or whether in vitro expansion conditions may have modified gene expression, immunohistochemical analysis of claudin-4 protein expression was performed on formalin fixed tumor tissue from the uncultured primary surgical specimens from which fresh ovarian cancers were derived. As shown in Table 7, moderate to heavy membranous staining for claudin-4 protein expression was noted in all the cancer specimens that overexpressed the claudin-4 transcript. In contrast, negative or low staining was found in all the normal ovarian epithelium tested by immunohistochemistry (Table 7).

TABLE 7

| Claudin-4 staining | |
|---|---|
| Patient | Claudin-4 positivity |
| NOVA 1 | 1+ |
| NOVA 2 | 1+ |

TABLE 7-continued

| Claudin-4 staining | |
|---|---|
| Patient | Claudin-4 positivity |
| OVA 1 | 3+ |
| OVA 2 | 3+ |
| OVA 3 | 3+ |
| OVA 4 | 2+ |
| OVA 5 | 3+ |
| OVA 6 | 2+ |
| OVA 7 | 3+ |
| OVA 8 | 2+ |
| OVA 9 | 3+ |
| OVA 10 | 3+ |
| OVA 11 | 3+ |

Effects of CPE on Fresh Ovarian and Cervical Cancer Cell Lines and Normal Control Cells.

Figure 9:
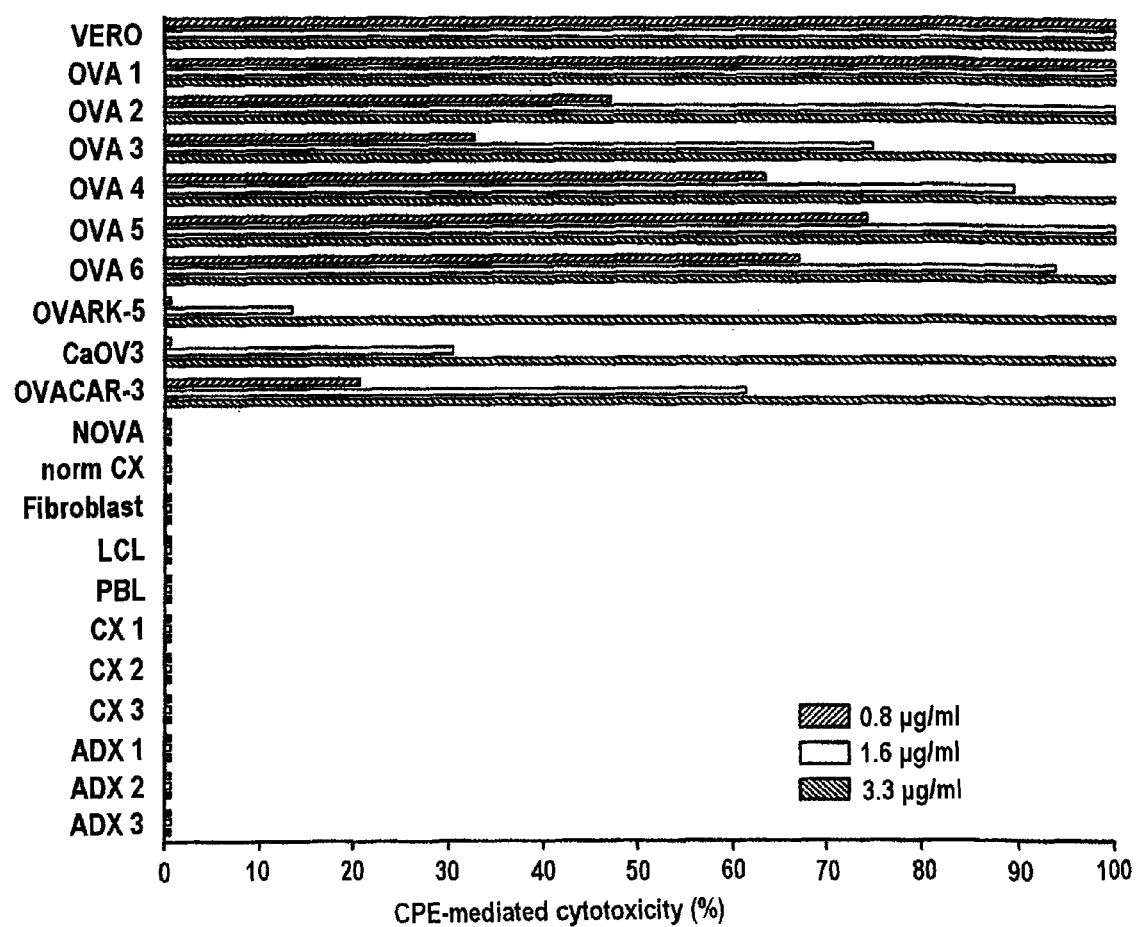
FIG. 9. Representative dose dependent CPE-mediated cytotoxicity of primary ovarian cancers compared to positive control Vero cells or negative controls (i.e., normal and neoplastic cells) after 24 hrs exposure to CPE. VERO: positive control cells. OVA-1 to OVA-6: primary ovarian tumors. OVARK-5, CaOV3, OVACAR-3: established serous ovarian tumors. Nova: normal ovarian epithelium. Norm CX: normal cervix keratinocytes. Fibroblast: normal human fibroblasts. LCL: lymphoblastoid B-cells. PBL: normal peripheral blood lymphocytes. CX1-3: primary squamous cervical cancer. ADX1-3: primary adenocarcinoma cervical cancer.

On the basis of the high expression of claudin-3 and/or claudin-4 on primary ovarian cancer cell lines, it was suspected that ovarian tumors expressing either claudin-3 or claudin-4 would be sensitive to CPE-mediated lysis. It was important to demonstrate this directly on fresh human ovarian carcinoma cells, particularly in a clinically relevant setting of ovarian cancer disease for which current salvage therapies are ineffective (i.e., chemotherapy resistant disease). For this reason this study examined short term in vitro primary cultures of ovarian carcinomas obtained either from chemotherapy nave patients (i.e., OVA-2, OVA-3 and OVA-5) or patients heavily treated with different combinations of chemotherapy (i.e., OVA-1, OVA-4 and OVA-6) and now with disease progression after multiple chemotherapy regimens. The sensitivity of these primary ovarian tumor cultures to CPE-mediated cytolysis was tested along with an appropriate claudin-3 and claudin-4-expressing positive control (i.e., Vero cells), established OSPC cell lines (OVARK-5, CaOV3 and OVACAR-3), and negative controls which do not express detectable levels of either claudin-3 or claudin-4. As shown in FIG. 9, regardless to their sensitivity or resistance to chemotherapy all ovarian tumors tested were found sensitive to CPE-mediated cytolysis. The cytotoxic effect was dose dependent and was positively correlated to the levels of either claudin-3 or claudin-4 expression as tested by RT-PCR in tumor samples. Importantly, although ovarian tumors demonstrated different sensitivities to CPE exposure, no ovarian cancer was found viable after 24 hrs exposure to CPE at the concentration of 3.3 µg/mL. In contrast, all normal controls tested including ovarian epithelium, cervical keratinocytes and mononuclear cells as well as cervical cancer cell lines lacking claudin-3 or claudin-4 were not affected by CPE (FIG. 9).

Effect of CPE on Chemotherapy Resistant Ovarian Cancer Cells In Vivo

For in vivo confirmation of the in vitro data, xenograft tumors in SCID mice were developed by i.p. injection with OVA-1, a primary ovarian tumor resistant to multiple chemotherapeutic agents in vitro (by EDR assay) as well as in vivo. Primary OVA-1 tumor cells grew progressively as numerous serosal nodules adherent to virtually all intraabdominal organs (peritoneum, omentum, diaphragm, bowel, liver, pancreas, spleen) and exhibited the capacity for local tissue invasion and formation of malignant ascites after 2 to 3 weeks from injection. Tumors first appeared grossly by the second week as small nodules on the omentum and continuously grew to form a confluent omental mass by the time the animals died (i.e., mean survival 38 days after i.p. injection with 7.5×10⁶ OVA-1 cells). Necropsies revealed massive hemorrhagic ascites and numerous tumor nodules, measuring 1 to 8 mm in diameter, studding the entire peritoneal surface and implanting the serosa of virtually all intraabdominal organs.

Figure 10A:
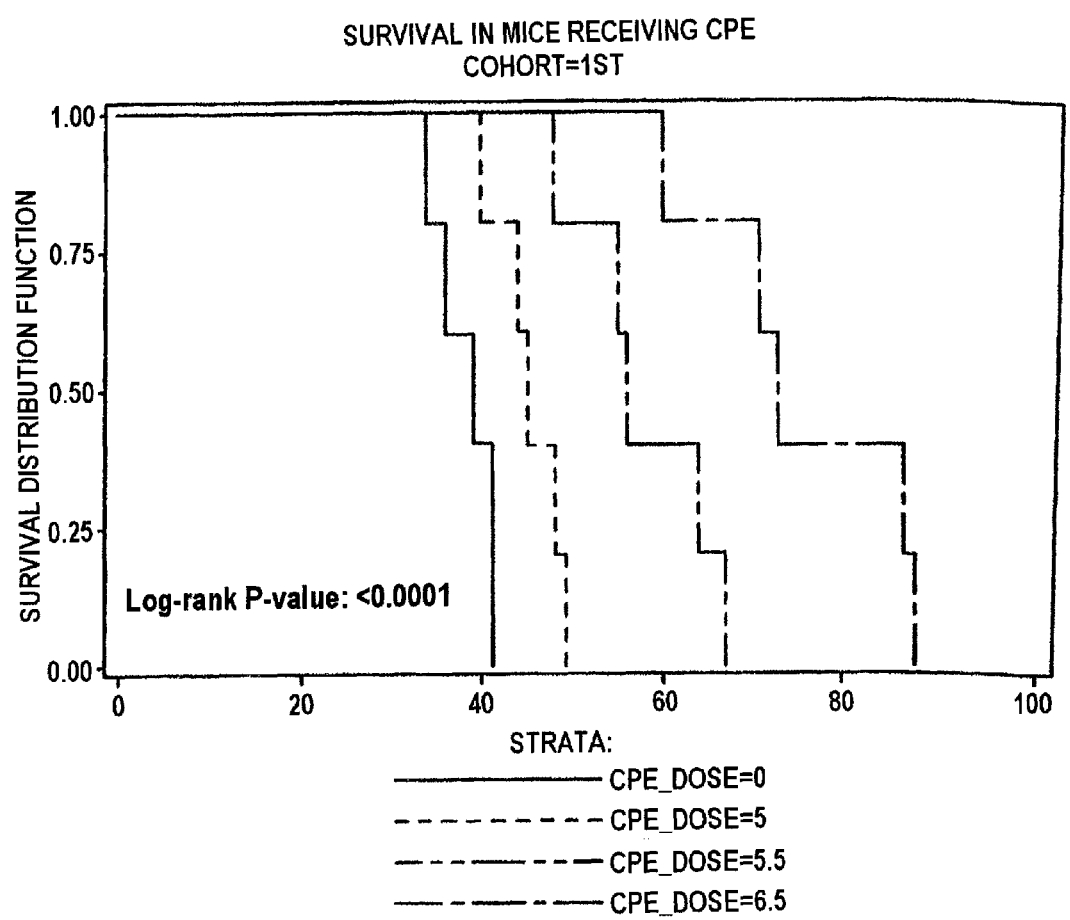
FIGS. 10A and B. Survival of C.B-17/SCID Mice after i.p. injection of $5-7.5 \times 10^6$ viable OVA-1 tumor cells. Animals harboring four-week (A) and one-week (B) established OVA-1 tumors were injected i.p. with doses of CPE ranging from 5 to 8.5 µg as described in the material and methods. CPE was administered i.p. every 72 hrs until death or end of study. Mice were evaluated on a daily basis and sacrificed when moribund. In both studies, the log-rank test yielded $p<0.0001$ for the differences in survival.
Figure 10B:
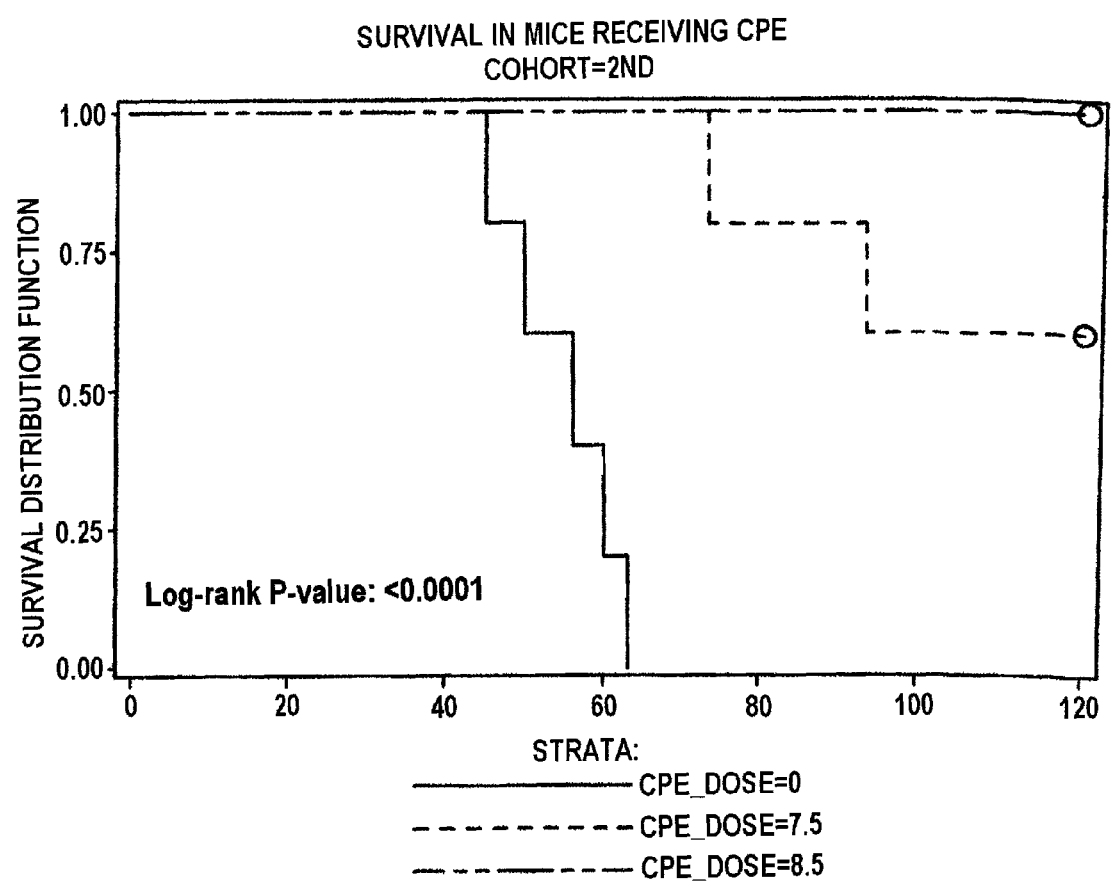

Previous toxicology studies in mice have reported 0.5 µg/g of CPE administered i.p. to be a well tolerated and safe dose in 100% of the animals (i.e., 16.5±1.0 g male SW mice) (117,118). In contrast, some animals injected with 0.75 µg died after CPE injection and all animals injected with 1 µg/g of CPE died within 1 to 2 hrs (117,118). Maximum tolerated dose in healthy female mice was determined and is consistent with these observations (data not shown). In one experiment, groups of mice harboring large ovarian tumor burden xenografts (i.e., four weeks after OVA-1 tumor injection) were treated with repeated i.p. CPE injections every 72 hrs at three different doses (5.0 µg, 5.5 µg or 6.5 µg). Control mice harboring OVA-1 received saline alone. CPE injections were well tolerated, and no adverse events were observed throughout the complete treatment protocol either in control mice receiving CPE alone or CPE-treated mice harboring large tumor burden. Mice harboring OVA-1 treated with saline all died within 6 weeks from tumor injection with a mean survival of 38 days (FIG. 10A). In contrast, animals treated with multiple CPE injections survived significantly longer than control animals did (p<0.0001, FIG. 10A). The increase in survival in the different groups of mice treated with the diverse doses of CPE was clearly dose dependent, with the highest dose injected (i.e., 6.5 µg every 72 hrs) found to provide the longer survival (FIG. 10A). In another set of experiments, mice harboring OVA-1 (a week after tumor injection with 5×10⁶ cells) were treated with i.p. CPE injections at a dose ranging from 7.5 µg to 8.5 µg every 72 hrs. While mice harboring OVA-1 treated with saline all died within 9 weeks from tumor injection (FIG. 10B), three out of five (60%) of mice receiving 7.5 µg doses of CPE and five out of five (100%) of mice receiving 8.5 µg doses of CPE by multiple i.p. injections remained alive and free of detectable tumor for the duration of the study period (i.e., over 120 days, p<0.0001).

Discussion

In this study, after having confirmed at both the RNA and protein levels the expression of high levels of CPE receptors in multiple primary ovarian cancers and tested the in vitro sensitivity of tumor cells to CPE therapy, the efficacy and toxicity of i.p. injection of CPE in vivo in a clinically relevant animal model of chemotherapy resistant ovarian tumor xenografts were evaluated.

100% (seventeen out of seventeen) of the primary ovarian cancer cell lines tested for claudin-3 and claudin-4 expression by quantitative RT-PCR overexpress either the high affinity CPE receptor (claudin-4) or the low affinity CPE receptor (claudin-3). Of interest, all the established ovarian cancer cell lines tested (UCI 101, UCI 107, CaOV3, OVACAR-3, OVARK-5), were found to express much lower levels of claudin-3 and/or claudin-4 compared to primary ovarian tumors. These data suggest that prolonged in vitro culture may significantly alter claudin-3 and claudin-4 gene expression in ovarian cancer. In addition, q-RT-PCR showed a consistent downregulation of claudin-3 and claudin-4 expression levels in the more advanced in vitro passages of primary OSPC (data not shown). Thus, established ovarian cancer cell lines may represent suboptimal models to evaluate the potential of CPE-mediated therapy against ovarian cancer in vitro as well as in vivo. Importantly, all primary ovarian tumors evaluated, including those found to be resistant to chemotherapy in vivo as well as in vitro, were found highly sensitive to CPE-mediated killing in vitro. In this regard, although ovarian tumors demonstrated different sensitivity to CPE exposure, no ovarian cancer was found viable after 24 hrs exposure to CPE at the concentration of 3.3 µg/mL, a dose well tolerated by in vivo i.p. administration of CPE in these experiments. This was in strong contrast with the lack of sensitivity of normal ovarian epithelium as well as other normal control cells to CPE-mediated cytolysis. These findings are likely explained by a limited expression of claudin-3 and claudin-4 in normal epithelia compared to ovarian tumor cells.

When the efficacy of multiple i.p. injection of sublethal doses of CPE in vivo in a clinically relevant animal model of chemotherapy resistant ovarian tumor xenografts was tested, doses of CPE ranging from 5 to 8.5 µg were well tolerated, and no adverse events were observed throughout the complete treatment protocol either in control mice receiving CPE alone or CPE-treated mice harboring small and large tumor burden. These data demonstrate that CPE doses found effective in vitro to kill ovarian tumor cells may be safely administered i.p. in mice harboring ovarian cancer disease. More importantly, survival of mice harboring a large burden of chemotherapy resistant ovarian disease was significantly prolonged in a dose dependent manner by repeated i.p. injections of CPE. Finally, when animals harboring 1 week OVA-1 xenografts were treated with repeated i.p. injections of CPE, most of the mice remained alive and free of detectable tumor for the duration of the study (i.e., over 120 days). Collectively, these results provide strong evidence that CPE-based therapy can be useful in the treatment of ovarian cancer patients refractory to standard treatment modalities.

CPE probably must distribute through a tumor by passive diffusion. So intraperitoneal CPE administration would likely be most effective in patients with microscopic residual disease or small tumor burden.

CPE-mediated cytolysis requires only the single step of CPE binding to its receptors and takes place after only a few minutes of tumor cell exposure to toxic CPE concentrations. Thus, the simplicity and rapidity of CPE-mediated cytolysis may result in increased efficacy, reduced opportunity for the development of resistance, and the possibility that high local concentrations of CPE may need to be maintained for only a relatively short period of time. Furthermore, because the efficacy of CPE therapy against chemotherapy resistant ovarian cancer xenografts has been demonstrated in SCID mice (i.e., severely immunocompromised animals), it seems unlikely that the host immune system is required to play a significant role in the in vivo efficacy of CPE therapy. This point is noteworthy because several biologic response modifiers previously used for the therapy of chemotherapy resistant ovarian cancer, including cytokines (119) and humanized monoclonal antibodies (120), unlike CPE therapy, rely for most of their efficacy on the activation of an uncompromised host immune system (121), a major limitation when dealing with elderly ovarian cancer patients heavily pretreated with multiple regimens of immunosuppressive chemotherapy.

In conclusion, it is shown that primary and metastatic ovarian cancers that have acquired in vivo resistance to chemotherapeutic drugs are susceptible to killing by CPE-mediated therapy in vitro as well as in vivo.

Conclusions

100% (17 out of 17) of the primary ovarian tumors tested overexpressed one or both CPE-receptors by quantitative RT-PCR. All ovarian tumors demonstrated a dose-dependent cytotoxic effect to CPE in vitro. Importantly, chemotherapy resistant/recurrent ovarian tumors were found to express claudin-3 and claudin-4 genes at significantly higher levels when compared to chemotherapy naïve ovarian cancers and all primary ovarian tumors tested, regardless of their resistance to chemotherapeutic agents, died within 24 hrs to the exposure to 3.3 µg/mL of CPE in vitro. Metastatic OVA-1 tumors were also found to express more claudin-3 and claudin-4 than primary OVA-1 tumors. In addition, the in vivo efficacy of intraperitoneal (i.p.) CPE therapy in SCID mouse xenografts was studied in a highly relevant clinical model of chemotherapy resistant freshly explanted human ovarian cancer (i.e., OVA-1). Repeated i.p. administration of sublethal doses of CPE every 3 days significantly inhibited tumor growth in 100% of mice harboring 1-week established OVA-1. Repeated i.p. doses of CPE also had a significant inhibitory effect on tumor progression with extended survival of animals harboring large ovarian tumor burdens (i.e., 4-weeks established OVA-1).

Example 4

Production of a Chimeric Antibody Containing a Claudin-Binding Peptide of CPE In this Example, production of a chimeric antibody having residues 290-319 of SEQ ID NO:1 (CPE), which is a peptide of CPE that binds to claudin-3 and claudin-4, conjugated to the Fc portion of IgG1.

A nucleic acid segment encoding residues 290-319 of SEQ ID NO:1 is cloned into vector pFUSEhFc2(IL2ss) (SEQ ID NO:2) (INVIVOGEN company, www.invivogen.com).

Two single-stranded oligonucleotides 30-CPE-forward (SEQ ID NO:3) and 30 CPE-reverse (SEQ ID NO:4) are synthesized. Annealing the two strands produces a double-stranded DNA segment with a blunt end and an NcoI-compatible sticky end (a CATG-5' overhang).

pFUSEhFc2 is digested with EroRV and NcoI. The hybridized insert is ligated into the double-digested pFUSE-hFc2. The result is a vector that expresses a protein with SEQ ID NO:5. Residues 1-21 of SEQ ID NO:5 are a signal peptide of interleukin-2 (ssIL2) for secretion of the expressed protein in mammalian cells. The signal peptide is cleaved during secretion. Residues 23-52 of SEQ ID NO:5 are a claudin-3- and claudin-4-binding peptide from CPE (residues 290-319 of SEQ ID NO:1). Residues 22 and 53 result from insertion of the CPE residues. Residues 54-280 of SEQ ID NO:5 are human Fc (CH2 and CH3 domains and the hinge region of human IgG1 heavy chain).

The plasmid encoding the 30aaCPE-Fc fusion protein is amplified in *E. coli*, and then transfected into the murine myeloma cell line Sp2/0 Ag14 from the American Type Culture Collection for expression and secretion of the 30aaCPE-Fc fusion protein. The secreted fusion protein is purified by protein A or protein G affinity chromatography

REFERENCES CITED

1. Bohkman J V. 1983. Gynecol. Oncol. 15:10-17.
2. Rose P G. 1996. New Engl. J. Med. 335:640-649.
3. Sherman M E et al. 1992. Am. J. Surg. Pathol. 16:600-610.
4. Carcangiu M L et al. 1992. Gynecol. Oncol. 47:298-305.
5. Goff B A et al. 1994. Gynocol. Oncol. 54:264-268.
6. Carcangiu et al. 1995. Int. J. Gynecol. Pathol. 14:30-38.
7. Levenback C et al. 1992. Gynecol. Oncol. 46:317-321.
8. Nicklin J L. et al. 1996. Clin. Obstet. Gynecol. 39:686-695.
9. Trope C et al. 2001. Best Practice & Research in Clinical Obstetrics & Gynaecology 15:433-446.
10. Hendrickson M et al. 1982. Am. J. Surg. Pathol. 6:93-108.
11. Ossowski L et al. 1991. J. Cell Biol. 115:1107-12.
12. Chan J K et al. 2003. Gynecologic Oncology 90:181-185.
13. Tsukita S et al. 2000. Ann. NY Acad. Sci. 915:129-135.
14. Katahira J et al. 1997. J. Cell Biol. 136:1239-47.
15. Katahira J et al. 1997. J. Biol. Chem. 272:26652-58.
16. McClane B A. 1996. Toxicon 34:1335-43.
17. Long H et al. 2001. Cancer Res. 61:7878-81.
18. Michl P et al. 2001. Gastroenterology 121:678-684.
19. Hough C D 2000. Cancer Res. 60:6281-6287.
20. Rangel L B A et al. Clin. Cancer Res. 9:2567-75.
21. McClane B A et al. 1990. Infect. Immun. 58:3109-3115.
22. McClane B A. 1994. Toxicology 87:43-67.
23. Kokai-Kun J F et al. 1996. Infect. Immun. 64:1020-1025.
24. Kokai-Kun J F et al. 1997. Clin. Infect. Dis. 25 (Suppl. 2):S165-S167.
25. Kokai-Kun J F et al. 1997. Infect. Immun. 65:1014-1022.
26. Hanna P C et al. 1991. J. Biol. Chem. 266:11037-43.
27. Kokai-Kun J F et al. 1999. Infect. Immun. 67:5634-41.
28. Riethmuller G et al. 1998. J. Clin. Oncol. 16:1788-94.
29. Zhan F et al. 2002. Blood 99:1745-57.
30. Ismail R S, et al. 2000. Cancer Res. 60:6744-6749.
31. Santin A D, et al. 2000. Obstet. Gynecol. 96:422-430.
32. Fuchtner C. et al. 1993. Gynecol. Oncol. 48: 203-209.
33. Gamboa G et al. 1995. Gynecol. Oncol. 58:336-343.
34. Eisen M B et al. 1998. Proc. Natl. Acad. Sci. USA 95:14863-68.
35. Packeisen J et al. Hybridoma 18:37-40.
36. Welsh J B et al. 2001. Proc. Natl. Acad. Sci. USA 98:1176-1181.
37. Ono K et al. 2000. Cancer Res. 60: 5007-11.
38. Shridhar V et al. 2001. Cancer Res. 61:5895-904.
39. Hough C D et al. 2001. Cancer Res. 6:3869-76.
40. Shridhar V et al. 2002. Cancer Res. 62:262-70.
41. Jazaeri A A et al. 2003. Mol. Carcinogenesis 36:53-9.
42. Maatta M et al. 2001. J. Histochem. & Cytochem. 49:711-26.
43. Casey R C et al. 2000. Clinical & Experimental Metastasis 18:67-75.
44. Yoshida Y et al. 2001. Inter. J. Oncol. 18:913-21.
45. Koshikawa N et al. 1999. Cancer Res. 59:5596-601.
46. Vollmers H P et al. 1984. FEBS Letters 172:17-20.
47. Iwamoto Y et al. 1987. Science 238:1132-4.
48. Linnenbach A J et al. 1993. Mol. & Cell Biol. 13:1507-15
49. Litvinov S V et al. 1994. J. Cell Biol. 125:437-46
50. Morita K et al. 1999. Proc. Natl. Acad. Sci. USA 96:511-6.
51. McClane B A. 2001. Toxicon 2001, 39:1781-1791.
52. Ganesh S et al. 1995. Cancer Res. 54:4065-71.
53. Hasina R et al. 2003. Cancer Res. 2003; 63:555-9.
54. Dickinson J L et al. 1995. J. Biol. Chem. 270:27894-904.
55. Chambers S K et al. 1997. Int. J. Cancer 74: 71-575.
56. Chambers S K et al. 1997. Clin. Canc. Res. 3:999-1000.
57. Droz D et al. 1990. Am. J. Pathol. 137:895-905.
58. Raife T J et al. 1994. Am. J. Clin. Pathol. 101:296-299.
59. Jackson D et al. 1992. Cancer Res. 52:5264-5270.
60. Huang L R et al. 1995. Cancer Res. 55:4717-4721.

61. Senner V et al. 1999. J. Neuropathol. Exp. Neurol. 58:795-802.
62. Fogel M et al. 1999. Cancer Lett. 143:87-94.
63. Aigner S et al. 1997. Blood 89:3385-3395.
64. Aigner S et al. 1998. EMBO J. 12:1241-1251.
65. Friederichs J et al. 2000. Cancer Res. 60:6714-6722.
66. Bratt T et al. 2000. Biochimica et Biophysica Acta 1482:318-26.
67. Flower D R. 1996. Biochemical Journal 318:1-14.
68. Oates A J et al. 1997. Invasion & Metastasis 17:1-15.
69. Koeneman K S et al. 1999. Prostate 39:246-61.
70. Chambers A F et al. 1996. Lung Cancer 15:311-23.
71. Denhardt D T et al. 2003. Clinical & Experimental Metastasis 20: 77-84.
72. Kim J H et al. 2002. JAMA 287:1671-9.
73. Diamandis, E P et al. 2002. Clinical Chemistry 48:1198-205.
74. Tanimoto H et al. Cancer 86:2074-82.
75. Tanimoto H et al. 2001. Tumor Biology 22:104-14.
76. Tanimoto H et al. 2001. Tumor Biology 2001; 22:11-8.
77. Diamandis E P et al. 2003. J. Clin. Oncol. 21:1035-43.
78. Cannon M J et al. 2002. Expert Review of Anticancer Therapy 2:97-105.
79. Liu Y et al. 2002. Reproduction 123:341-353.
80. Santin A D et al. 2002. Brit J Cancer 86(1):151-7.
81. Bongso A et al. 1988. Human Reproduction 3(6):705-13.
82. Meresman G F et al. 2003. Fertility & Sterility 80 Suppl 2:702-7.
83. Quelle D E et al. 1995. Cell 83(6):993-1000.
84. Moll U M et al. 1996. Human Pathology 27(12):1295-300.
85. Kovalev S et al. 1998. Human Pathology 29(6):613-9, 1998.
86. Salvesen H B et al. 2000. Clinical Cancer Research 6(1):153-9.
87. Sano T et al. 2002. Path. Intern. 52(5-6):375-83.
88. Khleif S N et al. 1996. Proc. Natl. Acad. Sci. USA. 93(9):4350-4.
89. Terris B et al. 2002. Am. J. Pathol. 160:1745-54.
90. Seth P et al. 2002. Cancer Research 62:4540-4.
91. Luo L Y et al. 2003. Cancer Research. 63(4):807-11.
92. Janes P W et al. 1997. J. Biol. Chem. 272:8490-7.
93. Santin A D et al. 2002. Clin. Cancer Res 8:1271-9.
94. Santin A D et al. 2003. Gynecol. Oncol. 88:263-5.
95. Santin A D et al. Gynecol. Oncol. 92(1):387.
96. Lukes A S et al. 1994. Cancer 73(9):2380-5.
97. Bristow, R E et al. 2004. Gynecol. Oncol. 92; 480; Abs 194.
98. Slamon D L et al. 2001. N. Engl. J. Med. 344:783-79.
99. Villella J A et al. 2003. Proc. Am. Soc. Clin. Oncol. Abs No: 1870.
100. Hortsch M. 1996. Neuron 17(4):587-93.
101. Patel K et al. 1991. Hybridoma 10(4):481-91.
102. Linnemann D et al. 1989. International Journal of Cancer 43(4):709-12.
103. Katayama M et al. 1997. Cell Structure & Function 22(5):511-6.
104. Fogel M et al. 2003. Lancet 362(9387):869-75.
105. Gutwein P et al. 2003. FASEB Journal 17(2):292-4.
106. Tian E et al. 2003. New Engl. J. Med. 349(26):2483-94.
107. Ossowski L et al. 1991. Journal of Cell Biology 115(4):1107-12.
108. Xing R H et al. 1996. International Journal of Cancer 67(3):423-9.
109. Rabbani S A et al. 2001. Surgical Oncology Clinics of North America 10(2):393-415.
110. Memarzadeh S et al. 2002. Proc Natl Acad Sci USA 99(16):10647-52.
111. Riisbro R et al. 2002. Clin Cancer Research 8(5):1132-41.
112. Rabbani S A et al. 2002. Cancer Research 62(8):2390-7.
113. Liu Y et al. 2002. Reproduction 123:341-353.
114. Holloway R W et al. 2002. Gynecol Oncol. 87:8-16.
115. Santin A D et al. 2000. Am. J. Obstet. Gynecol. 183: 601-609.
116. Santin A D et al. 1999. Journal of Virology 3: 5402-5410.
117. Niilo L et al. 1975. Infect. Immun. 12: 440-442.
118. Wallace F M et al. 1999. Current Microbiology 38:96-100.
119. Berek J S. 2000. Lancet 356:6-7.
120. Bookman M A et al. 2003. J. Clin. Oncol. 21:283-90.
121. Clynes R et al. 1998. Proc. Natl. Acad. Sci. USA 95:652-656.
122. Casey, J L et al. 1996. Br. J. Cancer 74:1397-1405.
123. Lustgarten, J. et al. 1999. J. Immunol. 162:359-365.

All patents, patent documents, and other references cited are hereby incorporated by reference.

What is claimed is:

1. A method of determining the sensitivity of a malignancy in a patient to *Clostridium perfringens* enterotoxin (CPE) therapy and treating said malignancy wherein said malignancy is recurrent ovarian serous papillary carcinoma, recurrent ovarian clear cell carcinoma or recurrent uterine serous papillary carcinoma and wherein said recurrent malignancy includes chemotherapy-resistant malignant cells, comprising detecting the presence of claudin-3 and/or claudin-4 in a sample portion of said malignancy from said patient; determining that the patient has a significantly higher expression level of claudin-3 and/or claudin-4 in said chemotherapy-resistant malignant cells compared to chemotherapy naïve malignant cells, wherein a significantly higher expression level of claudin-3 and/or claudin-4 in said chemotherapy-resistant malignant cells compared to said chemotherapy naive malignant cells is evidence that the malignancy is sensitive to CPE therapy; and treating said patient for said malignancy by administering to said patient a therapeutically effective amount of *Clostridium perfringens* enterotoxin (CPE) or a pharmaceutically effective salt thereof;

wherein the CPE is native CPE (SEQ ID NO:1) or a variant thereof comprising a sequence at least 90% identical to residues 45-319 of SEQ ID NO:1;

wherein the CPE or a pharmaceutically acceptable salt thereof is administered intravenously or intraperitoneally and wherein the CPE preferably binds to chemotherapy-resistant cancerous cells over chemotherapy-sensitive cancer cells.

2. The method according to claim 1 wherein the detecting step comprises contacting the sample portion of said malignancy with a protein or its pharmaceutically acceptable salt comprising residues 290-319 of SEQ ID NO:1 or a fragment thereof that binds specifically to claudin-3 and/or claudin-4.

3. The method of claim 2 wherein the protein is CPE or a pharmaceutically acceptable salt thereof.

4. The method of claim 2 wherein the protein is an antibody comprising an Fc coupled to an antigen-binding peptide comprising residues 290-319 of SEQ ID NO:1 or a fragment thereof that binds specifically to claudin-3 and/or claudin-4.

5. The method of claim 1 wherein the cancer is ovarian serous papillary carcinoma.

6. The method of claim 1 wherein the cancer is uterine serous papillary carcinoma.

7. The method of claim 1 wherein the cancer is ovarian clear cell carcinoma.

8. The method according to claim 1 wherein the CPE or pharmaceutically acceptable salt used to treat said malignancy is administered intraperitoneally.

9. The method according to claim 1 wherein the CPE or pharmaceutically acceptable salt used to treat said malignancy is administered intravenously.

10. The method according to claim 1 wherein the CPE administered to said patient to treat said malignancy consists of SEQ ID NO:1.

11. The method according to claim 10 wherein the CPE is an engineered CPE.

12. The method according to claim 1 further comprising administering to said patient a protective agent that protects cells against CPE toxicity wherein the protective agent comprises residues 290-319 of SEQ ID NO:1 or a fragment thereof that binds specifically to claudin-3 and/or claudin-4.

13. The method according to claim 1 wherein said CPE is administered to said patient intravenously.

14. The method according to claim 1 wherein said CPE is administered to said patient intraperitoneally.

* * * * *

SEQUENCE LISTING

```
<160> NUMBER OF SEQ ID NOS: 7

<210> SEQ ID NO 1
<211> LENGTH: 319
<212> TYPE: PRT
<213> ORGANISM: Clostridium perfirngens
<300> PUBLICATION INFORMATION:
<308> DATABASE ACCESSION NUMBER: AAA72120
<309> DATABASE ENTRY DATE: 1993-04-26
<313> RELEVANT RESIDUES IN SEQ ID NO: (1)..(319)

<400> SEQUENCE: 1

Met Leu Ser Asn Asn Leu Asn Pro Met Val Phe Glu Asn Ala Lys Glu
1               5                   10                  15

Val Phe Leu Ile Ser Glu Asp Leu Lys Thr Pro Ile Asn Ile Thr Asn
            20                  25                  30

Ser Asn Ser Asn Leu Ser Asp Gly Leu Tyr Val Ile Asp Lys Gly Asp
        35                  40                  45
```

| | | | | | | | | | | | | |
|---|---|---|---|---|---|---|---|---|---|---|---|---|
|Gly|Trp|Ile|Leu|Gly|Glu|Pro|Ser|Val|Val|Ser|Ser|Gln|Ile|Leu|Asn|
| |50| | | |55| | | |60| | | | |

Pro Asn Glu Thr Gly Thr Phe Ser Gln Ser Leu Thr Lys Ser Lys Glu
65                  70                  75                  80

Val Ser Ile Asn Val Asn Phe Ser Val Gly Phe Thr Ser Glu Phe Ile
                85                  90                  95

Gln Ala Ser Val Glu Tyr Gly Phe Gly Ile Thr Ile Gly Glu Gln Asn
            100                 105                 110

Thr Ile Glu Arg Ser Val Ser Thr Thr Ala Gly Pro Asn Glu Tyr Val
        115                 120                 125

Tyr Tyr Lys Val Tyr Ala Thr Tyr Arg Lys Tyr Gln Ala Ile Arg Ile
    130                 135                 140

Ser His Gly Asn Ile Ser Asp Asp Gly Ser Ile Tyr Lys Leu Thr Gly
145                 150                 155                 160

Ile Trp Leu Ser Lys Thr Ser Ala Asp Ser Leu Gly Asn Ile Asp Gln
                165                 170                 175

Gly Ser Leu Ile Glu Thr Gly Glu Arg Cys Val Leu Thr Val Pro Ser
            180                 185                 190

Thr Asp Ile Glu Lys Glu Ile Leu Asp Leu Ala Ala Ala Thr Glu Arg
        195                 200                 205

Leu Asn Leu Thr Asp Ala Leu Asn Ser Asn Pro Ala Gly Asn Leu Tyr
    210                 215                 220

Asp Trp Arg Ser Ser Asn Ser Tyr Pro Trp Thr Gln Lys Leu Asn Leu
225                 230                 235                 240

His Leu Thr Ile Thr Ala Thr Gly Gln Lys Tyr Arg Ile Leu Ala Ser
                245                 250                 255

Lys Ile Val Asp Phe Asn Ile Tyr Ser Asn Asn Phe Asn Asn Leu Val
            260                 265                 270

Lys Leu Glu Gln Ser Leu Gly Asp Gly Val Lys Asp His Tyr Val Asp
        275                 280                 285

Ile Ser Leu Asp Ala Gly Gln Tyr Val Leu Val Met Lys Ala Asn Ser
    290                 295                 300

Ser Tyr Ser Gly Asn Tyr Pro Tyr Ser Ile Leu Phe Gln Lys Phe
305                 310                 315

<210> SEQ ID NO 2
<211> LENGTH: 4188
<212> TYPE: DNA
<213> ORGANISM: Artificial Sequence
<220> FEATURE:
<223> OTHER INFORMATION: plasmid vector

<400> SEQUENCE: 2

| | | |
|---|---|---|
|ggatctgcga tcgctccggt gcccgtcagt gggcagagcg cacatcgccc acagtccccg|60|
|agaagttggg gggagggggtc ggcaattgaa cgggtgccta gagaaggtgg cgcggggtaa|120|
|actgggaaag tgatgtcgtg tactggctcc gccttttttcc cgagggtggg ggagaaccgt|180|
|atataagtgc agtagtcgcc gtgaacgttc tttttcgcaa cgggtttgcc gccagaacac|240|
|agctgaagct tcgaggggct cgcatctctc cttcacgcgc ccgccgccct acctgaggcc|300|
|gccatccacg ccggttgagt cgcgttctgc cgcctcccgc tgtggtgcc tcctgaactg|360|
|cgtccgccgt ctaggtaagt ttaaagctca ggtcgagacc gggcctttgt ccggcgctcc|420|
|cttggagcct acctagactc agccggtctc cacgctttg cctgaccctg cttgctcaac|480|
|tctacgtctt tgtttcgttt tctgttctgc gccgttacag atccaagctg tgaccggcgc|540|

-continued

```
ctacctgaga tcaccggcga aggagggcca ccatgtacag gatgcaactc ctgtcttgca      600
ttgcactaag tcttgcactt gtcacgaatt cgatatcggc catggttaga tctgtggagt      660
gcccaccttg cccagcacca cctgtggcag gaccttcagt cttcctcttc cccccaaaac      720
ccaaggacac cctgatgatc tccagaaccc ctgaggtcac gtgcgtggtg gtggacgtga      780
gccacgaaga ccccgaggtc cagttcaact ggtacgtgga cggcatggag gtgcataatg      840
ccaagacaaa gccacgggag gagcagttca acagcacgtt ccgtgtggtc agcgtcctca      900
ccgtcgtgca ccaggactgg ctgaacggca aggagtacaa gtgcaaggtc tccaacaaag      960
gcctcccagc ccccatcgag aaaaccatct ccaaaaccaa agggcagccc cgagaaccac     1020
aggtgtacac cctgccccca tcccgggagg agatgaccaa gaaccaggtc agcctgacct     1080
gcctggtcaa aggcttctac cccagcgaca tcgccgtgga gtgggagagc aatgggcagc     1140
cggagaacaa ctacaagacc acacctccca tgctggactc cgacggctcc ttcttcctct     1200
acagcaagct caccgtggac aagagcaggt ggcagcaggg gaacgtcttc tcatgctccg     1260
tgatgcatga ggctctgcac aaccactaca cacagaagag cctctccctg tctccgggta     1320
aatgagtgcc acggctagct ggccagacat gataagatac attgatgagt ttggacaaac     1380
cacaactaga atgcagtgaa aaaaatgctt tatttgtgaa atttgtgatg ctattgcttt     1440
atttgtaacc attataagct gcaataaaca agttaacaac aacaattgca ttcattttat     1500
gtttcaggtt caggggggagg tgtgggaggt ttttaaagc aagtaaaacc tctacaaatg     1560
tggtatggaa ttaattctaa atacagcat agcaaaactt taacctccaa atcaagcctc     1620
tacttgaatc ctttttctgag ggatgaataa ggcataggca tcaggggctg ttgccaatgt     1680
gcattagctg tttgcagcct caccttcttt catggagttt aagatatagt gtattttccc     1740
aaggtttgaa ctagctcttc atttctttat gttttaaatg cactgacctc ccacattccc     1800
tttttagtaa aatattcaga ataatttaa atacatcatt gcaatgaaaa taaatgtttt     1860
ttattaggca gaatccagat gctcaaggcc cttcataata tcccccagtt tagtagttgg     1920
acttagggaa caaaggaacc tttaatagaa attggacagc aagaaagcga gcttctagct     1980
tatcctcagt cctgctcctc tgccacaaag tgcacgcagt gccggccgg gtcgcgcagg     2040 gcgaactccc gccccacgg ctgctcgccg atctcggtca tggccggccc ggaggcgtcc     2100
cggaagttcg tggacacgac ctccgaccac tcggcgtaca gctcgtccag gccgcgcacc     2160
cacacccagg ccagggtgtt gtccggcacc acctggtcct ggaccgcgct gatgaacagg     2220
gtcacgtcgt cccggaccac accggcgaag tcgtcctcca cgaagtcccg ggagaacccg     2280
agccggtcgg tccagaactc gaccgctccg gcgacgtcgc gcgcggtgag caccggaacg     2340
gcactggtca acttggccat gatggctcct cctgtcagga gggaaagag aagaaggtta     2400 gtacaattgc tatagtgagt tgtattatac tatgcagata tactatgcca atgattaatt     2460
gtcaaactag gctgcagggg ttcatagtgc cacttttcct gcactgcccc atctcctgcc     2520 cacccttttcc caggcataga cagtcagtga cttaccaaac tcacaggagg gagaaggcag     2580
aagcttgaga cagacccgcg ggaccgccga actgcgaggg gacgtggcta gggcggcttc     2640
ttttatggtg cgcggccct cggaggcagg gcgctcgggg aggcctagcg gccaatctgc     2700
ggtggcagga ggcggggccg aaggccgtgc ctgaccaatc cggagcacat aggagtctca     2760
gccccccgcc ccaaagcaag gggaagtcac gcgcctgtag cgccagcgtg ttgtgaaatg     2820
ggggcttggg ggggttgggg ccctgactag tcaaaacaaa ctcccattga cgtcaatggg     2880
gtggagactt ggaaatcccc gtgagtcaaa ccgctatcca cgcccattga tgtactgcca     2940
```

```
aaaccgcatc atcatggtaa tagcgatgac taatacgtag atgtactgcc aagtaggaaa    3000
gtcccataag gtcatgtact gggcataatg ccaggcgggc catttaccgt cattgacgtc    3060 aataggggc gtacttggca tatgatacac ttgatgtact gccaagtggg cagtttaccg    3120
taaatactcc acccattgac gtcaatggaa agtccctatt ggcgttacta tgggaacata    3180
cgtcattatt gacgtcaatg ggcggggtc gttgggcggt cagccaggcg gccatttac     3240 cgtaagttat gtaacgcctg caggttaatt aagaacatgt gagcaaaagg ccagcaaaag    3300
gccaggaacc gtaaaaaggc cgcgttgctg gcgttttcc ataggctccg ccccctgac     3360 gagcatcaca aaaatcgacg ctcaagtcag aggtggcgaa acccgacagg actataaaga    3420
taccaggcgt ttccccctgg aagctccctc gtgcgctctc ctgttccgac cctgccgctt    3480
accggatacc tgtccgcctt tctcccttcg ggaagcgtgg cgctttctca tagctcacgc    3540
tgtaggtatc tcagttcggt gtaggtcgtt cgctccaagc tgggctgtgt gcacgaaccc    3600
cccgttcagc ccgaccgctg cgccttatcc ggtaactatc gtcttgagtc caacccggta    3660
agacacgact tatcgccact ggcagcagcc actggtaaca ggattagcag agcgaggtat    3720
gtaggcggtg ctacagagtt cttgaagtgg tggcctaact acggctacac tagaagaaca    3780
gtatttggta tctgcgctct gctgaagcca gttaccttcg gaaaaagagt tggtagctct    3840
tgatccggca acaaaccac cgctggtagc ggtggttttt ttgtttgcaa gcagcagatt    3900
acgcgcagaa aaaaggatc tcaagaagat cctttgatct tttctacggg gtctgacgct    3960
cagtggaacg aaaactcacg ttaagggatt ttggtcatgg ctagttaatt aacatttaaa    4020
tcagcggccg caataaaata tctttatttt cattacatct gtgtgttggt ttttgtgtg    4080 aatcgtaact aacatacgct ctccatcaaa acaaaacgaa acaaaacaaa ctagcaaaat    4140
aggctgtccc cagtgcaagt gcaggtgcca gaacatttct ctatcgaa                 4188

<210> SEQ ID NO 3
<211> LENGTH: 96
<212> TYPE: DNA
<213> ORGANISM: Artificial Sequence
<220> FEATURE:
<223> OTHER INFORMATION: primer

<400> SEQUENCE: 3
atcgagctta gatgctggac aatatgttct cgtaatgaaa gctaattcat catatagtgg    60
aaattaccct tattcaatat tatttcaaaa atttgc                              96

<210> SEQ ID NO 4
<211> LENGTH: 100
<212> TYPE: DNA
<213> ORGANISM: Artificial Sequence
<220> FEATURE:
<223> OTHER INFORMATION: primer

<400> SEQUENCE: 4
catggcaaat tttgaaata atattgaata agggtaattt ccactatatg atgaattagc    60
tttcattacg agaacatatt gtccagcatc taagctcgat                         100

<210> SEQ ID NO 5
<211> LENGTH: 280
<212> TYPE: PRT
<213> ORGANISM: Artificial Sequence
<220> FEATURE:
<223> OTHER INFORMATION: Fusion protein containing Clostridium
      perfringens enterotoxin residues 290-319 and human IgG Fc region
``` peptide

<400> SEQUENCE: 5

Met Tyr Arg Met Gln Leu Leu Ser Cys Ile Ala Leu Ser Leu Ala Leu
1               5                   10                  15

Val Thr Asn Ser Ile Ser Ser Leu Asp Ala Gly Gln Tyr Val Leu Val
            20                  25                  30

Met Lys Ala Asn Ser Ser Tyr Ser Gly Asn Tyr Pro Tyr Ser Ile Leu
        35                  40                  45

Phe Gln Lys Phe Ala Met Val Arg Ser Val Glu Cys Pro Pro Cys Pro
    50                  55                  60

Ala Pro Pro Val Ala Gly Pro Ser Val Phe Leu Phe Pro Pro Lys Pro
65                  70                  75                  80

Lys Asp Thr Leu Met Ile Ser Arg Thr Pro Glu Val Thr Cys Val Val
            85                  90                  95

Val Asp Val Ser His Glu Asp Pro Glu Val Gln Phe Asn Trp Tyr Val
            100                 105                 110

Asp Gly Met Glu Val His Asn Ala Lys Thr Lys Pro Arg Glu Glu Gln
        115                 120                 125

Phe Asn Ser Thr Phe Arg Val Val Ser Val Leu Thr Val Val His Gln
    130                 135                 140

Asp Trp Leu Asn Gly Lys Glu Tyr Lys Cys Lys Val Ser Asn Lys Gly
145                 150                 155                 160

Leu Pro Ala Pro Ile Glu Lys Thr Ile Ser Lys Thr Lys Gly Gln Pro
            165                 170                 175

Arg Glu Pro Gln Val Tyr Thr Leu Pro Pro Ser Arg Glu Glu Met Thr
        180                 185                 190

Lys Asn Gln Val Ser Leu Thr Cys Leu Val Lys Gly Phe Tyr Pro Ser
    195                 200                 205

Asp Ile Ala Val Glu Trp Glu Ser Asn Gly Gln Pro Glu Asn Asn Tyr
210                 215                 220

Lys Thr Thr Pro Pro Met Leu Asp Ser Asp Gly Ser Phe Phe Leu Tyr
225                 230                 235                 240

Ser Lys Leu Thr Val Asp Lys Ser Arg Trp Gln Gln Gly Asn Val Phe
            245                 250                 255

Ser Cys Ser Val Met His Glu Ala Leu His Asn His Tyr Thr Gln Lys
        260                 265                 270

Ser Leu Ser Leu Ser Pro Gly Lys
    275                 280

<210> SEQ ID NO 6
<211> LENGTH: 39
<212> TYPE: DNA
<213> ORGANISM: artificial
<220> FEATURE:
<223> OTHER INFORMATION: PCR primer

<400> SEQUENCE: 6
agatgttaat ggatccatgc ttagtaacaa tttaaatcc                              39

```
<210> SEQ ID NO 7
<211> LENGTH: 38
<212> TYPE: DNA
<213> ORGANISM: artificial
<220> FEATURE:
<223> OTHER INFORMATION: PCR primer

<400> SEQUENCE: 7
aaagctttta aaatttttga aataatattg aataaggg                              38
```